US010633374B2

(12) United States Patent
Spiegel et al.

(10) Patent No.: US 10,633,374 B2
(45) Date of Patent: Apr. 28, 2020

(54) SMALL MOLECULE BASED ANTIBODY-RECRUITING COMPOUNDS FOR CANCER TREATMENT

(71) Applicant: YALE UNIVERSITY, New Haven, CT (US)

(72) Inventors: David Spiegel, New Haven, CT (US); Anthony Rullo, Hamilton (CA)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 15/890,040

(22) Filed: Feb. 6, 2018

(65) Prior Publication Data
US 2018/0155332 A1 Jun. 7, 2018

Related U.S. Application Data

(63) Continuation-in-part of application No. PCT/US2016/045280, filed on Aug. 3, 2016.

(60) Provisional application No. 62/201,812, filed on Aug. 6, 2015, provisional application No. 62/290,793, filed on Feb. 3, 2016.

(51) Int. Cl.
| | |
|---|---|
| C07D 413/04 | (2006.01) |
| C07D 211/60 | (2006.01) |
| A61K 31/451 | (2006.01) |
| A61K 31/454 | (2006.01) |
| A61K 45/06 | (2006.01) |
| C07K 16/30 | (2006.01) |
| A61P 35/04 | (2006.01) |

(52) U.S. Cl.
CPC .......... *C07D 413/04* (2013.01); *A61K 31/451* (2013.01); *A61K 31/454* (2013.01); *A61K 45/06* (2013.01); *A61P 35/04* (2018.01); *C07D 211/60* (2013.01); *C07K 16/30* (2013.01)

(58) Field of Classification Search
CPC .... A61K 31/451; A61K 31/454; A61K 45/06; C07D 211/60; C07D 413/04; C07K 16/30
See application file for complete search history.

(56) References Cited

U.S. PATENT DOCUMENTS

2013/0338144 A1* 12/2013 Meroueh ............... C07D 413/04
514/217.1

FOREIGN PATENT DOCUMENTS

| WO | 2010077680 A2 | 7/2010 | |
|---|---|---|---|
| WO | 2011046946 A2 | 4/2011 | |
| WO | 2012068366 A2 | 5/2012 | |
| WO | 2012119079 A1 | 9/2012 | |
| WO | WO-2013070688 A1 * | 5/2013 | ............. A61K 45/06 |
| WO | 2013162757 A1 | 10/2013 | |
| WO | 2013166110 A1 | 11/2013 | |
| WO | 2014178878 A1 | 11/2014 | |

OTHER PUBLICATIONS

Jemal, A., Siegel, R., Xu, J., Ward, E. (2010) Cancer statistics 2010, CA Cancer J. Clin. 60, 277-300.
Garbe, C., Eigentler, T. K., Keilholz, U., Hauschild, A., Kirkwood, J. M. (2011) Systematic review of medical treatment in melanoma: current status and future prospects, The Oncologist 16, 5-24.
Boyle, P., Levin, B., Eds. (2008) World Cancer Report 2008, pp. 438-443, International Agency for Research on Cancer, Lyon.
Andreasen, P. A., Kjoller, L., Christensen, L., Duffy, M. J. (1997) The urokinase-type plasminogen activator system in cancer metastasis: A review, Int. J. Cancer 72, 1-22.
Duffy, M. J. (1993) Urokinase-type plasminogen activator and malignancy, Fibrinolysis 7, 295-302.
Saksela, O., Rifkin, D. B. (1988) Cell-associated plasminogen activation: Regulation and physiological functions, Ann. Rev. Cell. Biol. 4, 93-126.
Del Rosso, M., Fibbi, G., Pucci, M., D'Alessio, S. A., Del Rosso, A., Magnelli, L., Chiarugi, V. (2002) Multiple pathways of cell invasion are regulated by multiple families of serine proteases, Clin. & Exp. Metastasis 19, 193-207.
Jessani, N., Liu, Y., Humphrey, M., Cravatt, B. F. (2002) Enzyme activity profiles of the secreted and membrane proteome that depict cancer cell invasiveness. Proc. Natl. Acad. Sci. U.S.A. 99, 10335-10340.
Romer, J., Nielsen, B. S., Ploug, M. (2004) The urokinase receptor as a potential target in cancer therapy, Curr. Pharm. Des. 10, 2359-2376.
Blasi, F., Carmeliet, P. (2002) uPAR: A versatile signaling orchestrator, Nat. Rev. Mol. Cell. Biol. 3, 932-943.
Duffy, M. J. (1996) Proteases as prognostic markers in cancer Clin. Cancer. Res. 1996, 2, 613-618.

(Continued)

*Primary Examiner* — Sarah Pihonak
(74) *Attorney, Agent, or Firm* — Henry D. Coleman; R. Neil Sudol

(57) ABSTRACT

The present invention relates to chimeric (including bifunctional) compounds, compositions comprising those compounds and methods of treating cancer in a patient or subject, especially including metastatic cancer where cancer cells exhibit overexpression (heightened expression) of cell surface urokinase-type plasminogen activator receptor (urokinase receptor) compared to normal (non-cancerous) cells. The compounds bind to the urokinase-type plasminogen activator receptor (uPAR) on the surface of a cancer cell, including a metastatic cancer cell, and consequently recruit native antibodies of the patient or subject where the antibodies can selectively degrade and/or deactivate targeted cancer cells through antibody-dependent cellular phagocytosis and antibody-dependent cellular cytotoxicity (ADCC) and/or complement dependent cytotoxicity (CDC) against a large number and variety of cancers, thus providing cancer cell death and an inhibition of growth, elaboration and/or metastasis of the cancer, including remission and cure of the patient's cancer.

36 Claims, 28 Drawing Sheets

(56) References Cited

OTHER PUBLICATIONS

Dano, K., Behrendt, N., Brunner, N., Ellis, V., Ploug, M., Pyke, C. (1994) The urokinase receptor: Protein structure and role in plasminogen activation and cancer invasion, Fibrinolysis 8 suppl 1, 189-203.

Quax, P. H. A., van Muijen, G. N. P., Weening-Verhoeff, E. J. D., Lund, L. R., Dano, K., Ruiter, D. J., Verheijen, J. H. (1991) Metastatic Behavior of human melanoma cell lines in nude mice correlates with urokinase-type plasminogen activator, its type-1 inhibitor, and urokinase-mediated matrix degradation, J. Cell. Biol. 115, 191-199.

Madsen, M. A., Deryugina, E. I., Niessen, S., Cravatt, B. F., Quigley, J. P. (2006) Activity-based protein profiling implicates urokinase activation as a key step in human fibrosarcoma intravasation, J. Biol. Chem. 281, 15997-16007.

Sier, C. F., Stephens, R., Bizik, J., Mariani, A., Bassan, M., Pedersen, N., Frigerio, L., Ferrari, A., Dano, K., Brünner, N., Blasi, F. (1998) The level of urokinase-type activator receptor is increased in serum of ovarian cancer patients, Cancer Res. 58, 1843-1849.

Harbeck, N., Kates, R. E., Gauger, K., Willems, A., Kiechle, M., Magdolen, V., Schmitt, M. (2004) Urokinase-type plasminogen activator (uPA) and its inhibitor PAI-1: Novel tumor-derived factors with a high prognostic and predictive impact in breast cancer, Thromb. Haemost. 91, 450-456.

Duffy, M. J., O'Grady, P., Devaney, D., O'Siorain, L., Fennelly, J. J., Lijnen, H. J. (1998) Urokinase-plasminogen activator, a marker for aggressive breast carcinomas, Cancer 62, 531-533.

Herszenyi, L., Plebani, M., Carraro, P., de Paoli, M., Roveroni, G., Cardin, R., Tulassay, Z., Naccarato, R., Farinati, F. (1999) The role of cystein and serine proteases in colorectal carcinoma, Cancer 86, 1135-1142.

Harvey, S. R., Hurd, T. C., Markus, G., Martinick, M. I., Penetrante, R. M., Tan, D., Venkataraman, P., DeSouza, N., Sait, S. N. J., Driscoll, D. L., Gibbs, J. F. (2003) Evaluation of urinary plasminogen activator, its receptor, matrix metalloproteinase-9 and von Willebrand factor in pancreatic cancer, Clin. Cancer Res. 9, 4935-4943.

Konecny, G., Untch, M., Pihan, A., Kimmig, R., Gropp, M., Stieber, P., Hepp, H., Slamon, D., Pegram, M. (2001) Association of urokinase-type plasminogen activator and its inhibitor with disease progression and prognosis in ovarian cancer, Clin. Cancer Res. 7, 1743-1749.

Schmitt, M., Wilhelm, O. G., Reuning, U., Krüger, A., Harbeck, N., Lengyel, E., Graeff, H., Gänsbacher, B., Kessier, H. Bürgle, M., Stürzebecher, J., Sperl, S. Magdolen, V. (2000) The urokinase-type plasminogen activator system as a novel target for tumor therapy, Fibrinolysis & Proteolysis 14, 114-132.

Ertongur, S., Lang, S., Mack, B., Wosikowski, K., Muehlenweg, B., Gires, O. (2004) Inhibition of the invasion capacity of carcinoma cells by WX-UK1, a novel synthetic inhibitor of the urokinase-type plasminogen activator system, Int. J. Cancer 2004, 110, 815-824.

Ossowski, L., Reich, E. (1983) Antibodies to plasminogen activator inhibit human tumor metastasis, Cell 35, 611¬¬-619.

Liu, S., Aaronson, H., Mitola, D. J., Leppla, S. H., Bugge, T. H. (2003) Potent antitumor activity of a urokinase-activated engineered anthrax toxin, Proc. Natl. Acad. Sci. U.S.A. 100, 657-662.

Min, H. Y., Doyle, L., V., Vitt, C. R., Zandonella, C. L., Stratton-Thomas, J. R., Shuman, M. A., Rosenberg, S. (1996) Urokinase receptor antagonists inhibit angiogenesis and primary tumor growth in syngeneic mice, Cancer Res. 56, 2428-2433.

Vallera, D. A., Li, C., Jin, N., Mortari-Panoskaltsis, A., Hall, W. A. (2002) Targeting urokinase-type plasminogen activator receptor on human glioblastoma tumors with diphtheria toxin fusion protein DTAT, J. Natl. Cancer Inst. 94, 597-606.

Spiegel, D. A. (2010) Synthetic immunology to engineer human immunity, Nat. Chem. Biol. 6, 871-872.

Murelli, R. P., Zhang, A. X., Michel, J., Jorgensen, W. L., Spiegel, D. A. (2009) Chemical control over immune recognition: A class of antibody-recruiting small molecules that target prostate cancer, J. Am. Chem. Soc. 131, 17090-17092.

Lu, Y., Low, P. S. (2002) Folate targeting of haptens to cancer cell surfaces mediates immunotherapy of syngeneic murine tumors, Cancer Immunol. Immunother. 51, 153-162.

Lu, Y., Sega, E., Low, P. S. (2005) Folate receptor-targeted immunotherapy: Induction of humoral and cellular immunity against hapten-decorated cancer cells, Int. J. Cancer 116, 710-719.

Popkov, M., Gonzalez, B., Sinha, S. C., Barbas, C. F., III. (2009) Instant immunity through chemically programmable vaccination and covalent self-assembly Proc. Natl. Acad. Sci. U.S.A. 106, 4378-4383.

Carlson, C. B., Mowery, P., Owen, R. M., Dykhuizen, E. C., Kiessling, L. L. (2007) Selective tumor cell targeting using low-affinity, multivalent interactions, ACS Chem. Biol. 2, 119-127.

Ortega, E., Kostovetzky, M., Larralde, C. (1984) Natural DNP-binding immunoglobulins and antibody nnultispecificity, Mol. Immunol. 21, 883-888.

Kettner, C., Shaw. E. (1981) Inactivation of trypsin-like enzymes with peptides of arginine chloromethyl ketone, Methods Enzymol. 80, 826-842.

Spraggon, G., Phillips, C., Nowak, U. K., Ponting, C. P., Saunders, D., Dobson, C. M., Stuart, D. I., Jones, E. Y. (1995) The crystal structure of the catalytic domain of human urokinase-type plasminogen activator, Structure 3, 681-691.

Williams, E. B., Krishnaswamy, S., Mann, K. G. (1989) Zymogen/enzyme discrimination using peptide chloromethyl ketones, J. Biol. Chem. 264, 7536-7545.

Walker, B., Elmore, D. T. (1984) The behaviour of urokinase and porcine kidney cell plasminogen activator towards some synthetic peptides Thromb. Res. 34, 103-107.

Binnema, D. J., van Iersel, J. J. L., Dooijewaard, G. (1986) Quantitation of urokinase antigen in plasma and culture media by use of an ELISA, Thromb. Res. 43, 569-577.

Rajagopal, V., Kreitman, R. J. (2000) Recombinant toxins that bind to the urokinase receptor are cytotoxic without requiring binding to the alpha2-macroglobulin receptor. J. Biol. Chem. 275, 7566-7573.

Bracher, M., Gould, H. J., Sutton, B. J., Dombrowicz, D., Karagiannis, S. N. (2007) Three-colour flow cytometric method to measure antibody-dependent tumour cell killing by cytotoxicity and phagocytosis, J. Immunol. Methods 323, 160-171.

Boltz-Nitulescu, G., Willheim, M., Spittler, A., Leutmezer. F., Tempfer, C., Winkler, S. (1995) Modulation of IgA, IgE, and IgG Fc receptor expression of human mononucler phagocytes by 1alpha,25-dihydroxyvitamin D3 and cytokines, J. Leuko. Biol. 58, 256-262.

Lu, Yingjuan, Klein, P. J., Westrick, E., Xu, L.-C., Santhapuram, H. K. R., Bloomfield, A., Howard, S. J., Vlahov, I. R., Ellis, P. R., Low, P. S., Leamon, C. P. (2009) Strategy to prevent drug-related hypersensitivity in folate-targeted hapten immunotherapy of cancer, AAPS J. 2, 628-638.

Kute, T. E., Savage, L., Stehle, J. R. Jr., Kim-Shapiro, J. W., Blanks, M. J., Wood, J., Vaughn, J. P. (2009) Breast tumor cells isolated from in vitro resistance to trastuzumab remain sensitive to trastuzumab anti-tumor effects in vivo and to ADCC killing, Cancer Immunol. Immunother. 58, 1887-1896.

Zhu, J., Wang, X., Xu, X., Abassi, Y. A. (2006) Dynamic and label-free monitoring of natural killer cell cytotoxic activity using electronic cell sensor arrays, J. Immunol. Methods 309, 25-33.

Weiner, G. J. (2007) Monoclonal antibody mechanisms of action in cancer, Immunol. Res. 39, 271-278.

Harris, T. D., Kalogeropoulos, S., Nguyen, T., Dwyer, G., Edwards, D. S., Liu, S., Bartis, J., Ellars, C., Onthank, D., Yalamanchili, P., Heminway, S., Robinson, S., Lazewatsky, J., Barrett, J. (2006) Bioconj. Chem. 17, 1294.

Sadakibara, S., Inukai, N. (1964) A New Reagent for the p-Nitrophenylation of Carboxylic Acids. Bull. Chem. Soc. Jap. 37, 1231.

Rueping, M., Mahajan, Y. R., Jaun, B., Seebach, D. (2004) Design, Synthesis and Structural Investigations of a Beta-Peptide Forming a 3(14)-Helix Stabilized by Electrostatic Interactions. Chem. Eur. J. 10, 1607.

Yu, N., Atienza, J. M., Bernard, J., Blanc, S., Zhu, J., Wang, X., Xu, X., Abassi, Y. A. (2006) Anal. Chem. 78, 35.

\* cited by examiner

FIGURE 4

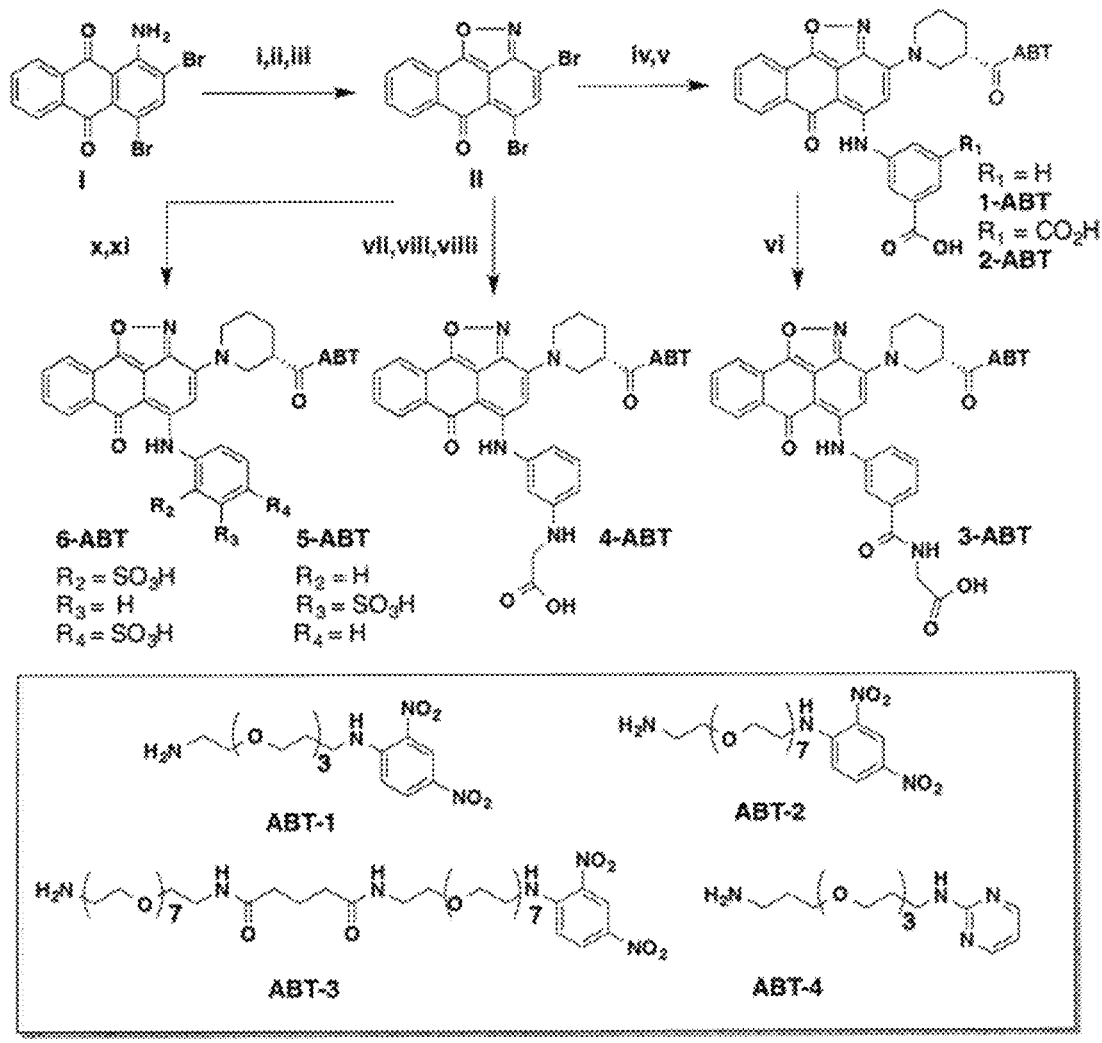

i. NaNO₂ / H₂SO₄ ii. NaN₃/H₂O iii.Tolune reflux iv. Methyl-3-aminobenzoate or, Dimethyl 5-aminoisophthalate, AlCl₃ / PhNO₂ v. ABT-1,2,or 3, DIPEA / DMF then NaOH/THF/MeOH 1:1:1 vi. 1-ABT-1, GlyOMe,HATU,DIPEA / DMF, then NaOH/THF/MeOH 1:1:1 vii. 3-bromoaniline, GlyOMe, CuI, N,N-diethylsalicylamide, K₃PO₄ / DMF viii. AlCl₃ / PhNO₂ viiii. ABT-1, DIPEA / DMF, then NaOH/THF/MeOH 1:1:1 x. metanillic acid, DIPEA / PhNO₂, or aniline-2,4-disulfonic acid, Li₂CO₃, Cu(OAc)₂ / DMF xi. ABT-1,2,or 3, DIPEA/ DMF FIGURE 8
Table 1

| ARM-U2 | R1 | R2 | R3 | R4 | $K_d$ (nM) |
|---|---|---|---|---|---|
| 1-ABT-1 | H | $CO_2H$ | H | H | 640 ± 180 |
| 1-ABT-2 | H | $CO_2H$ | H | H | 57 ± 22 |
| 1-ABT-3 | H | $CO_2H$ | H | H | 43 ± 20 |
| 1-(D)-ABT-1 | H | $CO_2H$ | H | H | 167 ± 40 |
| 1-(D)-ABT-2 | H | $CO_2H$ | H | H | 72 ± 17 |
| 2-ABT-1 | H | $CO_2H$ | H | $CO_2H$ | 408 ± 22 |
| 2-ABT-2 | H | $CO_2H$ | H | $CO_2H$ | 93 ± 39 |
| 3-ABT-1 | H | $CONHCH_2CO_2H$ | H | H | 445 ± 85 |
| 4-ABT-1 | H | $NHCH_2CO_2H$ | H | H | 240 ± 39 |
| 5-ABT-1 | H | $SO_3H$ | H | H | 493 ± 39 |
| 6-ABT-1 | $SO_3H$ | H | $SO_3H$ | H | 12 ± 1 |
| 6-ABT-2 | $SO_3H$ | H | $SO_3H$ | H | 66 ± 9.5 |
| 6-ABT-3 | $SO_3H$ | H | $SO_3H$ | H | 6.5 ± 2.5 |

FIGURE 9
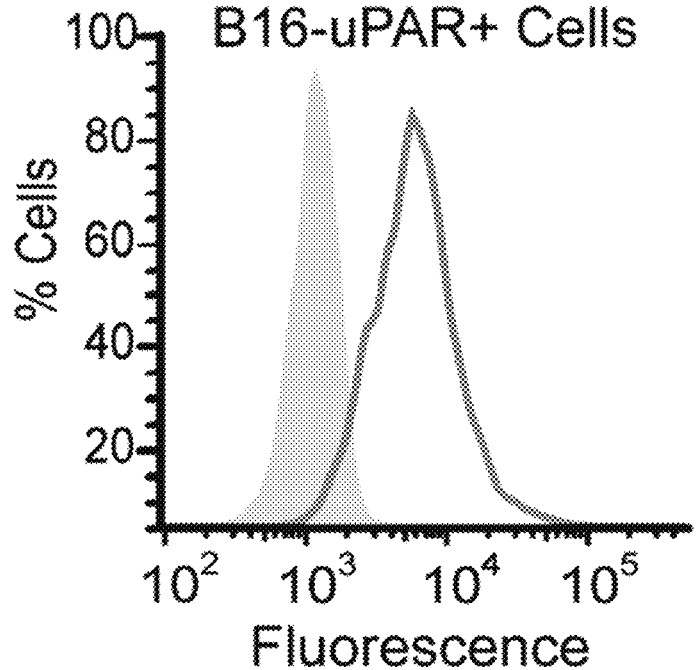
A. Binding of 6-ABT-1 on B16-uPAR+ Cells
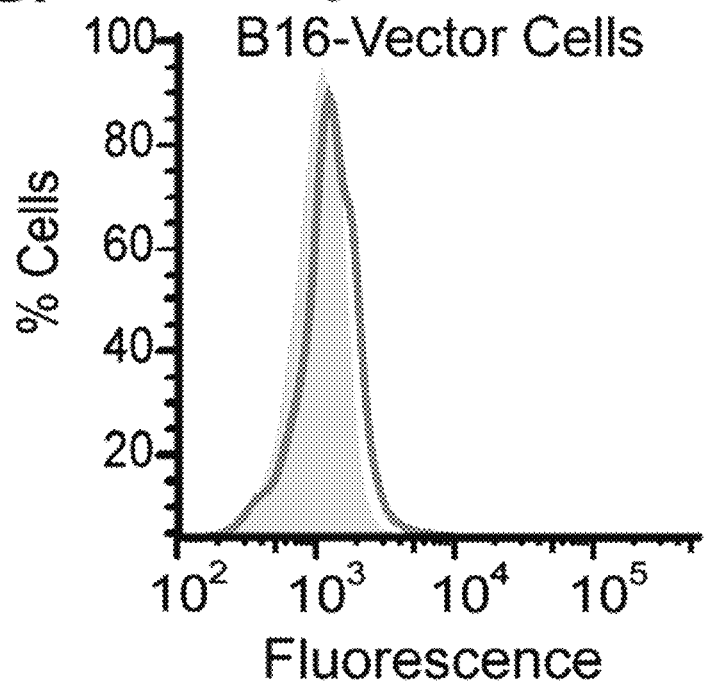
B. Binding of 6-ABT-1 on B16-Vector Cells Figure 9 (cont'd)
C. 6-ABT-1-Dependent Phagocytosis of uPAR+ A172 cells
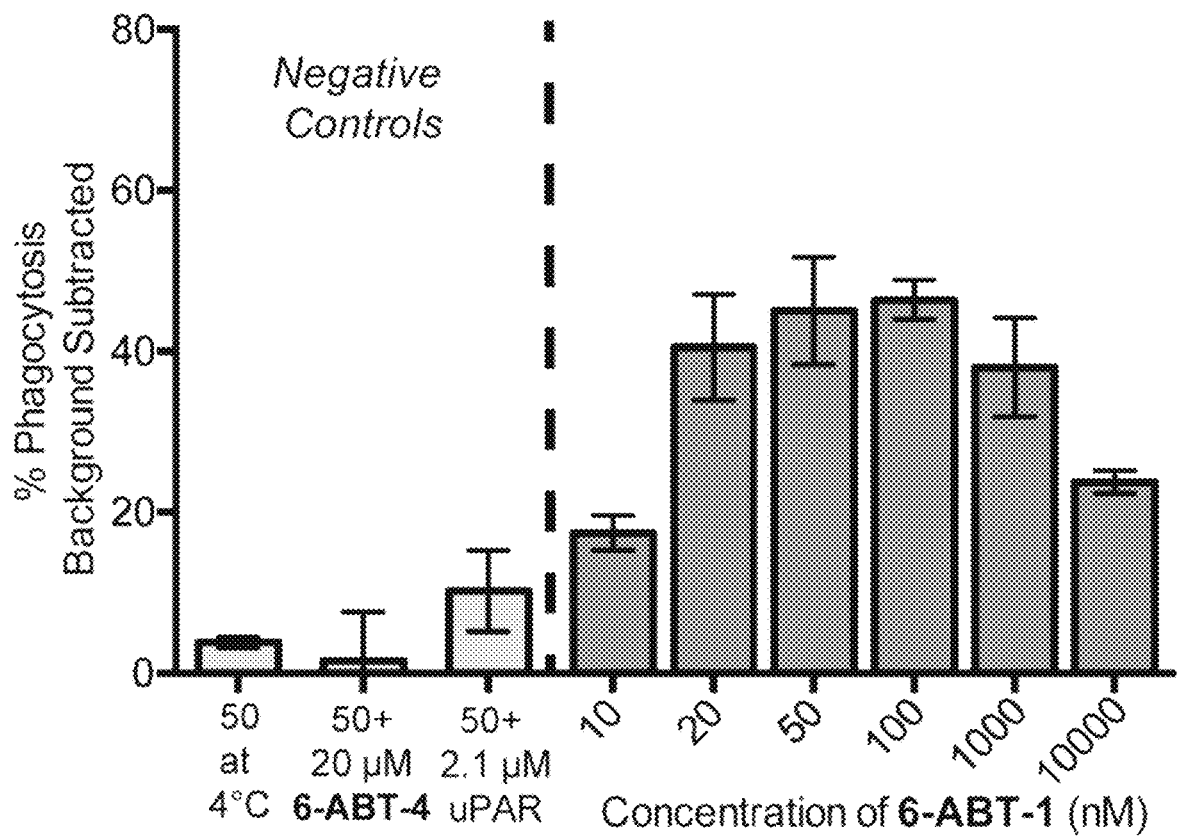
D. 6-ABT-1 (50nM) mediated phagocytosis of A172 target cells by u937 monocyte effector cells
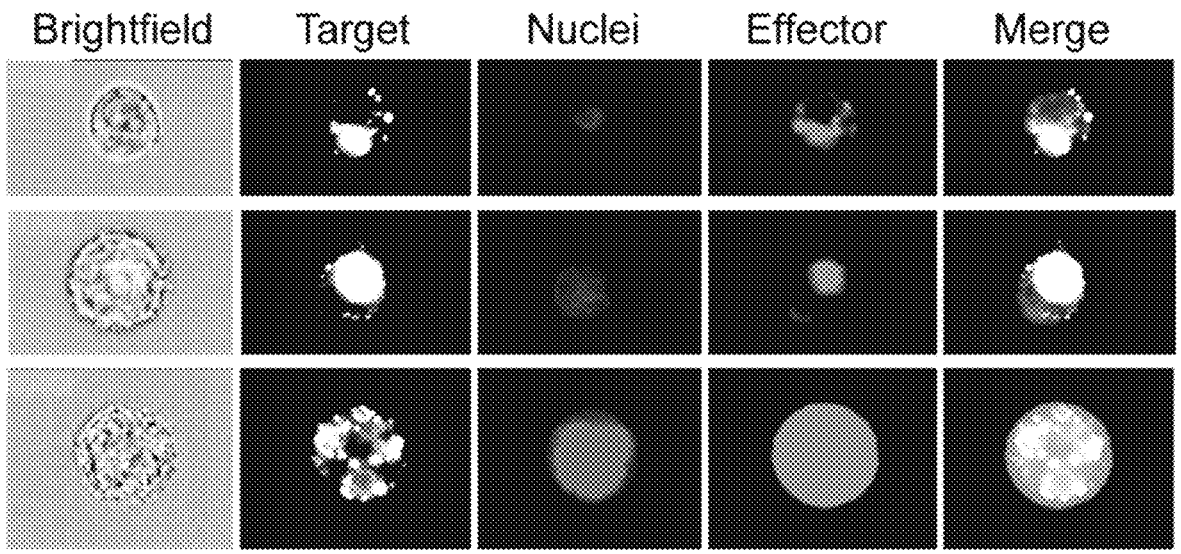

FIGURE 12
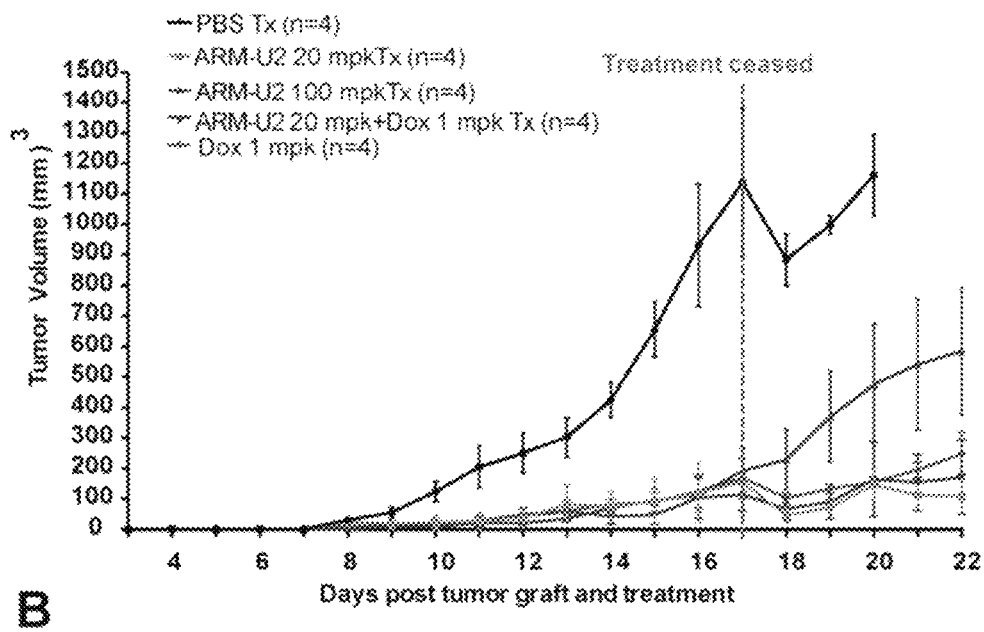
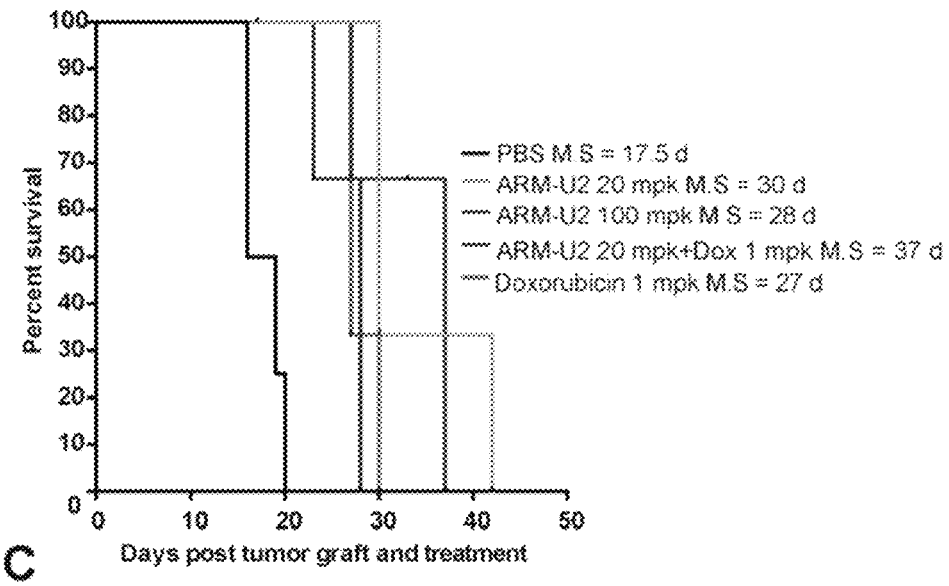
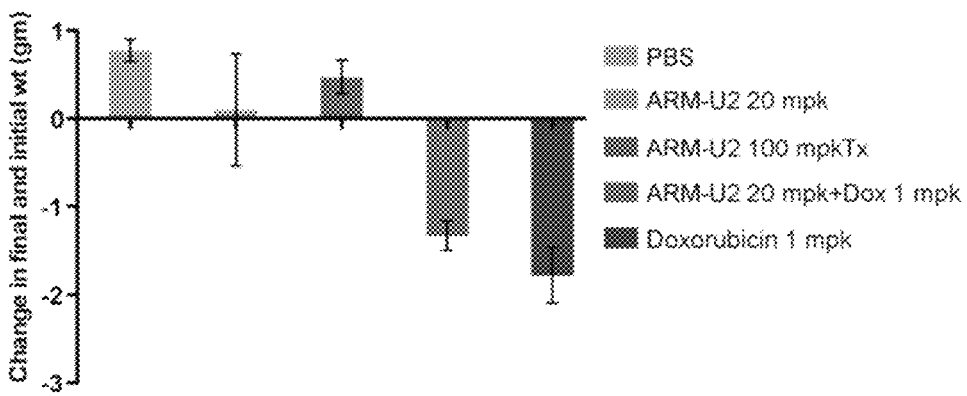

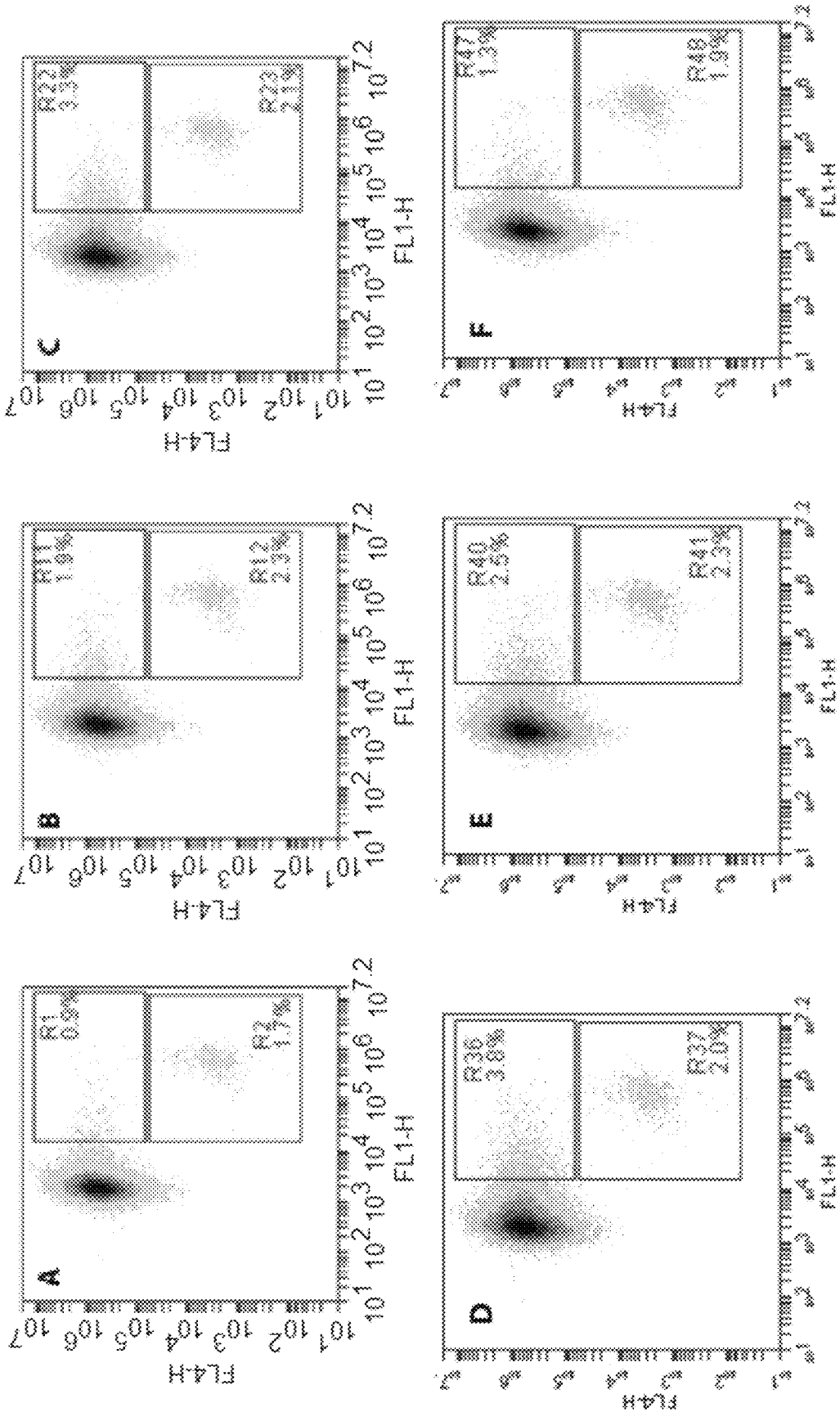

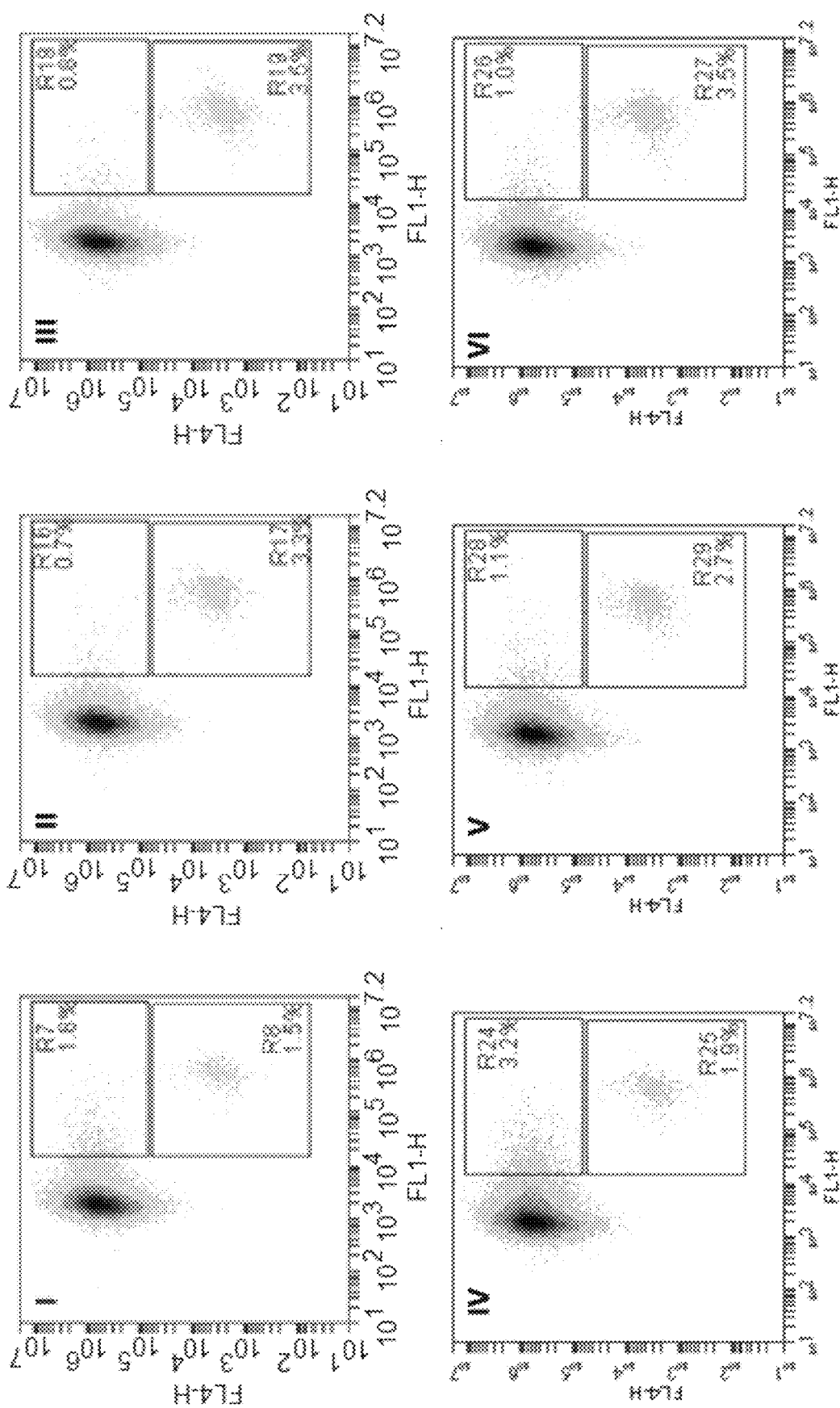

SMALL MOLECULE BASED ANTIBODY-RECRUITING COMPOUNDS FOR CANCER TREATMENT

RELATED APPLICATIONS AND GRANT SUPPORT

This application is a continuation-in-part application of International Patent Application Number PCT/US2016/045280 of International Filing Date Aug. 3, 2016 entitled "Small Molecule Based Antibody-Recruiting Compounds for Cancer Treatment", which claims the benefit of priority of United States provisional application Nos. 62/201,812, filed Aug. 6, 2015 and 62/290,793, filed Feb. 3, 2016, both applications entitled "Small Molecule Based Antibody-Recruiting Agent Targeting uPAR", the entire contents of said three applications being incorporated by reference herein.

This invention was made with government support under 1DP2OD002913-01 awarded by the National Institute of Health. The government has certain rights in the invention.

FIELD OF THE INVENTION

The present invention relates to chimeric (including bifunctional) compounds, compositions comprising those compounds and methods of treating cancer in a patient or subject, especially including metastatic cancer and other cancers where cancer cells exhibit overexpression (heightened expression) of cell surface urokinase-type plasminogen activator receptor (urokinase receptor) compared to normal (non-cancerous) cells. The compounds bind to the urokinase-type plasminogen activator receptor (uPAR) on the surface of a cancer cell, including a metastatic cancer cell, and consequently recruit native antibodies of the patient or subject where the antibodies can selectively remove, destroy, clear and/or deactivate targeted cancer cells through antibody-dependent cellular phagocytosis (ADCP), antibody-dependent cellular cytotoxicity (ADCC), complement dependent cytotoxicity (CDC) and/or other immune effector mechanisms against a large number and variety of cancers, thus providing cancer cell death and an inhibition of growth, elaboration and/or metastasis of the cancer, including remission and cure of the patient's cancer.

INTRODUCTION/BACKGROUND OF THE INVENTION

Cancer is currently the second leading cause of death in the United States. Metastatic cancers are especially difficult to treat and are associated with higher levels of mortality compared to benign tumors. American men and women have a 38-44% chance of developing invasive cancers over the course of their lifetimes. Tumor metastasis involves cancer cell invasion of surrounding tissues, often accelerated by cell surface proteases. One such protease known as the urokinase-type plasminogen activator (uPA) is capable of breaking down extracellular matrix proteins and activating migration-inducing signal cascades through binding to the urokinase-type plasminogen activator receptor (uPAR).

A large body of evidence suggests that uPA and uPAR expression are substantially higher on invasive malignant cancer cells than on healthy cells or benign tumors. In clinical settings, high levels of uPAR are used as diagnostic measures for metastatic potential and poor clinical outcome in several malignancies. Novel strategies to combat cancer are highly desirable due to the limitations of the more traditional treatment options, including radiation therapy and chemotherapy. These treatment methods are not only associated with significant side effects but are also limited with respect to their effectiveness in the treatment of late stage cancers.

The ability to target cancer cells selectively is thus of great importance, with the potential to significantly reduce toxicity and off-target effects, thereby reducing side effects experienced by the patient. New approaches to treat cancer that combine the advantages of traditional small molecules and biologics could address many of the limitations associated with currently available therapies.

Anthroquinone-based small molecules have been identified previously as potential anti-cancer agents and have been shown to bind to uPAR in vitro with triple digit nM affinity capable of blocking cancer cell invasion, migration, and adhesion at double to triple uM concentrations (T. Mani et al). Previously, the development of an antineoplastic antibody-recruiting agent equipped with the urokinase protein as a uPAR target-binding domain was reported from the present laboratory. The molecule developed here, termed "ARM-U," was shown previously to selectively target uPAR-overexpressing A172 glioblastoma cells and facilitate anti-DNP antibody-dependent cellular phagocytosis (ADCP) at single digit nM concentrations. Although ARM-U has high-affinity binding to uPAR ($K_d$ of ~200 pM), its potential as a therapeutic is limited due to the incorporation of the large uPA protein with limited stability in vivo. This, plus the limitations associated with the administration of uPA protein limits its use.

The present invention describes the rational design of the highest affinity small molecule targeting the uPA site on uPAR ever reported. Novel small molecule derived ARM-U2 compounds demonstrate efficacy against metastatic cancer cells in cellular assays at low nM concentrations. Moreover, these compounds do not require the administration of uPA protein in order to facilitate its therapeutic efficacy, a clear advance over the prior art compounds.

The present invention also illuminates the nature of the non-covalent interactions with the uPA binding site on uPAR required for tight binding to uPAR. In addition, the present invention has provided experimentally supported computational predictions regarding the importance of basic residues in the uPA binding pocket for targeting small molecules selectively to uPAR and reports the first crystal structure of a uPAR targeting antibody recruiting small molecule binding the uPA binding site of uPAR. An additional feature of the present invention is that it demonstrate the high potency and efficacy of an antibody recruiting small molecule.

The present invention shows that (ARM-U2) binds uPAR on the surface of A172 glioblastoma and B16 melanoma cancer cells and recruits endogenous anti-DNP antibodies to the cell surface which in turn induce antibody dependent cellular phagocytosis and antibody dependent cellular cytotoxicity (see FIG. 1). Present preliminary in-vivo data show the ability of ARM-U2 to inhibit tumor formation using a B-16 xenograft mouse tumor model

BRIEF DESCRIPTION OF THE INVENTION

The present invention is directed to compounds according to the general chemical structure:

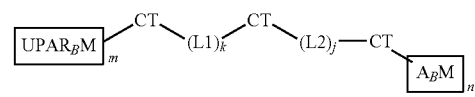

Where [uPARbM] is a moiety which binds to an active site of urokinase-type plasminogen activator receptor (uPAR) on the surface of cancer cells of a patient or subject;

[AbM] is an antibody binding moiety comprising a hapten which is capable of binding to an antibody in said patient or subject (preferably an endogenous antibody which pre-exists in the patient or subject without having to be raised prior to therapy);

Each L1 is a linker molecule which chemically links [uPARbM] to CT, L2 or [AbM] in said compound;

Each L2 is a linker molecule which chemically links [AbM] to CT, L1 or [uPARbM] in a molecule;

Each CT is independently an optional connector molecule which, when present links L1 or L2 to [uPARbM], L1 or L2 to [AbM] and L1 to L2;

Each j is independently 0, 1, 2, 3, 4 or 5 (preferably 0 or 1, more preferably 1);

Each k is independently 0, 1, 2, 3, 4 or 5 (preferably 0 or 1, more preferably 1), with the proviso that at least one CT is present when k and j are both 0 (preferably at least one of k and j is 1); and Each m and n is independently an integer from 1 to 15, 1 to 10, 1 to 5, 1 to 3, 2 to 3, 2 to 5, 1 to 2 or 1 (often m is 1 and n is 1-6, more often 1, 2, 3 or 4), or a pharmaceutically acceptable salt, solvate or polymorph thereof.

In certain embodiments, compounds according to the present invention are represented by the chemical structure:

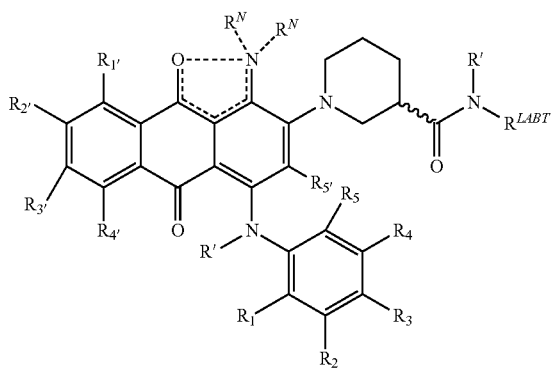

Wherein each $R^N$ is independently H or a $C_1$-$C_3$ alkyl group when N is an amine group or each $R^N$ is absent when N forms an isoxazole group by binding to the adjacent oxygen atom;

$R_1$, $R_2$, $R_3$, $R_4$ and $R_5$ are each independently H, a halogen (F, Cl, Br, I, preferably F), a $C_1$-$C_3$ alkyl group optionally substituted with one or two hydroxyl groups or up to three fluoro groups, $NO_2$, CN, a $(CH_2)_{m'}OR^E$ (O-alkyl) group, a $(CH_2)_{m'}COR^E$ (keto) group, a $(CH_2)_{m'}COOR^E$ (carboxy ester) group, a $(CH_2)_{m'}SO_3H$ group, a $(CH_2)_{m'}OCOR^E$ (oxycarbonyl ester) group,

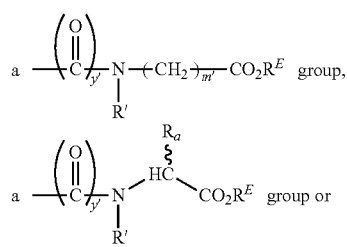

-continued

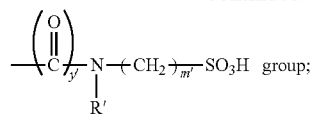

Each R' is independently H or a $C_1$-$C_3$ alkyl group (preferably H or $CH_3$, most often H);

$R_a$ is a sidechain derived from a natural or unnatural amino acid (D- or L-, preferably a L-amino acid) preferably selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), histidine (methyleneimidazole), isoleucine (1-methylpropane), leucine (2-methylpropane), lysine (butyleneamine), methionine (ethylmethylthioether), phenylalanine (benzyl), proline (R' forms a cyclic ring with $R_a$ and the adjacent nitrogen group to form a pyrrolidine group), hydroxyproline, serine (methanol), threonine (ethanol, 1-hydroxyethane), tryptophan (methyleneindole), tyrosine (methylene phenol) or valine (isopropyl)

Each $R^E$ is H or a $C_1$-$C_6$ alkyl group optionally substituted with one or two hydroxyl groups or up to three chloro or fluoro groups (preferably $R^E$ is H or a $C_1$-$C_3$ alkyl group);

$R_{1'}$, $R_{2'}$, $R_{3'}$, $R_{4'}$ and $R_{5'}$ are each independently H, a halogen (F, Cl, Br, I, preferably F), a $C_1$-$C_6$ (preferably $C_1$-$C_3$) alkyl group optionally substituted with one or two hydroxyl groups or up to three chloro or fluoro groups, $NO_2$, CN, a $(CH_2)_{m'}OR^E$ (O-alkyl) group, a $(CH_2)_{m'}CO$-$OR^E$ (carboxy ester) group, a $(CH_2)_{m'}O$—$COR^E$ (oxycarbonyl ester) group or a $(CH_2)_{m'}COR^E$ (keto) group;

Each m' is independently 0, 1, 2, 3, 4, 5, or 6 (preferably 0, 1, 2 or 3, more preferably 0 or 1);

Each y' is independently 0, 1 or 2 (preferably 0 or 1);

$R^{LABT}$ is an

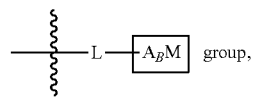

where L is a bond, at least one linker (preferably a single linker) which comprises a first linker group L1 which optionally includes a connector group CT and an optional linker group L2 which itself optionally includes a connector group CT, said first linker group L1 being linked to said second linker group L2 optionally (preferably) through a CT group; and

[AbM] is an antibody binding moiety comprising a hapten which is capable of binding to an antibody in said patient or subject, or a pharmaceutically acceptable salt, stereoisomer, enantiomer, solvate or polymorph thereof.

In preferred embodiments compounds according to the present invention is represented by the chemical structure:

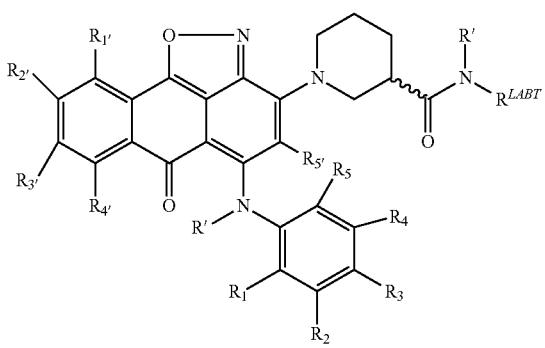

Where the substituents on the compound R', $R_{1'}$, $R_{2'}$, $R_{3'}$, $R_{4'}$, $R_{5'}$, $R_1$, $R_2$, $R_3$, $R_4$, $R_5$ and $R^{LABT}$ are the same as for the generic compound above or an enantiomer thereof.

In other preferred embodiments, compounds according to the present invention are represented by the chemical structure:

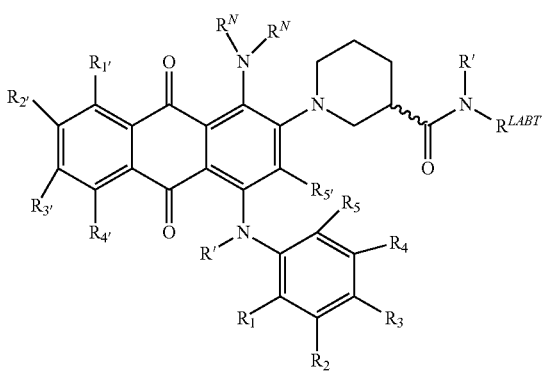

Where the substituents $R^N$, R', $R_{1'}$, $R_{2'}$, $R_{3'}$, $R_{4'}$, $R_{5'}$, $R_1$, $R_2$, $R_3$, $R_4$, $R_5$ and $R^{LABT}$ are the same as for the generic compound above.

In preferred embodiments of the invention, $R_1$ is H, $CO_2H$ or $SO_3H$; $R_2$ is H, $CO_2H$, $SO_3H$, —$NHCH_2$—$CO_2H$, —$NHCH_2$—$SO_3H$, —C(O)—$NHCH_2$—$CO_2H$ or —C(O)—$NHCH_2$—$SO_3H$; $R_3$ is H, $CO_2H$, $SO_3H$, —$NHCH_2$—$CO_2H$, —$NHCH_2$—$SO_3H$, —C(O)—$NHCH_2$—$CO_2H$ or —C(O)—$NHCH_2$—$SO_3H$ (preferably H, $CO_2H$ or $SO_3H$); $R_4$ is H, $SO_3H$ or $CO_2H$ (preferably H or $CO_2H$; $R^5$ is H, $SO_3H$ or $CO_2H$ (preferably H) and R', $R_{1'}$, $R_{2'}$, $R_{3'}$, $R_{4'}$, $R_{5'}$ are H, or a pharmaceutically acceptable salt or solvate thereof.

In other preferred embodiments of the invention,

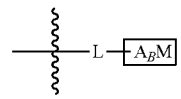

is

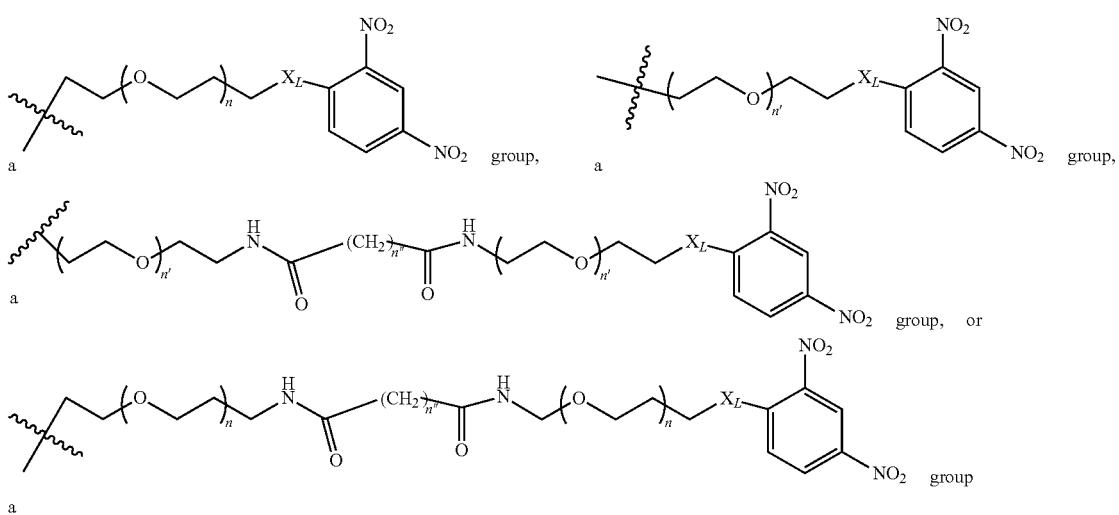

where $X_L$ is $N(R^1)$, O, S, S(O), $SO_2$, $S(O)_2O$, —$OS(O)_2$, or $OS(O)_2O$ (preferably $N(R^1)$ or O, more preferably $N(R^1)$); and $R^1$ is H, a $C_1$-$C_3$ alkyl group or a —$C(O)(C_1$-$C_3)$ group, preferably H;

each n and n' is independently 1 to 25, 1 to 15, 1 to 12, 2 to 11, 2 to 10, 2 to 8, 2 to 6, 2 to 5, 2 to 4 and 2 to 3 or 1, 2, 3, 4, 5, 6, 7, 8 or 9; and each n" is independently 0 to 8, often 1 to 7, or 1, 2, 3, 4, 5 or 6 (preferably 3 or 6).

In certain preferred embodiments, L, L1 and/or L2 are (poly)ethylene glycol groups comprising from 1 to 25, from 1 to 15, from 1 to 12, 2 to 11, 2 to 10, 2 to 8, 2 to 6, 2 to 5, 2 to 4 and 2 to 3 ethyleneglycol groups, which may be linked to ▭, CT and/or ▭ groups. In certain preferred embodiments of the invention, the connector group CT, when present, is a group as otherwise described herein, including a triazole group, an amide group (which may contain one or more methylene groups on either side of the amide), an alkylene group, a succinimide group, or a diamide group according to the chemical structure

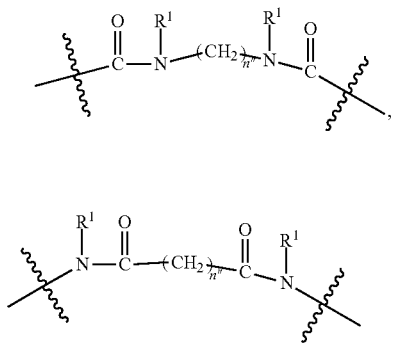

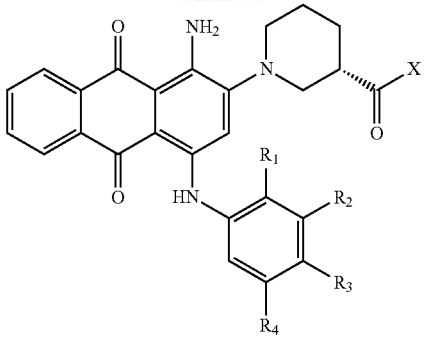

or

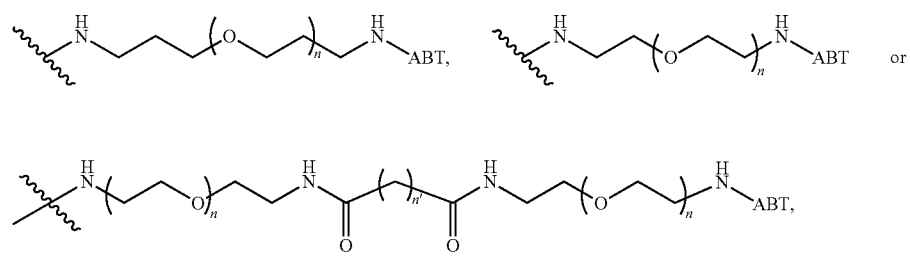

Wherein $R_1$, $R_2$, $R_3$ and $R_4$ are each independently H, $CO_2H$, $SO_3H$, $CONHCH_2CO_2H$ or $NHCH_2CO_2H$;

-continued

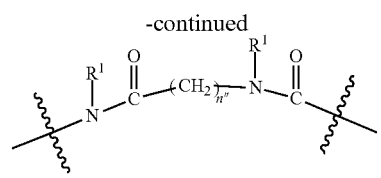

where $R^1$ is H or a $C_1$-$C_3$ alkyl group (preferably H) and n" is 0 to 8, often 1 to 7, or 1, 2, 3, 4, 5 or 6 (preferably 3). Note is the fact that the CT group may contain methylene groups of varying lengths which connect the CT group to [PHARM], the linker group and/or [AbM].

In certain embodiments, the [AbM] group is one or more dinitrophenyl (DNP) or rhamnose groups as described in greater detail herein.

Preferred compounds according to the present invention are presented in attached FIG. 4, Scheme 1, FIG. 6, Table 1, FIG. 7 and FIG. 8 (with reference to FIG. 4) hereof.

In preferred embodiments of the present invention are directed to compounds according to chemical structures:

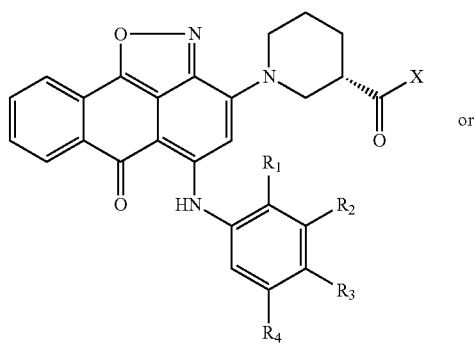

or n is 1-15, preferably 2-10, more often 3 or 7;

n' is 1-10, preferably=1-7, more often 2-6, often 3 or 6;

ABT is a DNP group or a rhamnose group, often a DNP group; or a pharmaceutically acceptable salt, stereoisomer (a diastereomer or enantiomer), solvate or polymorph thereof.

In another preferred embodiment, the present invention is directed to a compound according to the chemical structure:

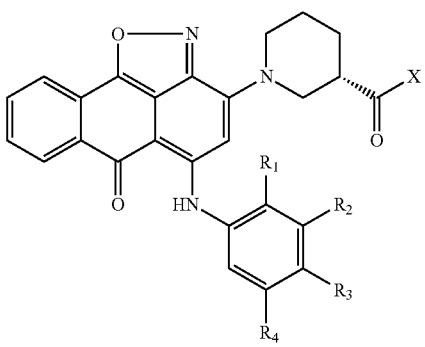

Wherein $R_1$, $R_3$ and $R_4$ are each H and $R_2$ is $CO_2H$; or $R_1$ and $R_3$ are each H and $R_2$ and $R_4$ are each $CO_2H$; or $R_1$, $R^3$ and $R_4$ are each H and $R_2$ is $CONHCH_2CO_2H$ or $NHCH_2CO_2H$; or $R_1$, $R_3$ and $R_4$ are each H and $R_2$ is $SO_3H$; or $R_1$ and $R_3$ are each $SO_3H$ and $R_2$ and $R_4$ are each H;

X is

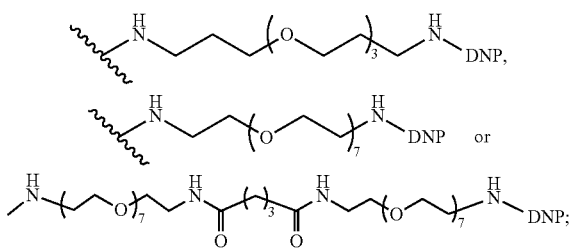

DNP is a

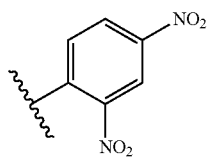

group; or
a pharmaceutically acceptable salt or stereoisomer (a diastereomer or enantiomer)

Additional preferred embodiments of compounds according to the present invention are presented in FIG. 7 hereof, including an enantiomer or diastereomer thereof.

In additional embodiments of the invention, a pharmaceutical composition comprises an effective amount of a compound as described above, optionally and preferably in combination with a pharmaceutically acceptable carrier, additive or excipient. In alternative aspects, pharmaceutical combination compositions comprise an effective amount of a compound as described herein, in combination with at least one additional agent which is used to treat cancer, including metastatic cancer, or a secondary condition or effect of cancer, especially metastatic cancer or alternative secondary effect, including one or more of bone pain, hyperplasia, osteoporosis, kidney failure, liver failure, etc., as otherwise described herein.

In a further aspect of the invention, compounds according to the present invention are used to treat cancer in a patient. The method of treating cancer comprises administering to a patient in need an effective amount of a compound as otherwise described herein in combination with a pharmaceutically acceptable carrier, additive or excipient, optionally in further combination with at least one additional agent which is effective in treating cancer, including metastatic cancer, or one or more of its secondary conditions or effects. The method of treatment may be combined with alternative treatments, such as radiation therapy, among others.

The present invention also relates to a method for inhibiting cancer to reduce the likelihood or inhibit the spread or metastasis of the cancer into other tissues of the patients' body for any cancer, and especially such cancers including bone, lymph (lymph nodes), bladder, vas deferens, kidneys, liver, lungs, pancreas, brain, prostate and ovaries, among others.

Pursuant to the present invention, synthetic compounds for controlling or creating human immunity pursuant to the present invention have the potential to revolutionize cancer treatment. Motivated by challenges in this arena, the present inventors provide a strategy to target metastatic cancer cells for immune-mediated destruction by targeting the urokinase-type plasminogen activator receptor (uPAR). Urokinase-type plasminogen activator (uPA) and uPAR are overexpressed on the surfaces of a wide range of invasive cancer cells and are believed to contribute substantially to the migratory propensities of these cells. The key component of the approach is an antibody-recruiting molecule that targets the urokinase receptor (ARM-U). This bifunctional construct is formed by selectively, covalently attaching an antibody-binding small molecule to the active site of the urokinase enzyme (uPA) to produce ARM-U2 compounds. The present inventors demonstrate that ARM-U2 is capable of redirecting antibodies to the surfaces of target cancer cells and mediating both antibody-dependent cellular phagocytosis (ADCP) and antibody-dependent cellular cytotoxicity (ADCC) against multiple human cancer cell lines. The present invention represents a novel technology has significant potential to impact the treatment of a variety of deadly, invasive cancers.

BRIEF DESCRIPTION OF THE FIGURES

FIG. 4, Scheme 1 presents a chemical scheme for synthesizing a number of ARM-U2 compounds according to the present invention. General reaction conditions are as follows: i. $NaNO_2/H2SO4$ ii. $NaN_3/H_2O$ iii. Toluene reflux iv. Methyl-3-aminobenzoate or, Dimethyl 5-aminoisophthalate, $AlCl_3/PhNO_2$ v. ABT-1, 2 or 3, DIPEA/DMF then NaOH/THF/MeOH 1:1:1 vi. 1-ABT-1, GlyOme, HATU, DIPEA/DMF, then NaOH/THF/MeOH 1:1:1 vii. 3-bromoaniline, GlyOMe, CuI, N,N-diethylsalicylamide, $K_3PO_4$/DMF viii. $AlCl_3/PhNO_2$ ix. ABT-1, DIPEA/DMF, then NaOH/THF/MeOH 1:1:1 x. metanillic acid, $DIPEA/PhNO_2$, or aniline-2,4-disulfonic acid, $Li_2CO_3$, $Cu(OAc)_2$/DMF xi. ABT-1, 2 or 3, DIPEA/DMF. Note that the (poly)ethylene glycol linkers depicted can range from 1 to 15 ethylene glycol units, often 2 to 12 ethylene glycol units, often 2 to 10 ethylene glycol units, often 3 to 9 ethylene glycol units, 3 to 8 ethylene glycol units or 3 to 7 ethylene glycol units. The diamide connector group CT depicted can also range in size as otherwise described in the present application.

FIG. 8, Table 1 shows the chemical structures of a number of representative ARM-US compounds along with their calculated uPAR binding affinity (as determined by ELISA).

FIG. 9 A/B shows the dependence of 6-ABT-1 antibody recruiting capability on cell surface uPAR illustrated using B16 melanoma cancer cells either overexpressing (A) or failing to express uPAR (C) The ADCP efficacy exhibited by 6-ABT-1 on uPAR expressing A-172 glioblastoma cells exhibiting a bell shaped dependence on 6-ABT-1 concentration characteristic of the prozone effect. Key features of this data include the significant increase in efficacy between 10 nM and 20 nM 6-ABT-1 in accordance with its low double digit nM affinity for uPAR, the ability to disrupt phagocytosis by out competition with exogenous uPAR and pyrimidine analog 6-ABT-4 and the complete loss of efficacy at 4 degrees celcius with 6-ABT-1 when phagocytosis is unable to occur D. Amnis images of complete engulfment and cellular phagocytosis of A172 cells by u937 effector cells (indicated by co-localization of two cell stains) induced by 6-ABT-1 deemed positive for phagocytosis by the ADCP flow cytometry assay shown in C at 50 nM 6-ABT-1.

FIG. 12 shows (A) Tumor growth inhibition in a B16 mouse melanoma allograft model expressing human uPAR. Tumor growth is measured over the course of several days upon treatment with PBS, doxorubicin at 1 mpk, combined doxorubicin (1 mpk)/ARM-U2 (6-ABT-1) (20 mpk) treatment, and treatment with ARM-U2 (6-ABT-1) at 20 mpk and 100 mpk in mice grafted with uPAR expressing B16 melanoma cells. (B) Kaplain-Meier curves demonstrating the prolongation of survival of mice allografted with human uPAR-positive tumors upon treatment with ARM-U2 (6-ABT-1) at both 20 mpk and 100 mpk doxrubicin, or doxorubicin/ARM-U2 combination compared to mice treated with PBS. Dox=Doxorubicin, M.S=Median Survival (days). (c) Measured weight loss associated with treatment using ARM-U2 (6-ABT-1) or doxorubicin.

FIG. 19 shows a dot-plot representation of 6-ABT-1 concentration screen (A-F) and out-competition selectivity experiments (I-VI) carried out using a flow cytometry-based dual fluorescence ADCP assay. Upper right rectangular gates represent dual positive cell events indicative of phagocytosis, Lower right rectangular gates represent target A172 cell only cell events, Ungated effector cell population present on upper right corner of dot plot. A. 10 nM 6-ABT-1 B. 20 nM 6-ABT-1 C. 50 nM 6-ABT-1 D. 100 nM 6-ABT-1 E. 1 uM 6-ABT-1 F. 10 uM 6-ABT-1 I. 20 nM 6-ABT-1 II. 20 nM 6-ABT-1+20 uM 6-ABT-4 III. 20 nM 6-ABT-1+2.1 uM uPAR IV. 50 nM 6-ABT-1 V. 50 nM 6-ABT-1+20 uM 6-ABT-4 VI. 50 nM 6-ABT-1+2.1 uM uPAR

DETAILED DESCRIPTION OF THE INVENTION

Figure 1:
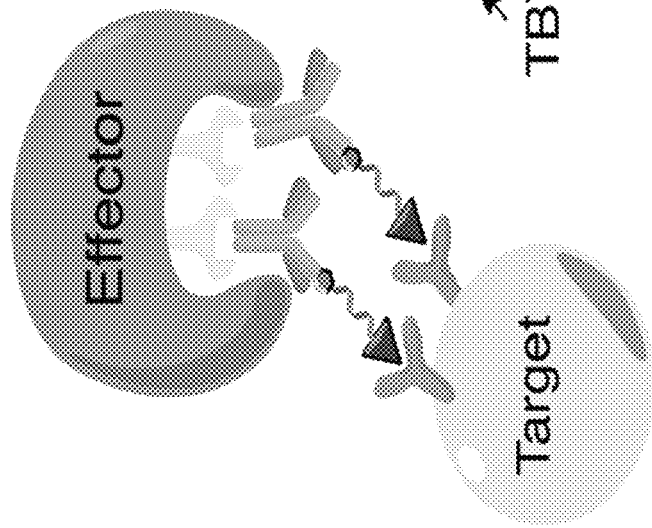
FIG. 1 shows a schematic representation of the ARM-U2 concept. In the figure, ▰ is represented as a TBT group and ▰ is represented as a ABT group.

In accordance with the present invention there may be employed conventional chemical synthetic and pharmaceutical formulation methods, as well as pharmacology, molecular biology, microbiology, and recombinant DNA techniques within the skill of the art. Such techniques are well-known and are otherwise explained fully in the literature.

Where a range of values is provided, it is understood that each intervening value, to the tenth of the unit of the lower limit unless the context clearly dictates otherwise (such as in the case of a group containing a number of carbon atoms), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It is to be noted that as used herein and in the appended claims, the singular forms "a," "an", "and" and "the" include plural references unless the context clearly dictates otherwise.

Furthermore, the following terms shall have the definitions set out below. It is understood that in the event a specific term is not defined hereinbelow, that term shall have a meaning within its typical use within context by those of ordinary skill in the art.

The term "compound", as used herein, unless otherwise indicated, refers to any specific chemical compound disclosed herein and includes tautomers, regioisomers, geometric isomers, stereoisomers and where applicable, optical isomers (enantiomers) thereof, as well as pharmaceutically acceptable salts and derivatives (including prodrug forms) thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, within context, to prodrug forms of compounds which have been modified to facilitate the administration and delivery of compounds to a site of activity. It is noted that in describing the present compounds, numerous substituents, linkers and connector molecules and variables associated with same, among others, are described. The use of a bond presented as ----- signifies that a single bond is present or absent, depending on the context of the chemistry described. The use of a bond presented as $=$ ----- signifies that a single bond or a double bond is intended depending on the context of the chemistry described. It is understood by those of ordinary skill that molecules which are described herein are stable compounds as generally described hereunder. Active compounds according to the present invention which bind to the urokinase-type plasminogen activator receptor are collectively referred to as ARM-U2 compounds, as well as difunctional compounds (even where the compounds are multifunctional).

The term "patient" or "subject" is used throughout the specification within context to describe an animal, generally a mammal and preferably a human, to whom treatment, including prophylactic treatment (prophylaxis, including especially as that term is used with respect to reducing the likelihood of metastasis of an existing cancer), with the compositions according to the present invention is provided. For treatment of those infections, conditions or disease states which are specific for a specific animal such as a human patient or a patient of a particular gender, such as a human male or female patient, the term patient refers to that specific animal. Compounds according to the present invention are useful for the treatment of cancer, including especially for use in reducing the likelihood of metastasis of a cancer.

The term "effective" is used herein, unless otherwise indicated, to describe an amount of a compound or composition which, in context, is used to produce or effect an intended result, whether that result relates to the inhibition of the effects of a disease state (e.g. cancer) on a subject or the treatment or prophylaxis of a subject for secondary conditions, disease states or manifestations of disease states as otherwise described herein. This term subsumes all other effective amount or effective concentration terms (including the term "therapeutically effective") which are otherwise described in the present application.

The terms "treat", "treating", and "treatment", etc., as used herein, refer to any action providing a benefit to a patient at risk for cancer or metastasis of cancer, including improvement in the condition through lessening or suppression of at least one symptom, inhibition of cancer growth, reduction in cancer cells or tissue, prevention, reduction in the likelihood or delay in progression of cancer or metastasis of the cancer, prevention or delay in the onset of disease states or conditions which occur secondary to cancer or remission or cure of the cancer, among others. Treatment, as used herein, encompasses both prophylactic and therapeutic treatment. The term "prophylactic" when used, means to reduce the likelihood of an occurrence or the severity of an occurrence within the context of the treatment of cancer, including cancer metastasis as otherwise described hereinabove.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors.

Neoplasms include, without limitation, morphological irregularities in cells in tissue of a subject or host, as well as pathologic proliferation of cells in tissue of a subject, as compared with normal proliferation in the same type of tissue. Additionally, neoplasms include benign tumors and malignant tumors (e.g., colon tumors) that are either invasive or noninvasive. Malignant neoplasms (cancer) are distinguished from benign neoplasms in that the former show a greater degree of anaplasia, or loss of differentiation and orientation of cells, and have the properties of invasion and metastasis. Examples of neoplasms or neoplasias from which the target cell of the present invention may be derived include, without limitation, carcinomas (e.g., squamous-cell carcinomas, adenocarcinomas, hepatocellular carcinomas, and renal cell carcinomas), particularly those of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, and melanoma); mixed types of neoplasias, particularly carcinosarcoma and Hodgkin's disease; and tumors of mixed origin, such as Wilms' tumor and teratocarcinomas (Beers and Berkow (eds.), The Merck Manual of Diagnosis and Therapy, 17.sup.th ed. (Whitehouse Station, N.J.: Merck Research Laboratories, 1999) 973-74, 976, 986, 988, 991). All of these neoplasms may be treated using compounds according to the present invention.

Representative common cancers to be treated with compounds according to the present invention include, for example, prostate cancer, metastatic prostate cancer, stomach, colon, rectal, liver, pancreatic, lung, breast, cervix uteri, corpus uteri, ovary, testis, bladder, renal, brain/CNS, head and neck, throat, Hodgkin's disease, non-Hodgkin's lymphoma, multiple myeloma, leukemia, melanoma, non-melanoma skin cancer, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer and lymphoma, among others, which may be treated by one or more compounds according to the present invention. Because of the activity of the present compounds, the present invention has general applicability treating virtually any cancer in any tissue, thus the compounds, compositions and methods of the present invention are generally applicable to the treatment of cancer and in reducing the likelihood of development of cancer and/or the metastasis of an existing cancer.

In certain particular aspects of the present invention, the cancer which is treated is metastatic cancer, a recurrent cancer or a drug resistant cancer, especially including a drug resistant cancer. Separately, metastatic cancer may be found in virtually all tissues of a cancer patient in late stages of the disease, typically metastatic cancer is found in lymph system/nodes (lymphoma), in bones, in lungs, in bladder tissue, in kidney tissue, liver tissue and in virtually any tissue, including brain (brain cancer/tumor). Thus, the present invention is generally applicable and may be used to treat any cancer in any tissue, regardless of etiology.

The term "tumor" is used to describe a malignant or benign growth or tumefacent.

The term "antibody binding moiety", "antibody binding terminus" or "antibody binding-structure" ($A_BM$ or ABT, which abbreviations are used synonymously) within the general formula of compounds according to the present invention) is used to described that portion of a bifunctional ARM-U2 compound according to the present invention which comprises at least one small molecule or hapten which can bind to antibodies within the patient. The term "hapten" is used to describe a small-molecular-weight inorganic or organic molecule that alone is not antigenic but which when linked to another molecule, such as a carrier protein (albumin, etc.) or in the case of the present invention, as an antibody terminus in the present compounds, is antigenic; and an antibody raised against the hapten (generally, the hapten bonded or complexed to the carrier) will react with the hapten alone. Because, in many instances, antihapten (especially anti-DNP) antibodies are already present in the human blood stream as endogenous antibodies because they naturally become raised to endogenous haptens (already present in patients), no pre-vaccination is necessary for ARM-U2 activity, but may optionally be used to increase the efficacy of the ARM-U2 compounds disclosed herein.

It is preferred that the antibody binding moiety comprise a hapten which is reactive with (binds to) an endogenous antibody that pre-exists in the patient prior to initiation of therapy with the compounds of the present invention and does not have to be separately raised as part of a treatment regimen (for example, by vaccination or other approach for enhancing immunogenicity), which is optionally used in the present invention. Thus, haptens which comprise a di- or trinitro phenyl group or a rhamnose group, or a digalactose hapten (Gal-Gal-Z, preferably Gal-Gal-sugar, preferably Gal-Gal-Glu), are preferred. Additionally, a compound according to the general structure:

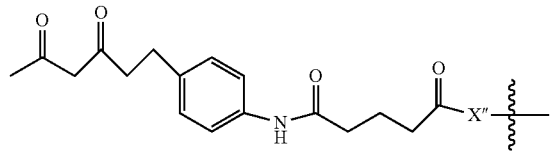

Where X″ is O, $CH_2$, $NR^1$, S; and
$R^1$ is H, a $C_1$-$C_3$ alkyl group or a —C(O)($C_1$-$C_3$) group;
May be used as haptens in the present invention.

Further, a moiety according to the chemical structure:

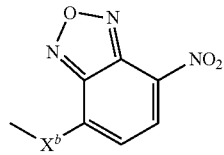

Where $X^b$ is a bond, O, $CH_2$, $NR^1$ (as above) or S may also be used as a hapten ($A_B$M) in the present invention.

A preferred $A_B$M moiety is:

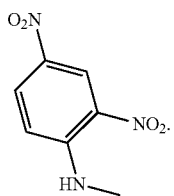

Additional $A_B$M moieties include the following:

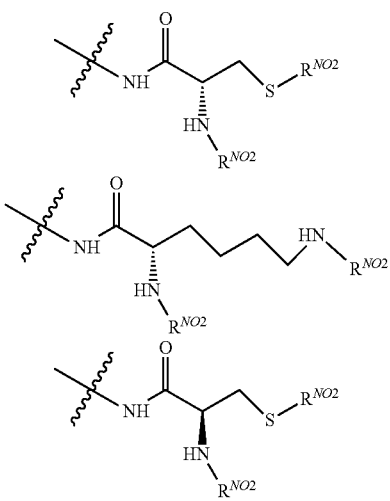

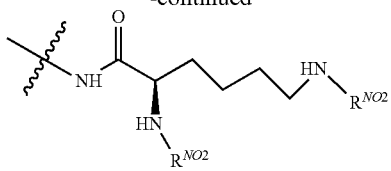

Where $R^{NO2}$ is a nitrophenyl group or a dinitrophenyl group which is bonded to the adjacent amine group or thio group as indicated;

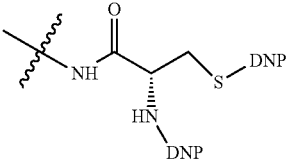

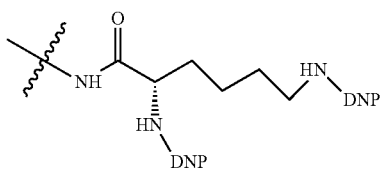

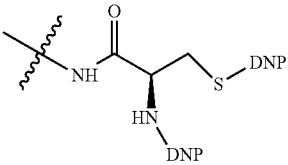

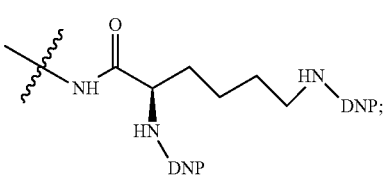

a group according to the chemical structure:

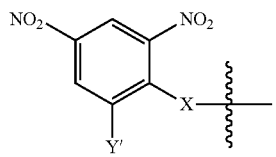

Where Y′ is H or $NO_2$ (preferably H);
X is O, $CH_2$, $NR^1$, S, S(O), $S(O)_2$, —$S(O)_2$O, —$OS(O)_2$, or $OS(O)_2$O; and
$R^1$ is H, a $C_1$-$C_3$ alkyl group, or a —C(O)($C_1$-$C_3$) group;

The fluorescein hapten ($A_B$M) moiety for use in the present invention is represented by the chemical structure (as a racemic mixture, or as either enantiomer) and may also be used as a hapten for use in the present invention:

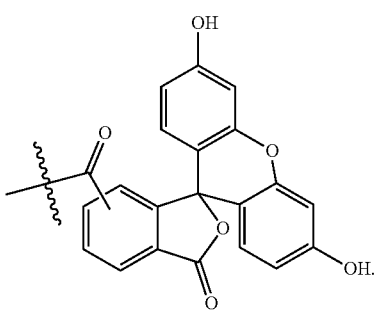

The (Gal-Gal-Z) hapten is represented by the chemical formula:

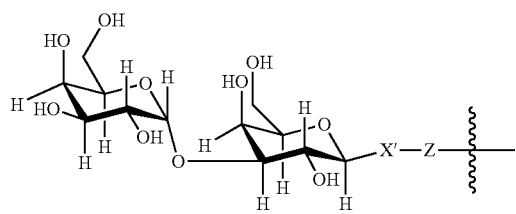

Where X' is $CH_2$, O, N—$R^{1'}$, or S, preferably O;
$R^{1'}$ is H or $C_1$-$C_3$ alkyl; and
Z is a bond, a monosaccharide, disaccharide, oligosaccharide, glycoprotein or glycolipid, preferably a sugar group, more preferably a sugar group selected from the monosaccharides, including aldoses and ketoses, and disaccharides, including those disaccharides described herein. Monosaccharide aldoses include monosaccharides such as aldotriose (D-glyceraldehdye, among others), aldotetroses (D-erythrose and D-Threose, among others), aldopentoses, (D-ribose, D-arabinose, D-xylose, D-lyxose, among others), aldohexoses (D-allose, D-altrose, D-Glucose, D-Mannose, D-gulose, D-idose, D-galactose and D-Talose, among others), and the monosaccharide ketoses include monosaccharides such as ketotriose (dihydroxyacetone, among others), ketotetrose (D-erythrulose, among others), ketopentose (D-ribulose and D-xylulose, among others), ketohexoses (D-Psicone, D-Fructose, D-Sorbose, D-Tagatose, among others), aminosugars, including galactoseamine, sialic acid, N-acetylglucosamine, among others and sulfosugars, including sulfoquinovose, among others. Exemplary disaccharides which find use in the present invention include sucrose (which may have the glucose optionally N-acetylated), lactose (which may have the galactose and/or the glucose optionally N-acetylated), maltose (which may have one or both of the glucose residues optionally N-acetylated), trehalose (which may have one or both of the glucose residues optionally N-acetylated), cellobiose (which may have one or both of the glucose residues optionally N-acetylated), kojibiose (which may have one or both of the glucose residues optionally N-acetylated), nigerose (which may have one or both of the glucose residues optionally N-acetylated), isomaltose (which may have one or both of the glucose residues optionally N-acetylated), β,β-trehalose (which may have one or both of the glucose residues optionally N-acetylated), sophorose (which may have one or both of the glucose residues optionally N-acetylated), laminaribiose (which may have one or both of the glucose residues optionally N-acetylated), gentiobiose (which may have one or both of the glucose residues optionally N-acetylated), turanose (which may have the glucose residue optionally N-acetylated), maltulose (which may have the glucose residue optionally N-acetylated), palatinose (which may have the glucose residue optionally N-acetylated), gentiobiluose (which may have the glucose residue optionally N-acetylated), mannobiose, melibiose (which may have the glucose residue and/or the galactose residue optionally N-acetylated), melibiulose (which may have the galactose residue optionally N-acetylated), rutinose, (which may have the glucose residue optionally N-acetylated), rutinulose and xylobiose, among others. Oligosaccharides for use in the present invention as Z can include any sugar of three or more (up to about 100) individual sugar (saccharide) units as described above (i.e., any one or more saccharide units described above, in any order, especially including glucose and/or galactose units as set forth above), or for example, fructo-oligosaccharides, galactooligosaccharides and mannan-oligosaccharides ranging from three to about ten-fifteen sugar units in size. Glycoproteins for use in the present invention include, for example, N-glycosylated and O-glycosylated glycoproteins, including the mucins, collagens, transferrin, ceruloplasmin, major histocompatability complex proteins (MHC), enzymes, lectins and selectins, calnexin, calreticulin, and integrin glycoprotein IIb/IIa, among others. Glycolipids for use in the present invention include, for example, glyceroglycolipids (galactolipids, sulfolipids), glycosphingolipids, such as cerebrosides, galactocerebrosides, glucocerebrosides (including glucobicaranateoets), gangliosides, globosides, sulfatides, glycophosphphingolipids and glycocalyx, among others.

Preferably, Z is a bond (linking a Gal-Gal disaccharide to a linker or connector molecule) or a glucose or glucosamine (especially N-acetylglucosamine).

It is noted that Z is linked to a galactose residue through a hydroxyl group or an amine group on the galactose of Gal-Gal, preferably a hydroxyl group. A preferred hapten is Gal-Gal-Glu which is represented by the structure:

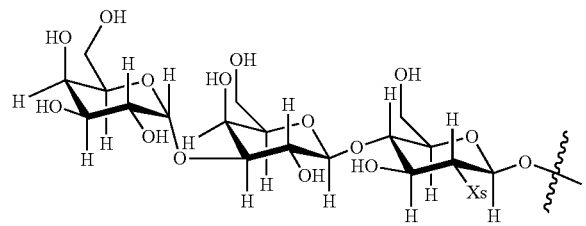

Where Xs is OH or NHAc.

Other $A_BM$ groups include, for example, the following groups:

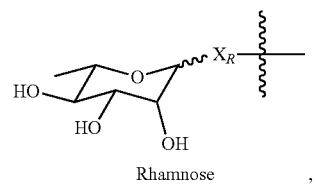

Rhamnose

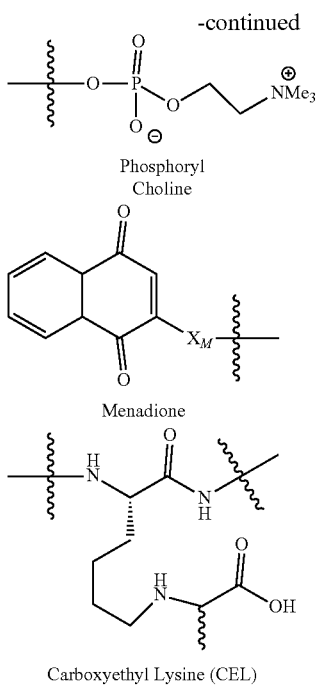

Phosphoryl Choline

Menadione

Carboxyethyl Lysine (CEL)

Where $X_R$ is O, S or $NR^1$; and
$X_M$ is O, $NR^1$ or S, and
$R^1$ is H, a $C_1$-$C_3$ alkyl group or a —C(O)($C_1$-$C_3$) group, or a pharmaceutically acceptable salt form or alternative salt form thereof.

Noted is that more than one rhamnose group (preferably from 1 to 4 rhamnose groups) may be used in the present compounds to provide enhanced antibody recruitment activity.

It is noted in the carboxyethyl lysine $A_BM$ moiety either one, two or three of the nitrogen groups may be linked to the remaining portion of the molecule through the linker or one or both of the remaining nitrogen groups may be substituted with a dinitrophenyl through an X group as otherwise described herein.

The term "urokinase-type plasminogen activator receptor", "uPAR" or simply "urokinase receptor" is used to describe a receptor which is the active site for binding of the present compounds on cancer cells pursuant to the present invention. These receptors are often overexpressed in cancer cells are known to promote invasion, migration, and metastasis in cancer cells. Accordingly, the present ARM-U2 compounds exhibit two distinguishable inhibitory actions on cancer cells. The first is to inhibit the activity of uPAR by binding to the receptor resulting in the cancer cells to which the present compounds bind having their ability to invade, migrate and metastasize inhibited. The second is to function as antibody recruitment compounds which recruit antibodies to cancer cells selectively once bound to uPAR, resulting in an antibody response to further inhibit, cause cell death and otherwise treat the cancer cells in the patient administered compounds according to the invention. uPAR is a part of the plasminogen activation system, which in a healthy, non-cancerous body is involved in tissue reorganization events such as mammary gland involution and wound healing. In order to be able to reorganize tissue, the old tissue must be able to be degraded. An important mechanism in this degradation is the proteolysis cascade initiated by the plasminogen activation system. uPAR binds urokinase and thus restricts plasminogen activation to the immediate vicinity of the cell membrane. uPAR is believed to play an important role in the regulation of this process. However, the components of the plasminogen activation system have been found to be highly expressed in many malignant tumors, indicating that tumors are able to hijack the system, and use it in metastatis. Accordingly, compounds of the present invention, at least in part, act as inhibitors of the plasminogen activation system as potent anticancer agents.

The term "urokinase-type plasminogen activator receptor binding moiety" or "$UPAR_BM$" is a moiety which binds to an active site of urokinase-type plasminogen activator receptor (uPAR) on the surface of cancer cells of a patient or subject and is used to described that portion of an ARM-U2 compound according to the present invention which comprises at least one small molecule or moiety which can bind to urokinase-type plasminogen activator receptor and can be used to produce ARM-U2 compounds hereof. The binding which occurs is competitive and maintains the compound in uPAR in order to inhibit the ability of the cancer cells to invade, migrate and/or metastasize and separately, to attract antibodies to those same cancer cells.

Preferred $UPAR_BM$ groups for use in the present invention are set forth below. In one embodiment, the $UPAR_BM$ group is a moiety (or its enantiomer with the acyl group of the amide being disposed upwards rather than downward from the plane as depicted) according to the chemical structure:

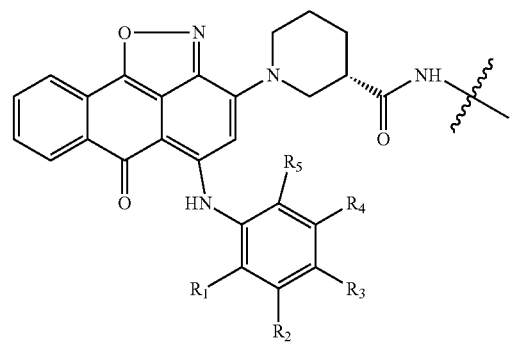

where $R_1$, $R_2$, $R_3$, $R_4$ and $R_5$ are each independently H, a halogen (F, Cl, Br, I, preferably F), a $C_1$-$C_3$ alkyl group optionally substituted with one or two hydroxyl groups or up to three fluoro groups, a $(CH_2)_m COOH$ group, a $(CH_2)_m SO_3H$ group, or

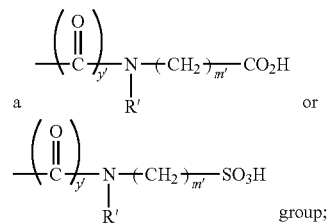

group;

Each R' is independently H or a $C_1$-$C_3$ alkyl group (preferably H or $CH_3$, most often H);
m' is 0, 1, 2 or 3 (preferably 0 in the case of the sulfonic acid or 1 in the case of the carboxylic acid); and
y' is 0, 1 or 2 (preferably 0 or 1.

Alternatively, preferred UPAR$_B$M groups ((or its enantiomer with the acyl group of the amide being disposed upwards rather than downward from the plane as depicted)) are directed to the following groups:

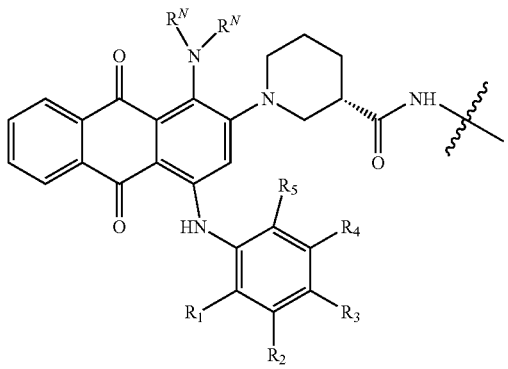

Wherein each R$^N$ is independently H or a C$_1$-C$_3$ alkyl group;
R$_1$, R$_2$, R$_3$, R$_4$ and R$_5$ are each independently H, a halogen (F, Cl, Br, I, preferably F),
a C$_1$-C$_3$ alkyl group optionally substituted with one or two hydroxyl groups or up to three fluoro groups, a (CH$_2$)$_m$COOH group, a (CH$_2$)$_m$SO$_3$H group, or

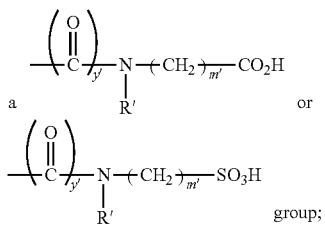

Each R' is independently H or a C$_1$-C$_3$ alkyl group (preferably H or CH$_3$, most often H);
m' is 0, 1, 2 or 3 (preferably 0 in the case of the sulfonic acid or 1 in the case of the carboxylic acid); and
y' is 0, 1 or 2 (preferably 0 or 1).
The UPAR$_B$M groups are attached through the indicated amine group to a R$^{LABT}$ group.

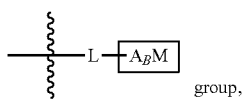

group,

The R$^{LABT}$ group is represented as an group,
where L is a bond, at least one linker (preferably a single linker) which comprises a first linker group L1 which optionally includes a connector group CT and an optional linker group L2 which itself optionally includes a connector group CT, said first linker group L1 being linked to said second linker group L2 optionally (preferably) through a CT group; and
[A$_B$M] is an antibody bonding moiety comprising a hapten which is capable of binding to an antibody in said patient or subject as otherwise described herein. The ARM-U2 compounds according to the present invention may be a pharmaceutically acceptable salt, solvate or polymorph thereof.

In preferred embodiments of the invention, R$_1$ is H or SO$_3$H, R$_2$ is H, CO$_2$H, SO$_3$H, —NHCH$_2$—CO$_2$H or —C(O)—NHCH$_2$—CO$_2$H, R$_3$ is H or SO$_3$H and R$_4$ is H or CO$_2$H, or a pharmaceutically acceptable salt or solvate thereof.

The term "pharmaceutically acceptable salt" is used throughout the specification to describe a salt form of one or more of the compounds herein which are presented to increase the solubility of the compound in saline for parenteral delivery or in the gastric juices of the patient's gastrointestinal tract in order to promote dissolution and the bioavailability of the compounds. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art. Sodium and potassium salts may be particularly preferred as neutralization salts of carboxylic acid containing compositions according to the present invention. The term "salt" shall mean any salt consistent with the use of the compounds according to the present invention. In the case where the compounds are used in pharmaceutical indications, including the treatment of HIV infections, the term "salt" shall mean a pharmaceutically acceptable salt, consistent with the use of the compounds as pharmaceutical agents.

The term "linker", "L1" or "L2" refers to a chemical entity connecting an antibody binding (A$_B$M) moiety to a urokinase-like plasminogen activator receptor binding moiety (UPAR$_B$M), optionally through at least one (preferably one) connector moiety (CT) through covalent bonds. The linker between the two active portions of the molecule, that is the antibody binding moiety (A$_B$M) and the urokinase binding moiety (UPAR$_B$M) ranges from about 5 Å to about 50 Å or more in length, about 6 Å to about 45 Å in length, about 7 Å to about 40 Å in length, about 8 Å to about 35 Å in length, about 9 Å to about 30 Å in length, about 10 Å to about 25 Å in length, about 7 Å to about 20 Å in length, about 5 Å to about 16 Å in length, about 5 Å to about 15 Å in length, about 6 Å to about 14 Å in length, about 10 Å to about 20 Å in length, about 11 Å to about 25 Å in length, etc. Linkers which are based upon ethylene glycol units and are between 2 and 15 glycol units, 1 and 8 glycol units, 1, 2, 3, 4, 5, and 6 glycol units in length may be preferred. By having a linker with a length as otherwise disclosed herein, the A$_B$M moiety and the UPAR$_B$M moiety may be situated to advantageously take advantage of the biological activity of compounds according to the present invention which bind to urokinase-like plasminogen activator on cancer cells, including cancer cells prone to metastasis and attract endogenous antibodies to those cells to which the compounds are bound, resulting in the selective and targeted death of those cells. The selection of a linker component is based on its documented properties of biocompatibility, solubility in aqueous and organic media, and low immunogenicity/antigenicity. Although numerous linkers may be used as otherwise described herein, a linker based upon polyethyleneglycol (PEG) linkages, polypropylene glycol linkages, or polyethyleneglycol-co-polypropylene oligomers (up to about 100 units, about 1 to 100, about 1 to 75, about 1 to 60, about 1 to 50, about 1 to 35, about 1 to 25, about 1 to 20, about 1 to 15, 2 to 10, about 4 to 12, about 1 to 8, 1 to 3, 1 to 4, 2 to 6, 1 to 5, etc.) may be favored as a linker because of the chemical and biological characteristics of these molecules. The use of polyethylene (PEG) linkages is preferred. When describing linkers according to the present invention, including polyethylene glycol linkers or other linkers, one or more additional groups (e.g., methylene groups, amide groups, etc., methylene groups are preferred) may be covalently attached at either end of the linker group to attach to a UPAR$_B$M group, a CT group, another linker group or an A$_B$M group.

Alternative linkers may include, for example, polyamino acid linkers of up to 100 amino acids (of any type, preferably D- or L-amino acids, preferably naturally occurring L-amino acids) in length (m is about 1 to 100, about 1 to 75, about 1 to 60, about 1 to 50, about 1 to 45, about 1 to 35, about 1 to 25, about 1 to 20, about 1 to 15, 2 to 10, about 4 to 12, about 5 to 10, about 4 to 6, about 1 to 8, about 1 to 6, about 1 to 5, about 1 to 4, about 1 to 3, etc.), optionally including one or two connecting groups (preferably at one or both ends of the polyamino acid linker).

Preferred linkers include those according to the chemical structures:

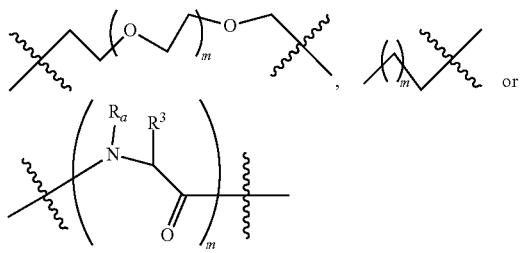

Or a polypropylene glycol or polypropylene-co-polyethylene glycol linker having between 1 and 100 alkylene glycol units;

Where R$_a$ is H, C$_1$-C$_3$ alkyl or alkanol or forms a cyclic ring with R$^3$ (proline) and R$^3$ is a side chain derived from a D- or L amino acid (preferably a naturally occurring L-amino acid) preferably selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methyleneimidazole), isoleucine (1-methylpropane), leucine (2-methylpropane), lysine (butyleneamine), methionine (ethylmethylthioether), phenylalanine (benzyl), proline (R$^3$ forms a cyclic ring with R$_a$ and the adjacent nitrogen group to form a pyrrolidine group), hydroxyproline, serine (methanol), threonine (ethanol, 1-hydroxyethane), tryptophan (methyleneindole), tyrosine (methylene phenol) or valine (isopropyl);

m (within the context of this use) is an integer from 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

n (within the context of this use) is an integer from about 1 to 100, about 1 to 75, about 1 to 60, about 1 to 50, about 1 to 45, about 1 to 35, about 1 to 25, about 1 to 20, about 1 to 15, 2 to 10, about 4 to 12, about 5 to 10, about 4 to 6, about 1 to 8, about 1 to 6, about 1 to 5, about 1 to 4, about 1 to 3, etc.) or Another linker according to the present invention comprises a polyethylene glycol linker containing from 1 to 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5 ethylene glycol units, to which is bonded a lysine group (preferably at its carboxylic acid moiety) which binds one or two DNP groups to the lysine at the amino group(s) of lysine. Still other linkers comprise amino acid residues (D or L) to which are bonded to A$_B$M moieties, in particular, DNP, among others at various places on amino acid residue as otherwise described herein. In another embodiment, as otherwise described herein, the amino acid has anywhere from 1-15 methylene groups separating the amino group from the acid group in providing a linker to the A$_B$M moiety.

Or another linker is according to the chemical formula:

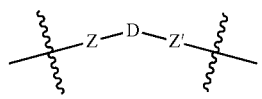

Where Z and Z' are each independently a bond, —(CH$_2$)$_i$—O, —(CH$_2$)$_i$—S, —(CH$_2$)$_i$—N—R,

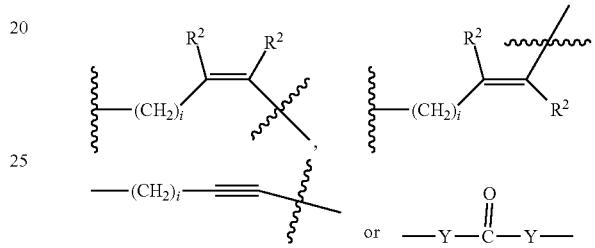

wherein said —(CH$_2$)$_i$ group, if present in Z or Z', is bonded to a connector (CT), A$_B$M and/or U$_k$BM;

Each R is H, or a C$_1$-C$_3$ alkyl or alkanol group;
Each R$^2$ is independently H or a C$_1$-C$_3$ alkyl group;
Each Y is independently a bond, O, S or N—R;
Each i is independently 0 to 100, 0 to 75, 1 to 60, 1 to 55, 1 to 50, 1 to 45, 1 to 40, 2 to 35, 3 to 30, 1 to 15, 1 to 10, 1 to 8, 1 to 6, 0, 1, 2, 3, 4 or 5;
D is

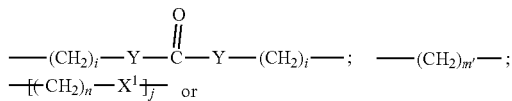

a bond, with the proviso that Z, Z' and D are not each simultaneously bonds;

j is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

m' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

n is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5 (n is preferably 2);

X$^1$ is O, S or N—R; and
R is as described above, or a pharmaceutical salt thereof.

Other linkers which are included herein include preferred linkers according to the chemical structure:

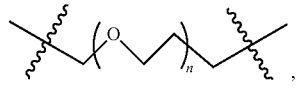

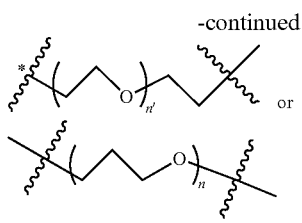 or where each n and n' is independently 1 to 25, 1 to 15, 1 to 12, 2 to 11, 2 to 10, 2 to 8, 2 to 6, 2 to 5, 2 to 4 and 2 to 3 or 1, 2, 3, 4, 5, 6, 7, or 8; and each n" is independently 0 to 8, often 1 to 7, or 1, 2, 3, 4, 5 or 6 (preferably 3).

Preferred linkers which include a CT group (especially a diamide CT group as otherwise described herein) connecting a first and second (PEG) linker group include the following structures:

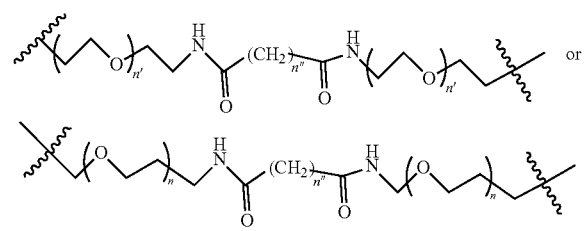

where each n and n' is independently 1 to 25, 1 to 15, 1 to 12, 2 to 11, 2 to 10, 2 to 8, 2 to 6, 2 to 5, 2 to 4 and 2 to 3 or 1, 2, 3, 4, 5, 6, 7, or 8; and each n" is independently 0 to 8, often 1 to 7, or 1, 2, 3, 4, 5 or 6 (preferably 3). Noted is that each of these linkers may contain alkylene groups containing from 1 to 4 methylene groups at the distal ends of each linker group in order to facilitate connection of the linker group.

The term "connector", symbolized in the generic formulas by (CT), is used to describe a chemical moiety which is optionally included in bifunctional compounds according to the present invention which forms from the reaction product of an activated $A_BM$-linker with a $U_kBM$ moiety (which also is preferably activated) or an $A_BM$ moiety with an activated linker-$U_kBM$ as otherwise described herein. The connector group is often the resulting moiety which forms from the facile condensation of two or more separate chemical fragments which contain reactive groups which can provide connector groups as otherwise described to produce bifunctional or multifunctional compounds according to the present invention. It is noted that a connector may be distinguishable from a linker in that the connector is the result of a specific chemistry which is used to provide bifunctional compounds according to the present invention wherein the reaction product of these groups results in an identifiable connector group or part of a connector group which is distinguishable from the linker group, although in certain instances, the connector group is incorporated into and integral with the linker group as otherwise described herein. It is noted also that a connector group may be linked to a number of linkers to provide multifunctionality (i.e., more than one $U_kBM$ moiety and/or more than one $A_BM$ moiety within the same molecule. It is noted that there may be some overlap between the description of the connector group and the linker group such that the connector group is actually incorporated or forms part of the linker, especially with respect to more common connector groups such as amide groups, oxygen (ether), sulfur (thioether) or amine linkages, urea or carbonate —OC(O)O— groups as otherwise described herein. It is further noted that a connector (or linker) may be connected to $A_BM$, a linker or $U_kBM$ at positions which are represented as being linked to another group using the symbol

Where two or more such groups are present in a linker or connector, any of an $A_BM$, a linker or a $U_kBM$ may be bonded to such a group. Where that symbol is not used, the linker may be at one or more positions of a moiety.

Common connector groups which are used in the present invention include the following chemical groups:

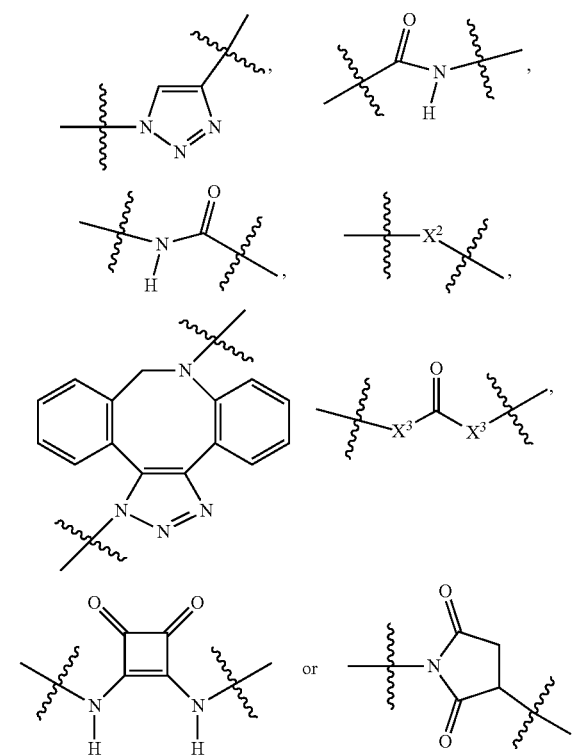

or a diamide group according to the structure:

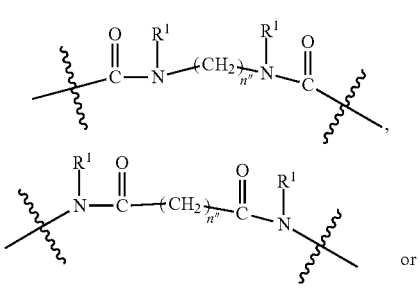

or

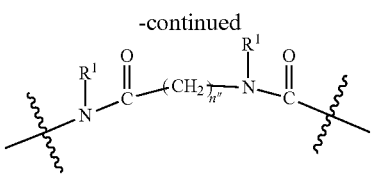

Where $X^2$ is $CH_2$, O, S, $NR^4$, C(O), S(O), $S(O)_2$, —$S(O)_2O$, —$OS(O)_2$, or $OS(O)_2O$;

$X^3$ is O, S, $NR^4$;

$R^4$ is H, a $C_1$-$C_3$ alkyl or alkanol group, or a —C(O)($C_1$-$C_3$) group;

$R^1$ is H or a $C_1$-$C_3$ alkyl group (preferably H); and n" is independently 0 to 8, often 1 to 7, or 1, 2, 3, 4, 5 or 6 (preferably 3). The triazole group, indicated above, is a preferred connector group. It is noted that each connector may be extended with one or more methylene groups to facilitate connection to a linker group, another CT group, a UPAR$_B$M group or a A$_B$M group. It is noted that in certain instances, within context the diamide group may also function independently as a linker group.

It is noted that each of the above groups may be further linked to a chemical moiety which bonds two or more of the above connector groups into a multifunctional connector, thus providing complex multifunctional compounds comprising more than one A$_B$M and/or UPAR$_B$M group and a number of linker groups within the multifunctional compound.

The term "alkyl" refers to a fully saturated monovalent radical containing carbon and hydrogen, and which may be cyclic, branched or a straight chain containing from 1 to 10 carbon atoms, (1, 2, 3, 4, 5, 6, 7, 8, 9 or 10), preferably 1, 2 or 3 carbon atoms. Examples of alkyl groups are methyl, ethyl, n-butyl, n-hexyl, n-heptyl, n-octyl, isopropyl, 2-methylpropyl, cyclopropyl, cyclopropylmethyl, cyclobutyl, cyclopentyl, cyclopen-tylethyl, cyclohexylethyl and cyclohexyl. Preferred alkyl groups are $C_1$-$C_6$ or $C_1$-$C_3$ alkyl groups. "Alkylene" (e.g., methylene) when used, refers to a fully saturated hydrocarbon which is divalent (may be linear, branched or cyclic) and which is optionally substituted. Other terms used to indicate substituent groups in compounds according to the present invention are as conventionally used in the art.

The term "coadministration" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, provided that effective concentrations of all coadministered compounds or compositions are found in the subject at a given time. ARM-U2 compounds according to the present invention may be administered with one or more additional anti-cancer agents or other agents which are used to treat or ameliorate the symptoms of cancer, especially including metastatic cancer. Exemplary anticancer agents which may be coadministered in combination with one or more chimeric compounds according to the present invention include, for example, antimetabolites, inhibitors of topoisomerase I and/or II, alkylating agents and microtubule inhibitors (e.g., taxol), among numerous others, as otherwise described herein.

The term "additional anti-cancer agent" refers to one or more traditional cancer agent(s) which may be co-adminis- tered with compounds according to the present invention in the treatment of cancer. These agents include chemotherapeutic agents and include one or more members selected from the group consisting of everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl) ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolylj-quinolone, vatalanib, AG-013736, AVE-0005, the acetate salt of [D-Ser(But) 6, Azgly 10](pyro-Glu-His-Trp-Ser-Tyr-D-Ser(But)-Leu-Arg-Pro-Azgly-NH$_2$ acetate [$C_{59}H_{84}N_{18}Oi_4$-$(C_2H_4O_2)_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa, ipilimumab, nivolomuab, pembrolizumab, dabrafenib, trametinib vemurafenib among others.

Pharmaceutical compositions according to the present invention comprise an effective amount of at least one ARM-U2 compound as otherwise described herein, in combination with a pharmaceutically effective amount of a carrier, additive or excipient, optionally, in combination with one or more of the additional agents, especially anti-cancer agents, otherwise described herein, all in effective amounts.

The ARM-U2 containing pharmaceutical compositions of the present invention may be formulated in a conventional manner using one or more pharmaceutically acceptable carriers and may also be administered in immediate, early release or controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. In certain preferred aspects of the invention, the topical cream or lotion may be used prophylatically to prevent infection when applied topically in areas prone toward virus infection. In additional aspects, the compounds according to the present invention may be coated onto the inner surface of a condom and utilized to reduce the likelihood of infection during sexual activity.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition of the instant invention that may be combined with the carrier materials to produce a single dosage form will vary depending upon the host and disease treated, the particular mode of administration. Preferably, the compositions should be formulated to contain between about 0.05 milligram to about 1 to several grams, more preferably about 1 milligram to about 750 milligrams, and even more preferably about 10 milligrams to about 500-600 milligrams of active ingredient, alone or in combination with at least one other ARM-U2 compound according to the present invention or other anticancer agent which may be used to treat cancer or a secondary effect or condition thereof.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject (e.g. a male or female human) suffering from cancer can be treated by administering to the patient (subject) an effective amount of the ARM-U2 compound according to the present invention including pharmaceutically acceptable salts, solvates or polymorphs, thereof optionally in a pharmaceutically acceptable carrier or diluent, either alone, or in combination with other known pharmaceutical agents, preferably agents which can assist in treating cancer and/or secondary effects of cancer or ameliorate the secondary effects and conditions associated with cancer, including metastasis of cancer. This treatment can also be administered in conjunction with other conventional cancer therapies, including radiation therapy.

These compounds can be administered by any appropriate route, for example, orally, parenterally, intravenously, intradermally, subcutaneously, or topically, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably about 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to one containing less than 1 mg, 1 mg to 3000 mg, preferably about 5 to 500-600 mg or more of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 $\mu$M. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as other anticancer agent, anti-HIV agents, antibiotics, antifungals, anti-inflammatories, or antiviral compounds. In certain preferred aspects of the invention, one or more ARM-U2 compounds according to the present invention are coadministered with another anticancer agent and/or another bioactive agent, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

General Chemical Synthesis

Figure 5:
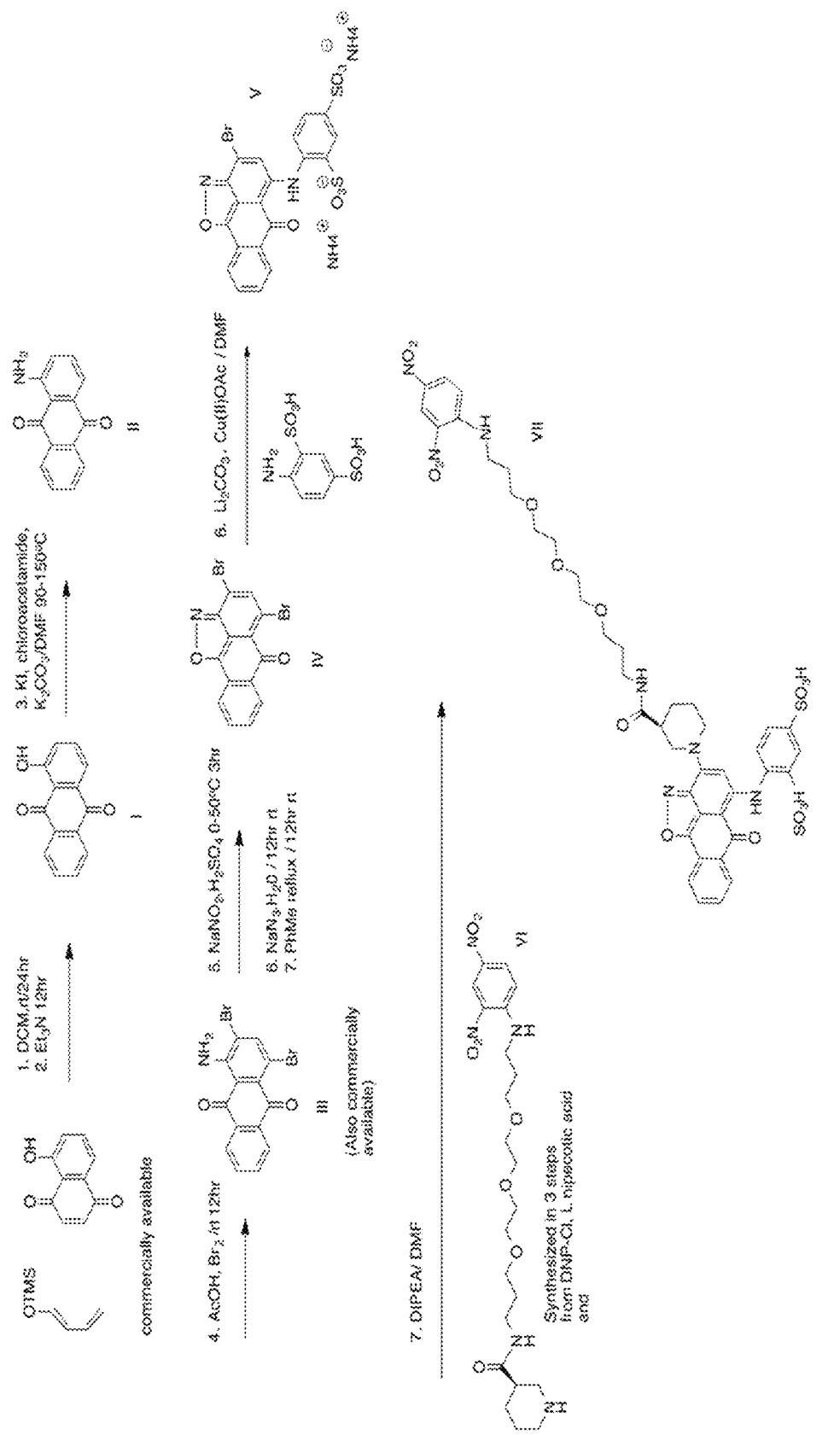
FIG. 5 shows the synthesis of a representative compound according to the present invention.
Figure 6:
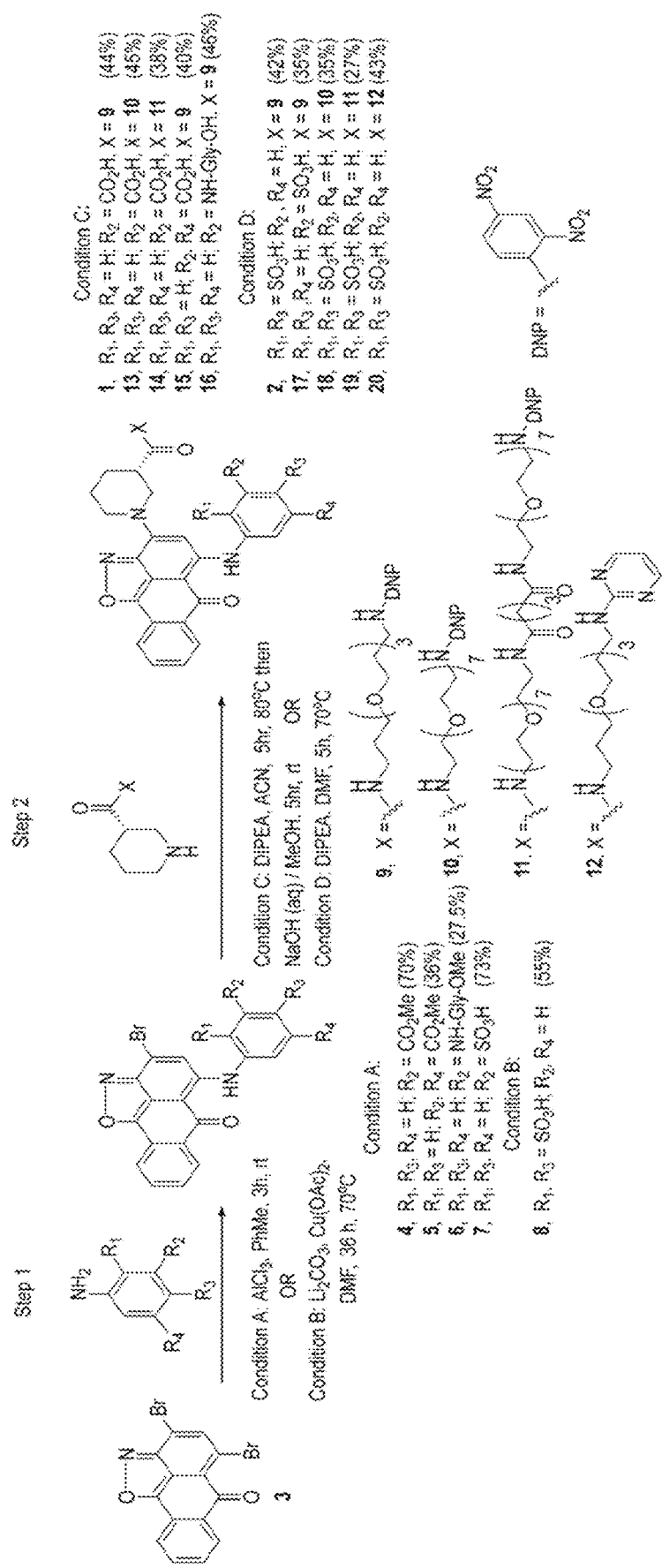
FIG. 6 shows a chemical synthetic scheme for a number of compounds according to the present invention.
Figure 7:
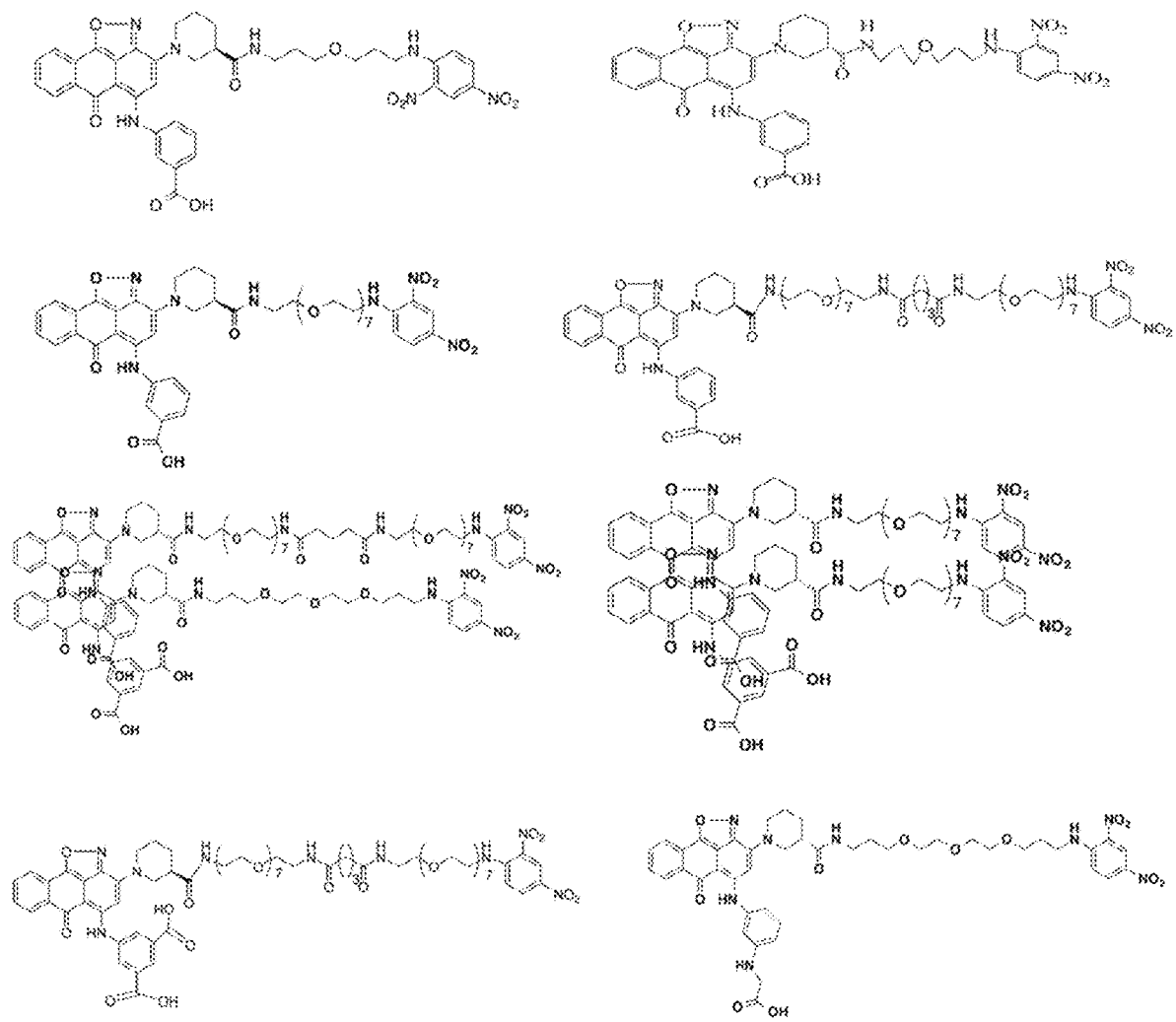
FIG. 7 shows a number of representative compounds according to the present invention. Note that for each of these compounds, the isoxazole compounds are shown. Alternatively, these compounds may be readily converted to the ring-opened compounds (containing a keto group and amine group in place of the isoxazole group). See the examples section of the present application. Not all enantiomers are shown.
Figure 7:
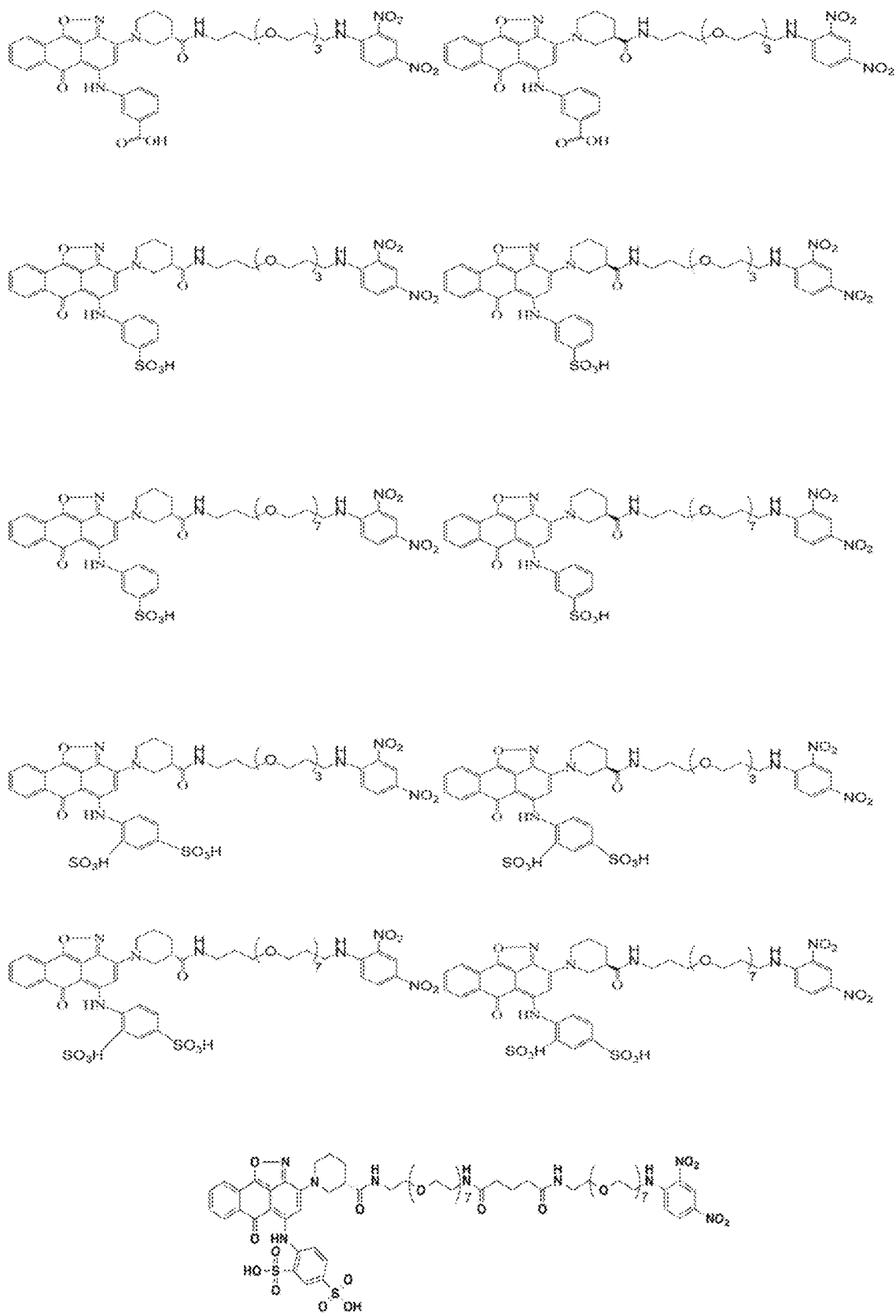
Figure 7:
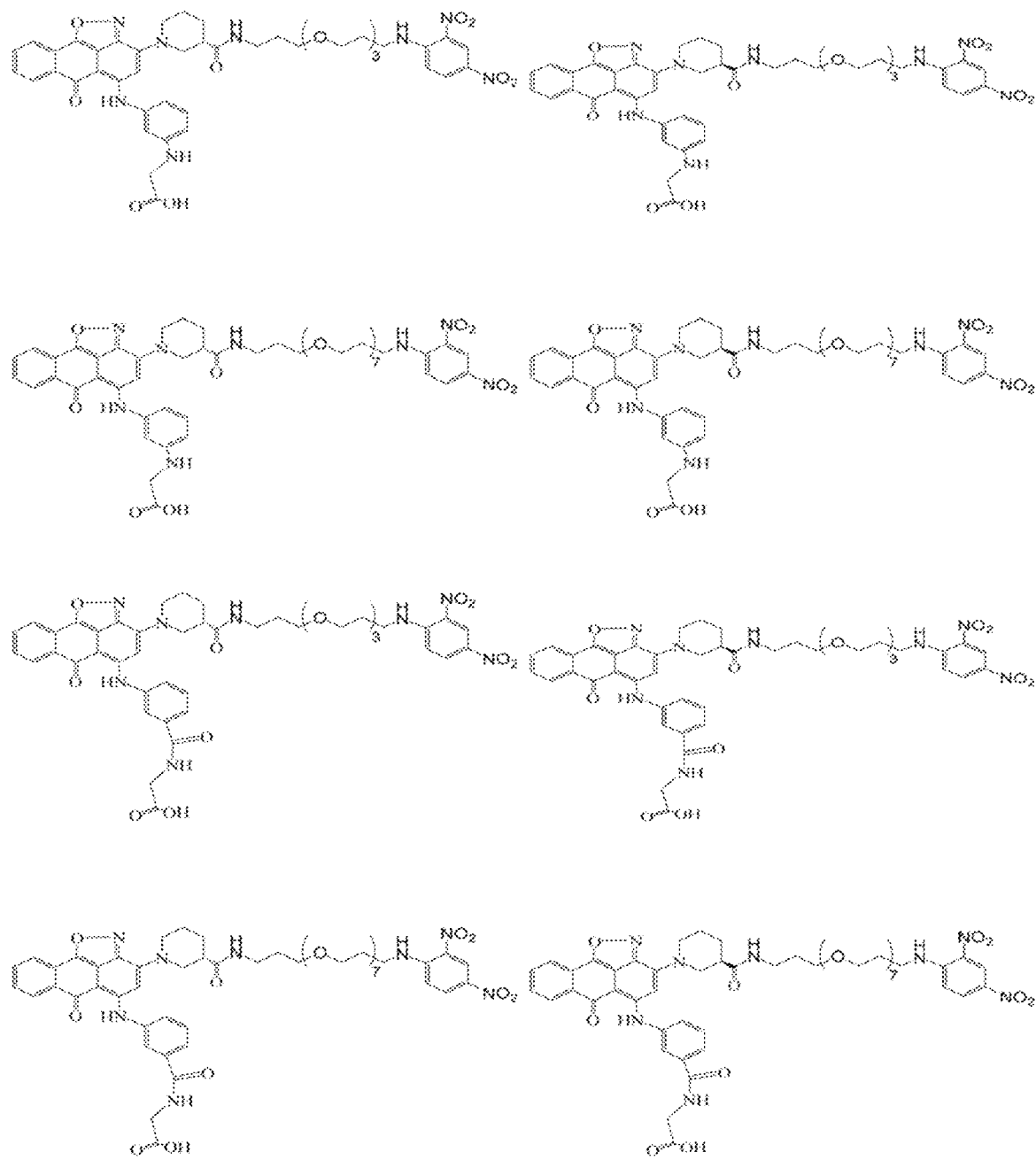

All ARM U2 derivatives may be synthesized by performing a highly general, optimized nucleophillic substitution/deprotection reaction sequence carried out between the ABT variant of choice and a mono-bromoisoxazole-anthroquinone core intermediate consisting of various functionalized aniline derivatives all substituted at position 4 of ring C (See FIG. 4, Scheme 1, FIG. 5, FIG. 6, FIG. 8, Table 1 and the examples section of the present application). Isoxazole formation is critical for the substitution of nucleophillic substituents at positions 2 and 4 of ring C by disrupting ring C aromaticity affording a higher degree of 1.4 michael acceptor character in ring C. Other compounds which are disclosed are synthesized by analogy using standard methods which are readily available in the art. It is noted that the isoxazole group may be readily cleaved to the corresponding keto and free amine functionality in certain compounds according to the present invention by exposing the compound to light or aqueous conditions (described hereinbelow). These compounds, readily prepared, are also biologically active.

The $A_B$Ms (see FIG. 4, scheme 1 and the examples section) employed in this study were synthesized from commercially available polyethylene glycol (PEG) derivatives of varying lengths, tethered to DNP on one terminus and terminating in an L- or D-nipecotic amide residue serving as the nucleophile in the substitution reaction. Other linkers may be readily substituted for the PEG linkers as otherwise described herein. Preceding the mono-bromoisoxazole core intermediate III (SI) in the synthetic pathway (FIG. 4, Scheme 1) is a di-brominated isoxazole-anthroquinone intermediate II (FIG. 4, Scheme 1) central to the synthesis of all ARM-U2 derivatives synthesized which was subsequently functionalized with various aniline derivatives through selective lewis acid or metal mediated couplings to yield the respective ARM-U2 derivative prior to the ABT substitution step.

Coupling the dibrominated isoxazole core with 3-aminobenzoate using aluminum trichloride facilitates selective coupling of the aniline derivative at the 4-position over the 2-position of ring C and afforded the key intermediate to access derivatives 1-ABT-1 and 1-D-ABT-1 differing in the stereochemistry of the appended ABT. The di-acid derivative 2-ABT-1 could be efficiently accessed via aluminum chloride mediated coupling of aniline dibenzoate to intermediate II. ARM U2 derivative 3-ABT-1 was efficiently accessed through facile coupling of ester-protected glycine to derivative 1-ABT-1. Derivative 4-ABT-1 with the carboxyl extended farther from the aniline moiety was successfully synthesized via a novel application of a modified Ullman-type copper coupling reaction between methylester protected glycine and 3-bromoaniline. Other amino acids may be used in place of the glycine with appropriate protection groups being used.

The resulting glycine functionalized aniline could be coupled selectively to position 4 of intermediate II again by employing Lewis acid catalysis with aluminum chloride The mono-meta sulfonate derivative 5-ABT-1 was afforded via an adapted aluminum chloride mediate coupling procedure linking metanilic acid to the 4-position of ring C of intermediate II. Solubilization of metanilic acid with careful control of DIPEA equivalents proved critical for a high yielding reaction. The di-sulfonate derivative 6-ABT-1 was synthesized by a highly optimized $Li_2CO_3$ mediated, Cu(II) OAc catalyzed coupling reaction between aniline-2,4-disulfonic acid and intermediate II. Aluminum trichloride mediates coupling of the sulfonated aniline was unsuccessful likely due to deactivation of the aniline by ortho and para sulfonates as well as potential sulfaonte chelation to the catalyst. The reaction proved highly sensitive to temperature, organic bases, copper II equivalents and requires a large excess of the aniline for conversion to product however achieves selective coupling for the 4-position over the 2-position of ring C.

Longer ABT containing ARM-U2 derivatives 1-ABT-2, 1-ABT-3, 2-ABT-2 6-ABT-2 and 6-ABT-3 were also synthesized using identical chemistry as their shorter linker ABT-1 counterparts only differing in the incorporation of longer PEG-derived spacer units Control ARM-U2 derivative 6-ABT-4 lacking antibody recruiting capability due to a DNP to pyrimidine substitution was synthesized as described above for 6-ABT-1 only incorporating an additional copper catalyzed coupling step to install the pyrimidine unit onto the linker.

Each of the ARM-U2 derivatives proposed by docking studies were synthesized initially on a ten milligram scale and can be successfully scaled up to 0.5 g. Each derivative was purified by HPLC as the final purification step using formic acid buffers or in the special case of 6-ABT-1/2/3 using ammonium formate buffers and were successfully characterized by proton and carbon NMR and high resolution ESI/MS.

The scheme set forth in FIG. 5 hereof sets forth the synthesis of compound ARM-US 0040, a preferred compound. Formation of tricyclic compound 1 proceeds by reacting the commercially available diene with the bicyclic dione compound. The hydroxyl group of compound I is converted to an amine group to form compound II, which is subsequently reacted to form the dibromo derivative III. The amine and keto group is cyclized to form the dibromo isoxazole compound IV which is then reacted with the di-sulfonic acid aniline intermediate to form compound V. Compound V is then condensed with the piperidine linked dinitrophenol functional linking group, displacing the bromo substituent to form the final ARM-U2 0040 compound.

Other compounds which are described in the present application are readily synthesized by modifying the synthetic steps which are described above or made by analogy following routing synthetic chemical synthetic steps well known in the arts.

In the case of ring opened compounds (where the isoxazole moiety is ring-opened and replaced by a keto group and amine group as set forth herein) as described in the present invention, the preferred approach for opening the isoxazole ring is to expose the isoxazole compound in solvent to light at room temperature or in certain instances, elevated temperature, or alternatively, the compound may be dissolved in an aqueous solvent to provide an aqueous solution which can be stirred at room temperature or reduced or elevated temperature in order to reduce to increase the formation of the ring-opened compound. The ring-opened compounds exhibit biological activity similar to the isoxazole compounds in the nanomolar to micromolar range. The following examples are described in order to provide specific chemical synthetic procedures and/or biological activities.

EXAMPLES

The following chemical examples are provided. Methodology and data related to chemistry and biology is included here and/or in the attached Appendices A and/or B.

General Information

Synthesis: All reagents were purchased from commercial suppliers and used without further purification except the following: triethylamine was distilled over calcium hydride; $CH_2Cl_2$, PhMe, DMF, and THF were purified using a solvent dispensing system;[1] Water was purified using a Milli-Q purification system. Infrared (IR) spectra bands are characterized as broad (br), strong (s), medium (m) and weak (w). $^1H$ NMR chemical shifts are reported with the solvent residual peak as the internal standard ($CDCl_3$ 7.26 ppm or DMSO 3.31 ppm). Data are reported as follows: chemical shift, integration, multiplicity (s=singlet, d=doublet, t=triplet, q=quartet, br=broad, m=multiplet), and coupling constants (Hz). $^{13}C$ NMR chemical shifts are reported in ppm with the solvent as an internal reference ($CDCl_3$ 77.2 ppm or $CD_3OD$ 49.00 ppm or d-DMSO 39.5 ppm). Polyethylene glycol linker-based derivatives $(C_2H_2O)_nH$ were synthesized from the corresponding polyethylene glycol of the highest oligomer purity commercially available through Aldrich (all cases >90% major oligomer).

Biology: A172 human glioblastoma cells were purchased from ATCC (# CRL-1620), grown in T-flasks with Dulbecco's modified Eagle's medium supplemented with 10% HI-FBS, and detached by the EDTA detachment procedure. U937 Cells were purchased from ATCC (# CRL-1593.2), grown in Petri dishes as a suspension with RPMI-1640 medium supplemented with 10% HI-FBS and 1% penicillin-streptomycin. All cell culturing was done using colored ADCP Media RPMI Medium 1640, liquid Invitrogen #11875-093 supplemented with 10% HI-FBS and 1% penicillin-streptomycin. Anti-Dinitrophenyl-KLH Rabbit IgG Fraction with and without biotin were purchased from Invitrogen # A6430 (Lot 807872) as a solution and stored at 4° C. Human uPAR Antibody: Polyclonal goat IgG R&D Systems # AF807 was purchased as a lyophilized solid and was stored at −20° C., as a solution in 250 µL of sterile DPBS. Human urokinase, isolated from human urine was purchased from PROSPEC as a lyophilized white solid and reconstituted at a concentration of 1 mg/ml (approx. 18.5 uM) in milliQ water and stored at −20° C. Recombinant human uPAR with carrier protein was obtained as a white lyophilized solid from R&D systems and dissolved in DPBS at a concentration of 100 ug/ml (approx. 2 uM) and stored at −20° C.

Synthesis

Scheme S1. A. Novel synthesis of dibromoanthroquinone starting material B. Synthesis of ARM-U2 derivatives 1-ABT-1 and 1-(D)-ABT-1

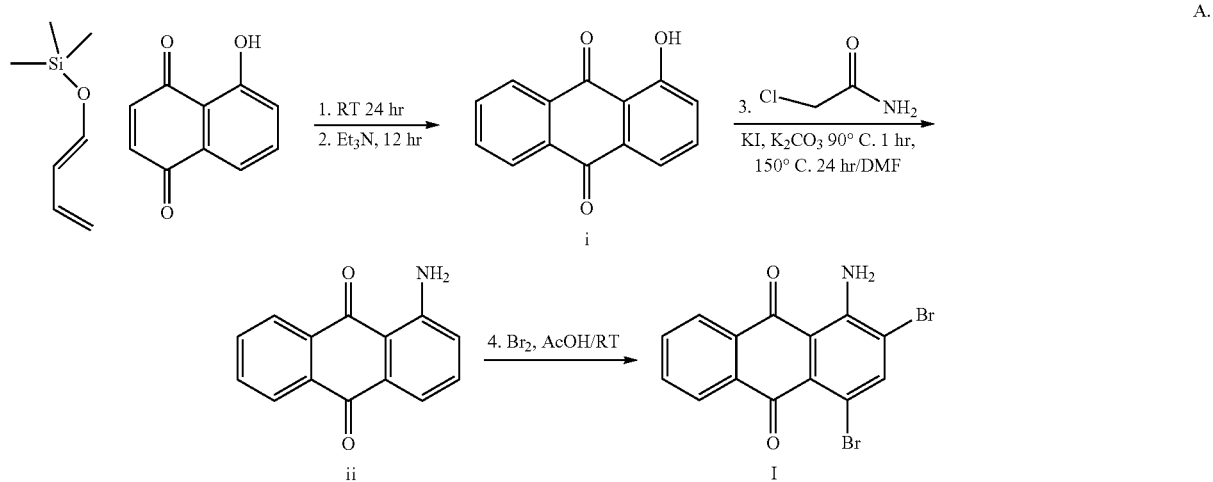

A.

-continued

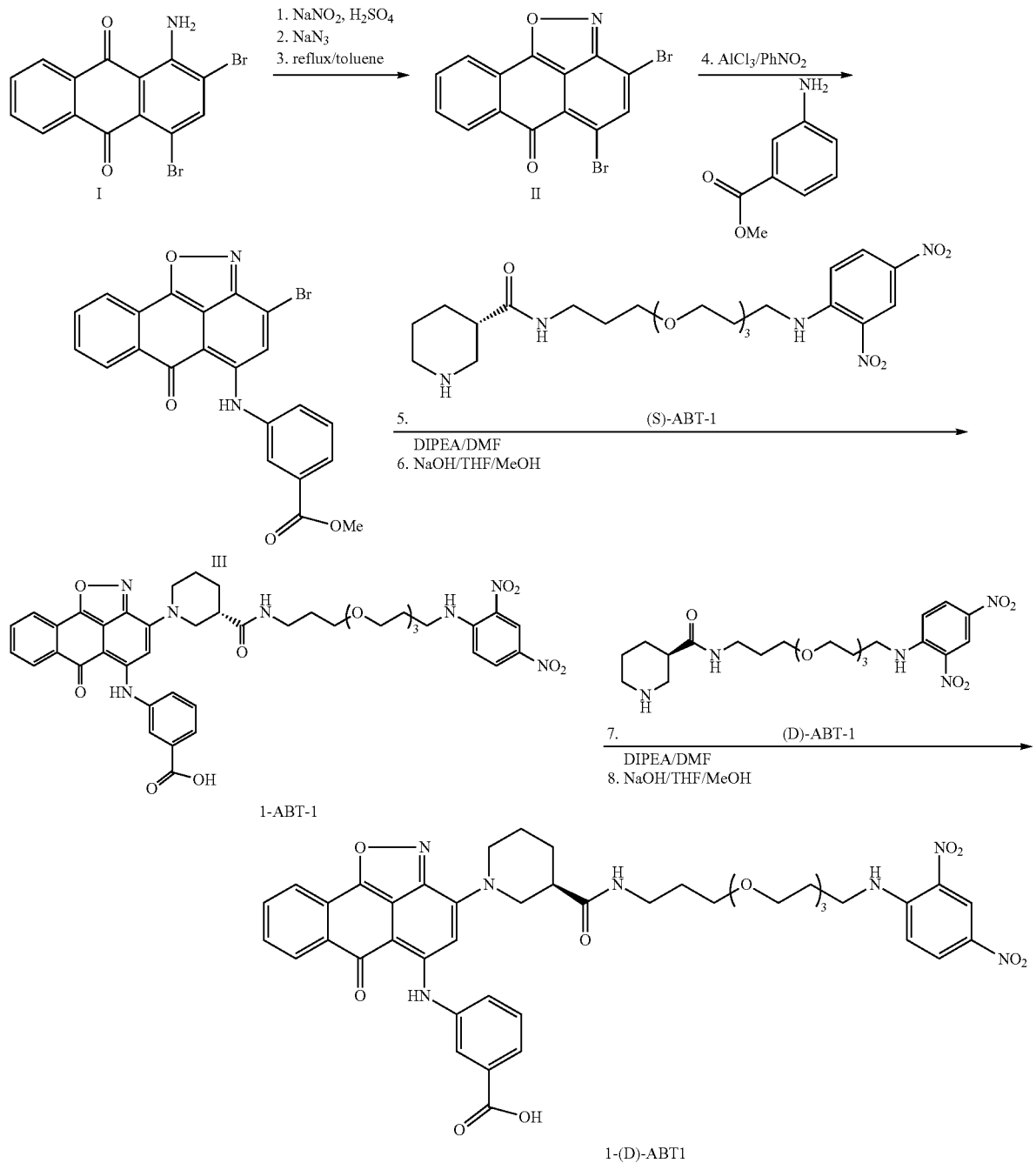

Synthesis of Intermediate I

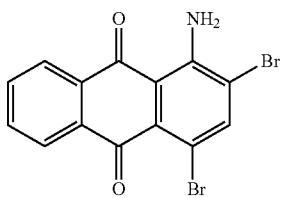 [SMILES: Nc1c(Br)cc(Br)c2c1C(=O)c1ccccc1C2=O]

To a flame dried flask under argon was added 5-hydroxy-1,4-naphthoquinone (300 mg, 1.7 mmol) followed by 30 ml of anhydrous DCM. The flask was flushed with argon followed by the addition of 1-(trimethylsiloxy)-1,3-butadiene (0.447 ml, 2.55 mmol) by syringe and left to stir at RT for 24 hr under argon. Upon complete consumption of starting material, 1.2 ml of anhydrous triethylamine was added and left to stir at RT for 12 hr. The solution was extracted against DCM and brine/1N HCL, dried using sodium sulfate, and purified by column chromatography (1:1 Hex/DCM to 100% DCM resulting in the isolation of pure hydroxyanthroquinone (intermediate i) in 47% yield (180 mg, 0.8 mmol) as a yellow solid. $^1$H NMR (600 MHz, Chloroform-d) 12.60 (s, 1H), 8.30 (m, 2H), 7.82 (m, 3H), 7.67 (t, J=7.9 Hz, 1H), 7.31 (d, J=8.3 Hz, 1H). $^{13}$C NMR (151 MHz, CDCl$_3$) 188.65, 182.41, 162.54, 136.74, 134.66, 134.17, 133.59, 133.43, 133.17, 127.41, 126.90, 124.35, 119.55, 116.13. HRMS (ES+) calc'd for C$_{14}$H$_9$O$_3$ (M+H) m/z 225.0473, Found. 225.0461 The anthroquinone (0.180 g, 0.8 mmol) was dissolved in 10 ml anhydrous DMF to which KI (13 mg, 0.08 mmol), potassium carbonate (221 mg, 1.6 mmol), and chloroacetamide (93 mg, 1.0 mmol) were added. The solution was heated to 90° C. for 1 hr followed by 150° C. for 24 hours followed by extraction with 1N HCL and EtOAc. The organic fractions were dried using sodium sulfate, concentrated in vacuo, and the remaining red residue purified by ISCO silica chromatography using a Hex/EtOAc gradient (10% EtOAc to 50% over 30 min) resulting in the isolation of anilinoanthroquinone intermediate ii (156 mg, 0.7 mmol) in 87% yield as a red solid $^1$H NMR (600 MHz, Chloroform-d) 8.29 (d, J=7.7 Hz, 1H), 8.25 (d, J=7.6 Hz, 1H), 7.77 (t, J=7.5 Hz, 1H), 7.72 (t, J=7.5 Hz, 1H), 7.65 (d, J=7.3 Hz, 1H), 7.46 (t, J=7.8 Hz, 1H), 6.97 (d, J=8.3 Hz, 1H), 6.84 (brm, 2H). $^{13}$C NMR (151 MHz, CDCl$_3$) 185.24, 183.60, 150.99, 134.73, 134.40, 133.94, 133.17, 129.64, 128.31, 126.79, 123.08, 117.29, 113.65. HRMS (ES+) calc'd for C$_{14}$H$_9$NO$_2$ (M+H) m/z 224.0633, Found. 224.0623.

The anilinoanthroquinone (78 mg, 0.35 mmol) was dissolved in 5 ml of glacial acetic acid predried using 3 A molecular sieves to which bromine was added (72 ul, 1.4 mmol) and the reaction stirred at room temperature for 12 hr. The solution was extracted against DCM and brine, the organic layers combined, dried, and concentrated as described above with the isolated red solid purified by ISCO silica chromatography using a hexane/DCM gradient (20% DCM-100% DCM). The isolated fractions were concentrated with the crude brominated anthroquinone product crystallized out of DCM/MeOH resulting in the isolation of pure dibromo-anilinoanthroquinone I in 65% yield $^1$H NMR (600 MHz, Chloroform-d) 8.24 (td, J=7.5, 2.2 Hz, 2H), 8.08 (s, 1H), 7.76 (ddd, J=6.4, 3.8, 1.8 Hz, 2H). $^{13}$C NMR (151 MHz, CDCl$_3$) 184.37, 182.27, 147.97, 143.97, 133.94, 133.82, 133.45, 133.26, 130.67, 127.08, 126.60, 117.50, 115.33, 108.71. HRMS (ES+) calc'd for C$_{14}$H$_8$Br$_2$NO$_2$ (M+H) m/z 379.8844 Found. 379.8841.

Synthesis of ARM-U2 Derivative 3-(R)-ABT-1 diazotization in the presence of sodium nitrate and sulfuric acid. Following displacement by aqueous sodium azide, cyclization to furnish the isoxazole was accomplished by refluxing in toluene to yield intermediate II in 66% yield as reported previously (REF). The di-bromo-isoxazole Intermediate II (200 mg, 0.52 mmol) was coupled to methyl-3-aminobenzoate in nitrobenzene using AlCl$_3$ to furnish the aniline substituted derivative III in 60% yield as reported previously (REF). The first and shortest length PEG derived antibody binding terminus 1 (S/R)-ABT-1 synthesized in this report, was prepared by first coupling 1-chloro-2,4-dinitrobenzene to 4,7,10-trioxa-1,13-tridecanediamine as described previously (REF). The resulting DNP appended PEG-linker (1.16 g, 3 mmol) was subsequently dissolved in 20 ml DCM to which BOC-D-nipecotic acid or BOC-L-nipecotic acid (0.5 g, 2.2 mmol), EDC (0.506 g, 2.64 mmol), and HOBt were added. The solution was left stirring at room temperature overnight. The solution was then diluted with 50 ml DCM and washed with a 1:1:1 mixture (60 ml) of water, brine, and saturated sodium bicarbonate (3×) followed by a 1:1:1 mixture (60 ml) of 10% citric acid, water, and brine. The organic layer was dried using sodium sulfate, filtered, and concentrated resulting in a dark-reddish oil. The crude BOC-protected (R/S)-ABT-1, was dissolved in a 1:1 mixture of TFA/DCM and stirred at room temperature for 5 hr. TFA was removed under a stream of nitrogen and the DCM was removed in vacuo. The dark oil was dissolved in EtOAc, washed with a 1:1:1 solution of 10% NaOH/water/brine, dried with sodium sulfate and concentrated to yield crude R/S-ABT-1 (1.3 g, quantitative) used directly in the next step. R-ABT-1 (31 mg, 0.0625 mmol) was dissolved in 1 ml of anhydrous ACN to which dry DIPEA (0.31 mmol) and intermediate III were added (11 mg, 0.025 mmol). The reaction was allowed to proceed for 5 hr at 80° C. in the dark with quantitative conversion to product confirmed by LC-MS. To the resulting orange-reddish solution was added 2 ml of 10% aqueous NaOH and 1 ml methanol and the solution was left stirring for 5 hr at room temperature in the dark. Following confirmation of quantitative ester deprotection by LC-MS, a stream of nitrogen was passed over the solution to remove the majority of organic solvent, and the resulting slurry dissolved in DMSO. The product was purified by ISCO C-18 reverse-phase chromatography (shielded from direct light) with a gradient of 30% ACN-100% ACN over 50 min (Both water and ACN contain 10 mM pH 4 ammo-

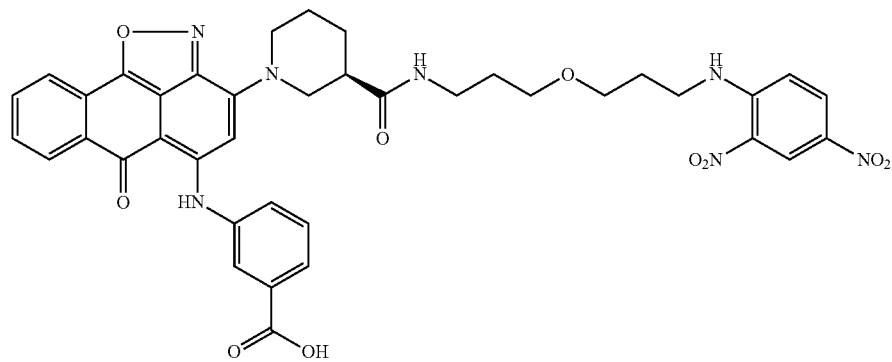 [SMILES: O=C(O)c1cccc(Nc2cc(N3CCC[C@@H](C(=O)NCCCOCCCNc4ccc([N+](=O)[O-])cc4[N+](=O)[O-])C3)c3noc4c3c2C(=O)c2ccccc2-4)c1]

The synthesis of intermediate III was carried out as described previously (REF). Briefly, 1-amino-2,4-dibromoanthraquinone (I) (5 g, 13.1 mmol), was subjected to nium formate buffer) and following lyophillzation yielded 1-(R)-ABT-1 in 44% yield (9.5 mg, 0.011 mmol) as a lyophilized reddish-orange solid. $^1$H NMR (500 MHz, DMSO-$d_6$) 11.76 (s, 1H), 8.88 (t, J=5.5 Hz, 1H), 8.73 (d, J=2.7 Hz, 1H), 8.43 (d, J=7.9 Hz, 1H), 8.17-8.1 (m, 2H), 7.99 (s, 1H), 7.91 (br s, 1H) 7.82 (m, 2H), 7.70 (m, 2H), 7.58 (t, J=7.8 Hz, 1H), 7.09 (d, J=9.7 Hz, 1H), 6.38 (s, 1H), 4.55 (br s, 2H), 4.37 (br s, 2H) 3.55-3.3 (m, 14H), 3.19-2.98 (m, 2H), 2.80 (m, 1H), 1.84 (m, 4H), 1.58 (m, 4H). $^{13}$C NMR (151 MHz, DMSO) 175.50, 172.43, 167.28, 154.29, 153.21, 148.49, 146.19, 138.59, 134.92, 133.25, 131.86, 130.41, 130.24, 129.81, 128.98, 127.95, 126.53, 123.98, 123.95, 123.91, 122.32, 118.98, 115.36, 95.83, 94.71, 70.15, 69.93, 68.72, 68.44, 55.36, 41.43, 40.86, 36.16, 29.61, 28.65, 27.86. HRMS (ES+) calc'd for $C_{43}H_{46}N_7O_{12}$ (M+H) m/z 852.3204, Found. 852.3296.

Hz, 1H), 7.69 (t, J=8.1 Hz, 1H), 7.49 (m, 2H), 7.10 (d, J=9.7 Hz, 1H), 6.43 (s, 1H), 4.55 (br s, 2H), 4.35 (br s, 2H) 3.57-3.29 (m, 14H), 3.08 (m, 2H), 2.60 (t, J=10.7 Hz, 1H), 1.84 (m, 4H) 1.54 (m, 4H). $^{13}$C NMR (151 MHz, DMSO) 174.92, 171.96, 167.95, 164.59, 153.70, 152.84, 148.08, 145.53, 137.49, 134.47, 132.84, 131.34, 129.83, 129.36, 128.46, 127.51, 126.06, 123.50, 123.28, 121.87, 118.56, 114.97, 95.37, 94.51, 69.74, 69.50, 68.31, 68.11, 54.99, 41.02, 39.94, 35.82, 29.16, 28.25, 27.56. HRMS (ES+) calc'd for $C_{43}H_{46}N_7O_{12}$ (M+H) m/z 852.3204. Found. 852.3390.

Scheme S2. Synthesis of intermediate length PEG-8 containing ABTs (v and xi) for longer linker ARM-U2 derivatives. Note that any numbers of PEG from 1 up to 15 or more may be used. The diamide connector group CT in this scheme contains three methylene groups, but numerous alternative lengths may also be used.

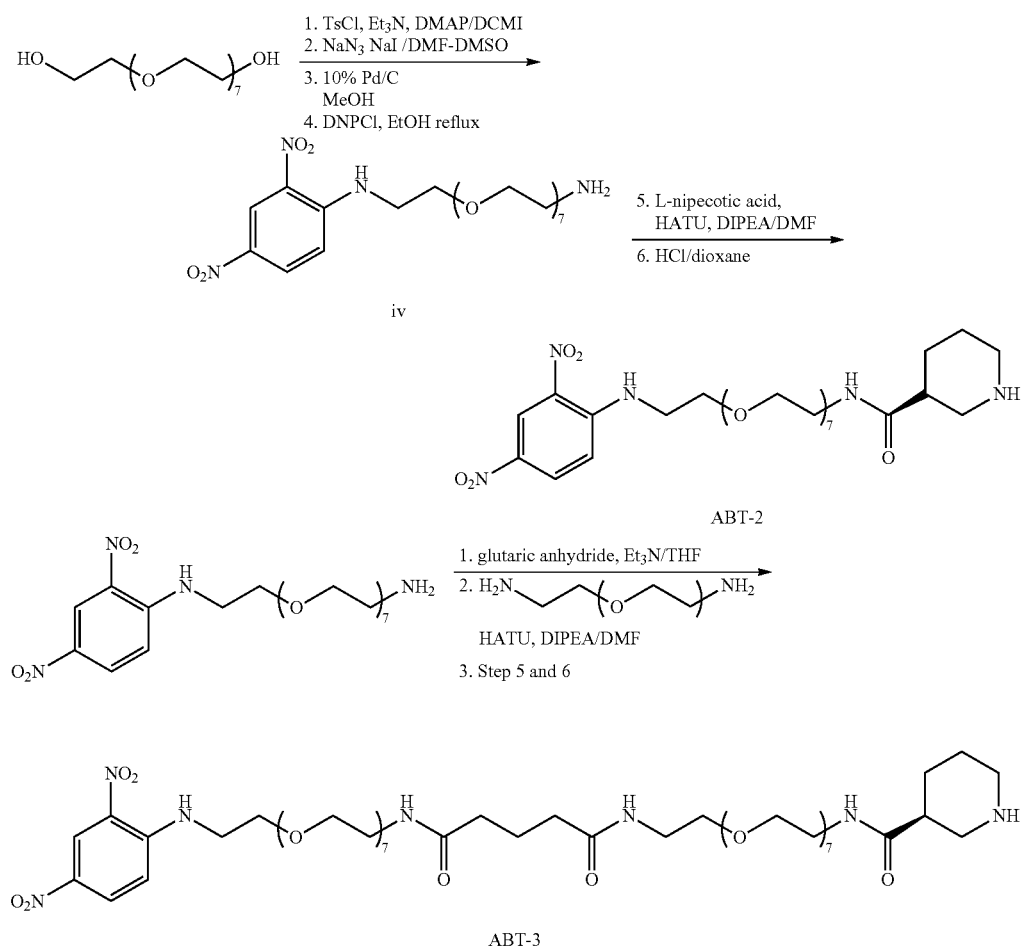

Synthesis of ARM-U2 Derivative 1-ABT-1

ARM-U2 derivative 1-ABT-1 was prepared and purified identically as described for 1-(R)-ABT-1 only ABT-1 was synthesized using Boc-L-nipecotic acid. 1-ABT-1 was isolated in 52% yield (11 mg, 0.013 mmol). $^1$H NMR (500 MHz, DMSO-$d_6$) 11.78 (s, 1H), 8.89 (t, J=5.6 Hz, 1H), 8.74 (d, J=2.7 Hz, 1H), 8.44 (d, J=8.0 Hz, 1H), 8.34 (s, 1H), 8.13 (m, 2H), 8.05 (s, 1H), 7.82 (t, J=8.1 Hz, 1H), 7.77 (d, J=6.9

Synthesis of PEG-8 Derived (R/S)-ABT-2

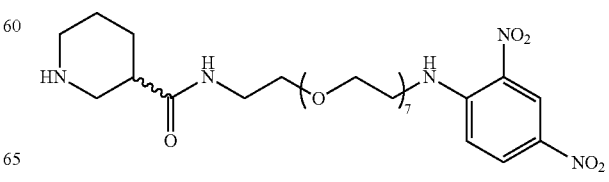

ABT-2 (Scheme S2) was synthesized from commercially available octaethylene glycol. The diol (5 g, 0.0135 moles) was dried for 24 hours under vacuum while stirring with molecular sieves prior to use following which time, it was dissolved in anhydrous DCM (60 ml) under nitrogen. To this solution was added dry $Et_3N$ (4.5 ml, 0.033 moles) followed by TsCl (7.0 g, 0.04 moles) and finally DMAP (0.1645 g, 0.00135 moles). The reaction was allowed to proceed for 12 hours at room temperature at which time the solution was washed with 1N HCl followed by an aqueous saturated sodium bicarbonate solution. The organic layers were combined, dried using sodium sulfate, concentrated in vacuo and the resulting oil purified by ISCO silica chromatography with a DCM/MeOH gradient. Bis-tosyl PEG-8 was isolated as a pale yellow oil in 89% yield (8 g, 0.012 moles). Bis-tosyl PEG-8 (2 g, 0.0029 moles) was dissolved in 24 ml of a 1:1 DMF/DMSO solution to which NaI (0.153 g, 0.001 moles) and $NaN_3$ (1.34 g, 0.021 moles) were added. The solution was left stirring at 60° C. over night, diluted in diethylether and extracted against brine and sodium bicarbonate. The organic layers were combined, dried using sodium sulfate and concentrated in vacuo to yield bis-azide g, 0.0024 moles) in 50 ml DMF in the presence of DIEPA (418 ul, 0.0024 moles) and HATU (0.912 g, 0.0024 moles) for 5 hr at room temperature. The solution was extracted against using brine/EtOAc and the organic layer concentrated in vacuo. The dark reddish oil was dissolved in 4M HCl/dioxane and stirred for 5 hr at room temperature following which time the solution was concentrated to dryness under a stream of nitrogen and left overnight under vacuum. Crude (R or S) ABT-2 was purified using HPLC (water/ACN 0.1% formic acid) to yield pure R or S-ABT-2 as the formate salt in 75% yield over 2 steps (0.64 g, 0.0012 moles). S-isomer: $^1$H NMR (600 MHz, Chloroform-d) 9.13 (d, J=2.6 Hz, 1H), 8.81 (m, 1H), 8.27 (d, J=12.0 Hz, 1H), 7.55 (m, 1H), 6.97 (d, J=9.5 Hz, 1H), 3.83-3.53 (m, 32H), 3.44 (m, 1H), 3.39 (m, 2H), 3.29 (m, 1H), 3.12 (m, 1H), 2.97 (s, 1H), 2.90 (m, 1H), 1.95 (m, 1H), 1.90 (m, 2H), 1.81 (m, 1H). $^{13}$C NMR (151 MHz, $CDCl_3$) 172.38, 148.41, 136.03, 130.27, 124.28, 114.16, 70.28, 69.48, 68.53, 50.66, 45.95, 43.90, 43.22, 39.18, 38.94, 25.96, 21.05. HRMS (ES+) calc'd for $C_{28}H_{47}N_5O_{12}$ (M+H) m/z 645.3221. Found. 645.3207.

Synthesis of ARM-U2 Derivative 1-(R)-ABT-2

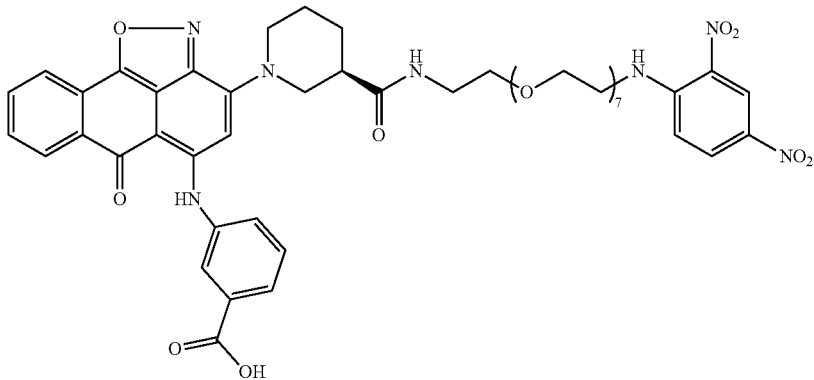

PEG-8 in approx. 80% crude yield (1.7 g, 0.004 moles). The bis-azide (1.2 g, 0.0028 moles) was dissolved in 46 ml of methanol and reduced under an atmosphere of hydrogen in the presence of 10% Pd/C. The reaction mixture was filtered through a celite plug, eluted with methanol, and concentrated to yield PEG8-diamine containing a significant amount of NaOMe but with sufficient purity to functionalize with DNP chloride. Peg8-diamine was acidified using 4M HCL in dioxane and dried in vacuo to yield PEG8-diamine in 95% yield as the HCL salt (1 g, 0.0027 moles). The PEG8-diamine HCL salt (0.846 g, 0.0023 moles) was neutralized with 1 eq DIPEA and refluxed in 10 ml of EtOH to which small portions of DNP-Cl (0.465 g, 0.0023 moles total) were added over 5 hr, diluted in DCM and washed with sodium bicarbonate and brine. Key intermediate iv was isolated as reddish oil in 69.5% yield (0.860 g, 0.0016 moles) and coupled directly to L or D-nipecotic acid (0.550

The synthesis and purification of ARM-U2 derivative 1-(R)-ABT-2 was carried out exactly as described above for derivative 1-(R)-ABT-1 except that (R)-ABT-2 (48 mg, 0.075 mmol) was coupled to intermediate III as opposed to intermediate (R)-ABT-1 to yield 1-(R)-ABT-2 in 50% yield (12.5 mg, 0.0125 mmol). $^1$H NMR (500 MHz, DMSO-$d_6$) 11.78 (s, 1H), 8.83-8.75 (m, 2H), 8.45 (d, J=8.0 Hz, 1H), 8.17 (m, 2H), 8.08 (br s, 1H), 8.00 (s, 1H) 7.82-7.79 (m, 2H), 7.75-7.66 (m, 2H), 7.58 (t, J=7.8 Hz, 1H), 7.20 (d, J=9.6 Hz, 1H), 6.40 (s, 1H), 4.51 (br s, 4H), 3.72-3.11 (m, 32H), 2.65-2.56 (m, 1H), 1.88 (m, 1H), 1.76 (m, 1H), 1.67-1.57 (m, 1H), 1.24 (m, 1H). $^{13}$C NMR (126 MHz, DMSO) 175.50, 172.72, 167.45, 154.28, 153.24, 148.71, 148.52, 146.19, 138.50, 135.24, 133.27, 131.85, 130.31, 130.19, 129.97, 129.54, 129.14, 128.96, 127.97, 126.52, 123.97, 123.94, 123.86, 122.31, 119.00, 115.97, 95.85, 94.82, 70.23, 70.04, 69.38, 68.65, 55.36, 43.08, 42.34, 38.91, 27.98, 24.41. HRMS (ES+) calc'd for $C_{43}H_{45}N_7O_{12}$ (M+H) m/z 852.3126. Found. 852.3156.

Synthesis of ARM-U2 Derivative 1-ABT-2

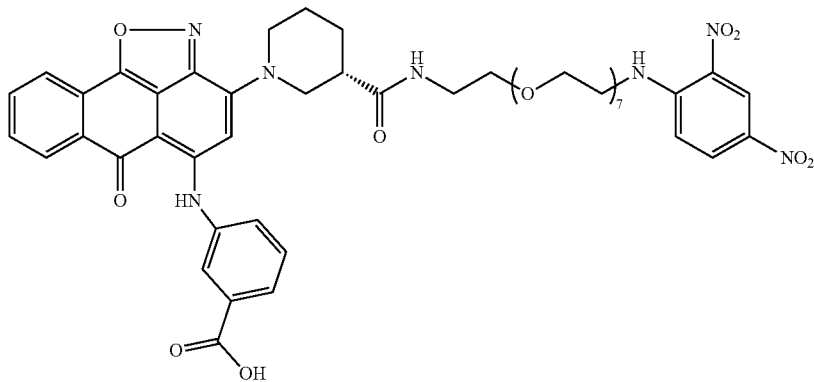

ARM-U2 derivative 1-ABT-2 was synthesized and purified as described above for 1-ABT-1 only ABT-2 was coupled to intermediate III as opposed to ABT-1 resulting in the isolation of 1-ABT-2 in % 45 yield (11.25 mg, 0.011 mmol) $^1$H NMR (500 MHz, DMSO-$d_6$) 11.81 (s, 1H), 8.80 (m, 1H), 8.47 (d, J=8.0 Hz, 1H), 8.25 (s, 1H), 8.22-8.14 (m, 2H), 8.08 (s, 1H), 7.84 (t, J=7.3 Hz, 1H), 7.77 (d, J=6.9 Hz, 1H), 7.72 (t, J=7.5 Hz, 1H), 7.50 (br m, 2H), 7.21 (d, 1H), 6.49 (s, 1H), 4.72 (br s, 2H) 4.36 (brs, 2H) 3.70-3.13 (m, 32H), 2.66 (m, 1H), 1.93-1.77 (m, 3H), 1.66-1.56 (m, 1H). $^{13}$C NMR (151 MHz, DMSO) 175.34, 172.63, 168.64, 165.35, 154.11, 153.39, 148.71, 148.58, 145.97, 137.70, 135.22, 133.30, 131.78, 130.20, 129.96, 129.57, 128.89, 127.96, 126.51, 123.95, 123.88, 122.30, 119.02, 115.99, 95.78, 95.10, 70.18, 69.98, 69.25, 68.63, 43.06, 38.88, 28.06. HRMS (ES+) calc'd for $C_{49}H_{58}N_7O_{16}$ (M+H) m/z 1000.3940. Found. 1000.3959.

Synthesis of PEG-8 Derived ABT-3

0.1% triethylamine) to obtain the crude DNP-PEG8-acid (0.57 g, 0.0008 moles) in approx. 88% yield. The DNP-PEG8-acid (0.57 g, 0.0008 moles) was dissolved in 5 ml of anhydrous DMF and added portion wise to a solution of PEG8diamine HCl (0.59 g, 0.0016 moles) HATU (0.304 g, 0.0008 moles), and anhydrous DIPEA (140 ul, 0.0008 moles) in 5 ml anhydrous DMF. The solution was purified by C18 ISCO using 0.1% formic acid/MeOH to yield the crude DNP-PEG16-amine in approx. 80% yield (0.639 g, 0.00064 moles). Boc-L-nipecotic acid coupling, deprotection and linker purification was quantitative and carried out as described for the synthesis of ABT-2 to yield ABT-3 in 66% overall yield (0.658 g, 0.0006 moles). $^1$H NMR (400 MHz, DMSO-$d_6$) 8.87 (d, J=2.8 Hz, 1H), 8.49 (brs, 1H) 8.27 (dd, J=9.6, 2.7 Hz, 1H), 7.93 (t, J=5.3 Hz, 1H), 7.85 (t, J=5.4 Hz, 2H), 7.29 (d, J=9.7 Hz, 1H), 3.69 (m, 6H), 3.57 (m, 2H), 3.50 (m, 48H), 3.38 (m, 4H), 3.17 (m, 4H), 2.92-2.76 (m, 4H), 2.44 (m, 1H) 2.26-2.17 (m, 1H), 2.04 (t, J=7.5 Hz, 4H),

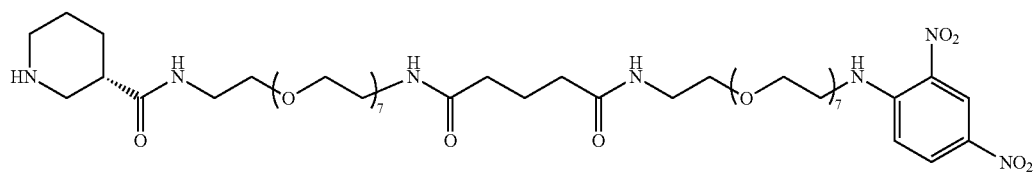

Key intermediate iv (0.485 g, 0.0009 moles) described above was coupled to glutaric anhydride (0.155 g, 0.00136 moles) in 10 ml of anhydrous THF in the presence of DIPEA (236 ul, 0.0013 moles) for 8 hr at room temperature (Scheme S2). The solution was concentrated under reduced pressure and purified by ISCO-C18 chromatography (water/ACN 1.75-1.64 (m, 2H), 1.57-1.42 (m, 2H), 1.37-1.28 (m, 2H). $^{13}$C NMR (151 MHz, DMSO) 174.23, 172.22, 166.24, 148.82, 135.30, 130.32, 124.00, 116.14, 70.20, 68.70, 48.93, 45.99, 43.09, 38.85, 38.73, 35.11, 28.10, 25.21, 21.94. HRMS (ES+) calc'd for $C_{49}H_{88}N_7O_{21}$ (M+H) 1109.5955 m/z. Found 1109.5932.

Synthesis of ARM-U2 Derivative 1-ABT-3

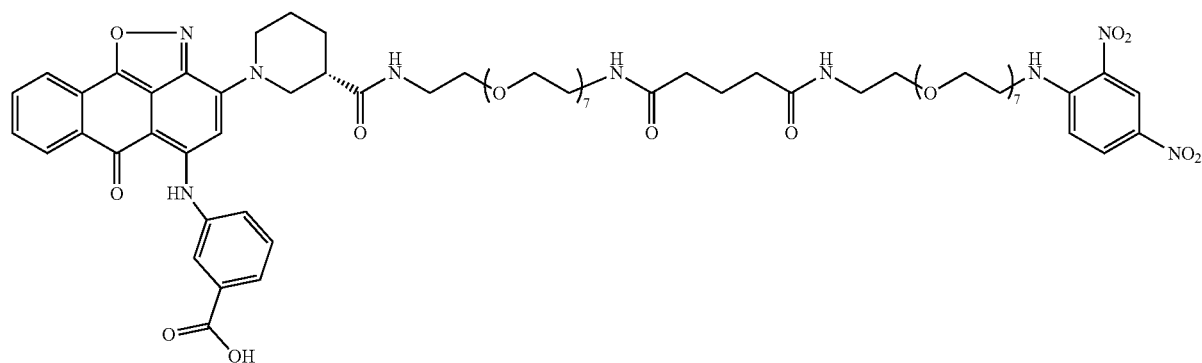

ARM-U2 derivative 1-ABT-3 was synthesized and purified as described above for 1-ABT-1 only ABT-3 (83 mg, 0.075 mmol) was coupled to intermediate III giving rise to 1-ABT-3 in 38% yield (13.9 mg, 0.0095 mmol) $^1$H NMR (500 MHz, DMSO-$d_6$) 11.82 (s, 1H), 8.82 (d, J=2.7 Hz, 1H), 8.57 (brs, 1H), 8.47 (d, J=7.9 Hz, 1H), 8.44 (brs, 1H), 8.22 (dd, J=9.6, 2.5 Hz, 1H), 8.18 (d, J=7.8 Hz, 1H), 8.10 (s, 1H), 7.86-7.82 (m, 3H), 7.74 (d, J=7.4, 1H), 7.71 (m, 1H)), 7.41 (m, 1H), 7.25 (d, J=9.7 Hz, 1H), 6.52 (s, 1H), 4.77 (brs, 2H), 4.19 (brs, 2H), 3.73-3.09 (m, 64H), 2.67 (m, 1H), 2.03 (t, J=7.4 Hz, 4H), 1.91-1.78 (m, 3H), 1.67-1.58 (m, 3H). $^{13}$C NMR (151 MHz, DMSO) 175.31, 172.56, 172.23, 168.67, 165.72, 154.08, 153.44, 148.77, 148.63, 145.87, 137.43, 135.27, 133.33, 131.77, 130.27, 130.03, 129.32, 128.88, 127.98, 126.45, 123.95, 123.78, 123.56, 122.32, 119.05, 116.07, 95.80, 95.28, 70.12, 69.97, 69.55, 51.74, 50.85, 43.08, 41.88, 38.85, 35.11, 28.11, 25.00, 21.94. HRMS (ES+) calc'd for $C_{70}H_{97}N_9O_{25}$ (M+H) 1464.6596 m/z. Found 1464.6433.

-continued

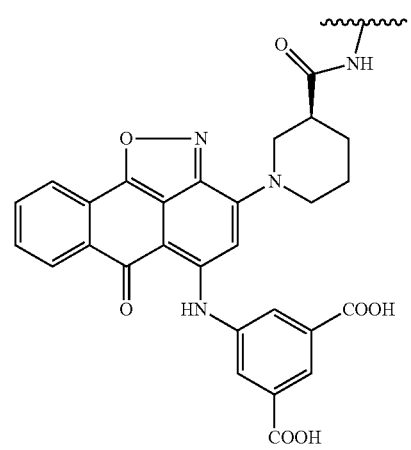

2-ABT-1, 2-ABT-2

Scheme S3. Synthesis of derivatives 2-ABT-1 and 2-ABT-2

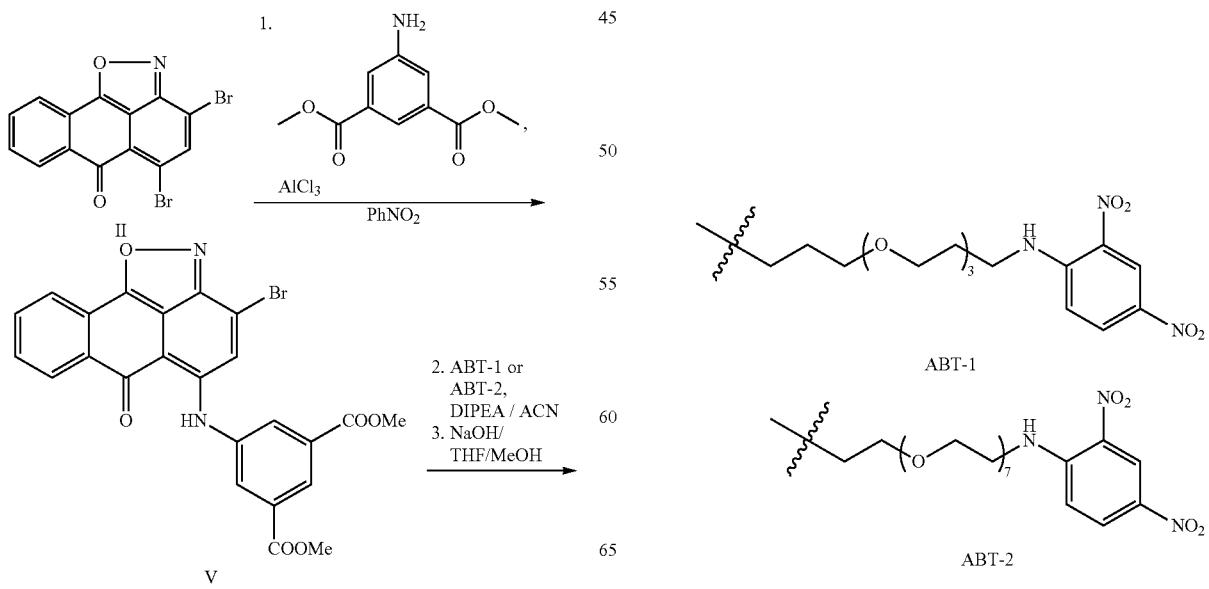

Synthesis of ARM-U2 Derivative 2-ABT-1

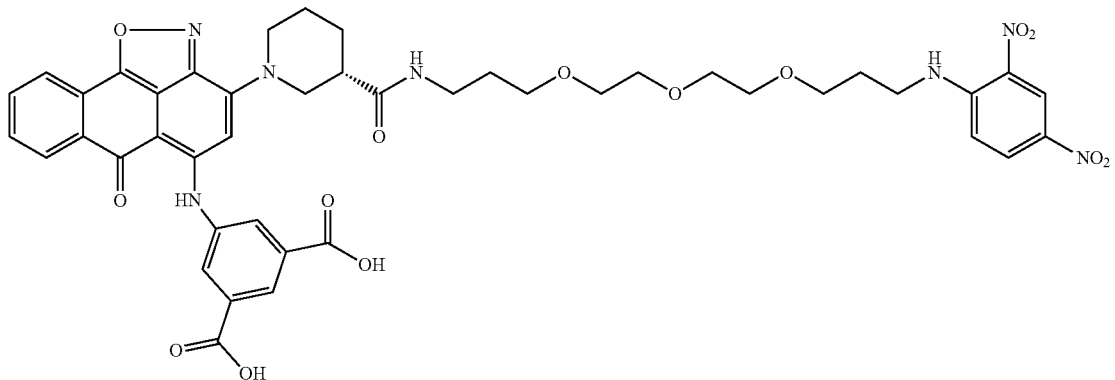 [SMILES: O=C(O)c1cc(Nc2cc(N3CCC[C@H](C(=O)NCCCOCCOCCOCCCNc4ccc([N+](=O)[O-])cc4[N+](=O)[O-])C3)c3noc4c3c2C(=O)c2ccccc2-4)cc(C(=O)O)c1]

Derivative 2-ABT-1 (Scheme S3) was synthesized as described above for 1-ABT-1 only differing in that dimethyl-5-aminoisophthalate was coupled to intermediate II instead of methyl-3-aminobenzoate to afford the mono-brominated product. Briefly, intermediate II (200 mg, 0.526 mmol) was dissolved in dry nitrobenzene along with dimethyl-5-aminoisophthalate (665 mg, 3 mmol). To this stirred solution was added anhydrous $AlCl_3$ (0.353 g, 2.65 mmol) and the reaction left to proceed for 3 hr. The resulting red solid intermediate V, was precipitated from ice water, recrystallized out of toluene in 36% crude yield (100 mg, 0.19 mmol) and carried directly over to the next step. The mono-brominated intermediate V (10 mg, 0.019 mmol) was coupled to ABT-1, deprotected, and purified as described above for the synthesis of derivative 1-ABT-1 resulting in the isolation of derivative 2-ABT-1 as a red solid in 40% yield (7 mg, 0.0076 mmol). $^1$H NMR (500 MHz, DMSO-$d_6$) 11.77 (s, 1H), 8.89 (t, J=5.3 Hz, 1H), 8.73 (d, J=2.6 Hz, 1H), 8.43 (d, J=8.0 Hz, 1H), 8.30 (s, 1H), 8.19-8.08 (m, 5H), 7.83 (t, J=7.5 Hz, 1H), 7.70 (t, J=7.6 Hz, 1H), 7.09 (d, J=9.7 Hz, 1H), 6.43 (s, 1H), 4.49 (br s, 4H), 3.6-3.21 (m, 14H), 3.07 (m, 2H), 2.57 (m, 1H), 1.83 (m, 4H), 1.59 (m, 4H). $^{13}$C NMR (126 MHz, DMSO) 175.62, 172.35, 166.96, 163.63, 154.43, 152.92, 148.48, 146.02, 138.80, 134.93, 133.24, 131.88, 130.22, 129.82, 129.00, 127.98, 126.82, 123.98, 123.88, 122.31, 118.99, 115.36, 96.09, 94.87, 70.16, 69.90, 68.72, 68.50, 41.44, 36.24, 29.56, 28.66, 27.93. HRMS (ES+) calc'd for $C_{44}H_{46}N_7O_{14}$ (M+H) 896.3103 m/z 896.3103. Found 896.3094.

Synthesis of ARM-U2 Derivative 2-ABT-2

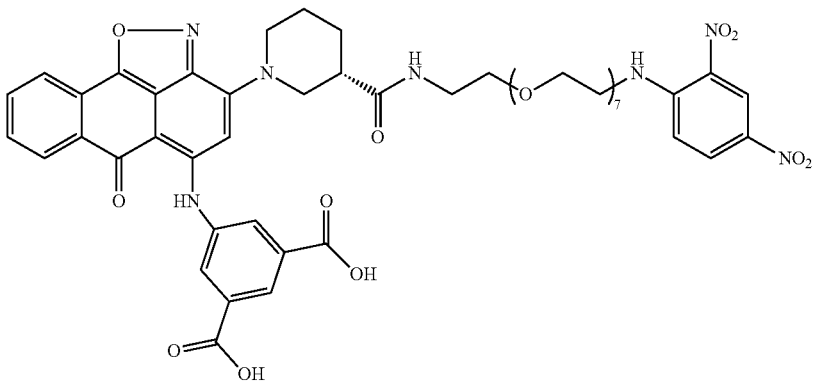

The synthesis of ARM-U2 derivative 4-ABT-2 (Scheme S3) was carried out exactly as described above for derivative 2-ABT-1 except that linker derivative ABT-2 was employed. Crude intermediate V (10 mg, 0.019 mmol) was coupled to derivative ABT-2, deprotected and purified as described for the synthesis of 2-ABT-1 giving rise to 2-ABT-2 in 43% yield (8.5 mg, 0.0082 mmol). $^1$H NMR (500 MHz, DMSO-d$_6$) 11.78 (s, 1H), 8.78 (m, 2H), 8.44 (d, J=7.8 Hz, 1H), 8.31 (s, 1H), 8.16 (m, 5H), 7.85-7.80 (m, 1H), 7.73-7.68 (m, 1H), 7.19 (d, J=9.6 Hz, 1H), 6.43 (s, 1H), 4.51 (br s, 4H), 3.73-3.08 (m, 32H), 2.59 (m, 1H), 1.94-1.70 (m, 3H), 1.62 (m, 1H). $^{13}$C NMR (126 MHz, DMSO) 175.64, 172.66, 166.90, 154.45, 152.92, 148.70, 148.49, 146.08, 138.92, 135.24, 133.24, 131.91, 130.18, 129.96, 129.01, 128.00, 126.96, 126.80, 124.00, 123.85, 122.32, 119.00, 115.96, 96.09, 94.87, 70.02, 69.32, 68.64, 43.07, 42.9, 38.9, 28.00, 24.39. HRMS (ES+) calc'd for $C_{50}H_{57}N_7O_{18}$ (M+H) 1043.3760 m/z. Found. 1043.3748.

Synthesis of ARM-U2 Derivative 3-ABT-1

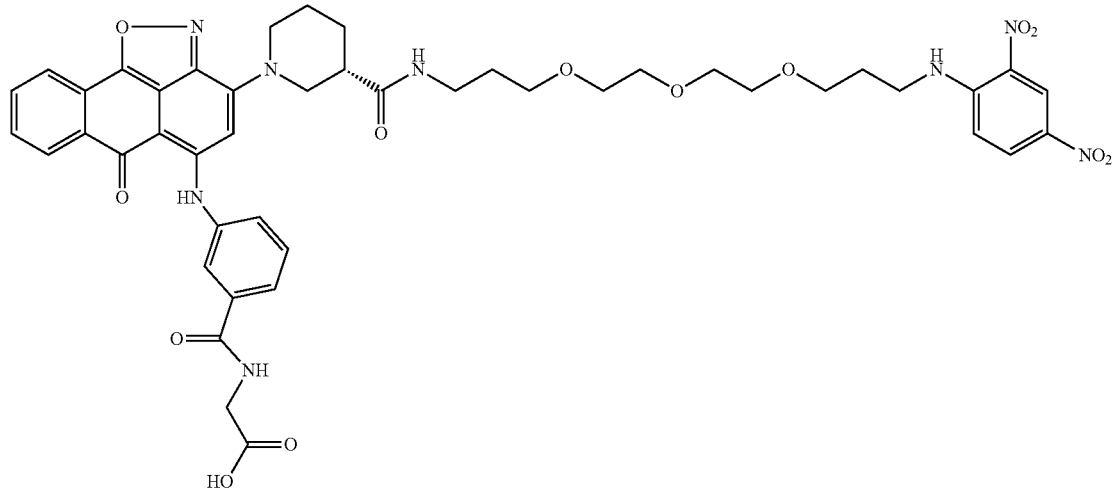 [SMILES: O=C(O)CNC(=O)c1cccc(Nc2cc(N3CCC[C@H](C(=O)NCCCOCCOCCOCCCNc4ccc([N+](=O)[O-])cc4[N+](=O)[O-])C3)c3noc4c3c2C(=O)c2ccccc2-4)c1]

ARM-U2 derivative 3-ABT-1 was synthesized by coupling derivative 1-ABT-1 (10 mg, 0.011 mmol) to GlyOMe (2.5 mg, 0.022 mmol) in the presence of DIPEA (2.3 ul, 0.0132 mmol), EDC (2.5 mg, 0.0132 mmol) and HOBt (1.8 mg, 0.0132 mmol) in DCM (2 ml) for 12 hr at room temperature (Scheme S4-A). The solution was diluted with 10 ml of DCM and washed 3× with 10 ml of brine. The organic layers were combined, dried with sodium sulfate and concentrated. The reddish residue was dissolved in a 1:1:1 solution of THF/MeOH/10% NaOH and stirred at room temperature for 5 hr. Organics were then removed under a stream of nitrogen and the remaining precipitate dissolved in DMSO and purified as described for ARM-U2 1-ABT-1 yielding 3-ABT-1 in 83% yield (8.2 mg, 0.009 mmol). $^1$H NMR (500 MHz, DMSO-d$_6$) 11.81 (s, 1H), 8.90 (t, J=5.6 Hz, 1H), 8.78 (m, 1H), 8.75 (d, J=2.7 Hz, 1H), 8.45 (d, J=8.0 Hz, 1H), 8.17-8.13 (m, 2H), 7.98 (s, 1H), 7.91 (t, J=5.3 Hz, 1H), 7.83 (t, J=7.0 Hz, 1H), 7.77 (d, J=7.7 Hz, 1H), 7.71 (t, J=7.6 Hz, 1H), 7.60. (t, J=7.8 Hz, 1H), 7.12 (d, J=9.7 Hz, 1H), 6.37 (s, 1H), 4.53 (br s, 2H), 4.39 (br s, 2H), 3.89-3.85 (m, 2H), 3.56-3.33 (m, 14H), 3.14 (m, 2H), 2.63 (m, 1H), 1.88 (m, 4H), 1.59 (m, 4H). $^{13}$C NMR (126 MHz, DMSO) 175.48, 172.51, 171.46, 165.65, 154.27, 153.33, 148.51, 146.28, 138.58, 136.15, 134.95, 133.27, 131.84, 130.35, 130.27, 129.86, 129.53, 128.96, 127.96, 126.29, 124.68, 123.92, 122.27, 118.97, 115.39, 95.78, 94.76, 70.15, 69.94, 68.73, 68.43, 42.74, 42.52, 41.45, 36.14, 29.64, 28.66, 27.83. HRMS (ES+) calc'd for $C_{45}H_{49}N_8O_{13}$ (M+H) m/z 909.3419.

Found. 909.3478.

Scheme S4. Synthesis of derivative 3-ABT-1 and 4-ABT-1
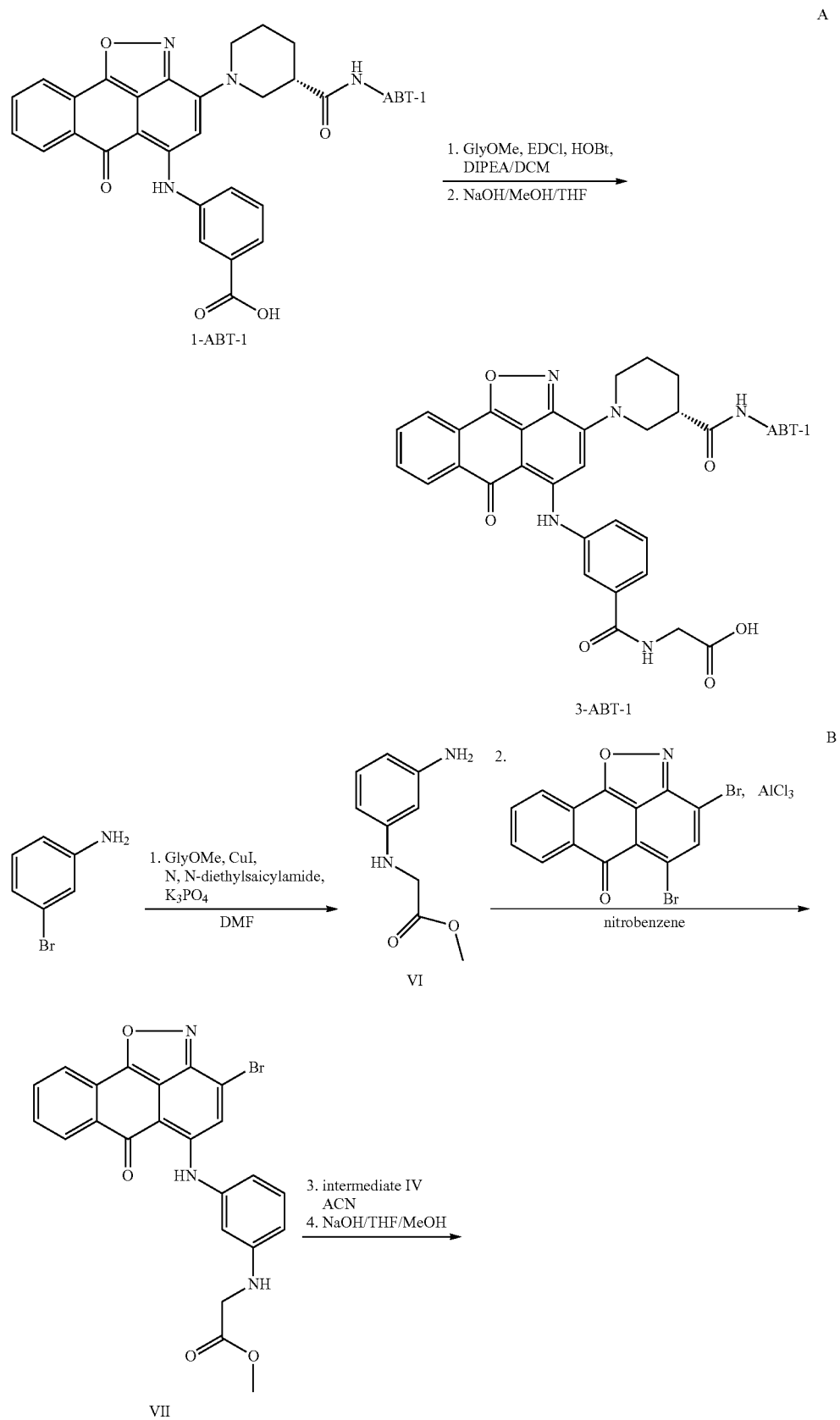

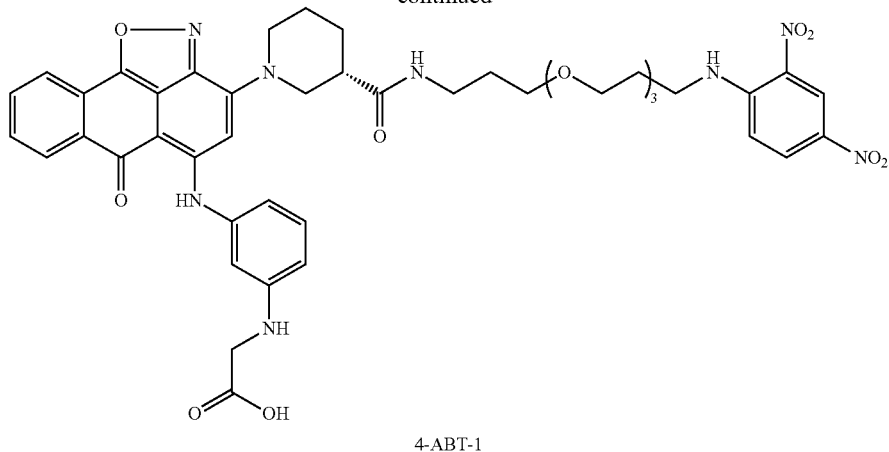

4-ABT-1

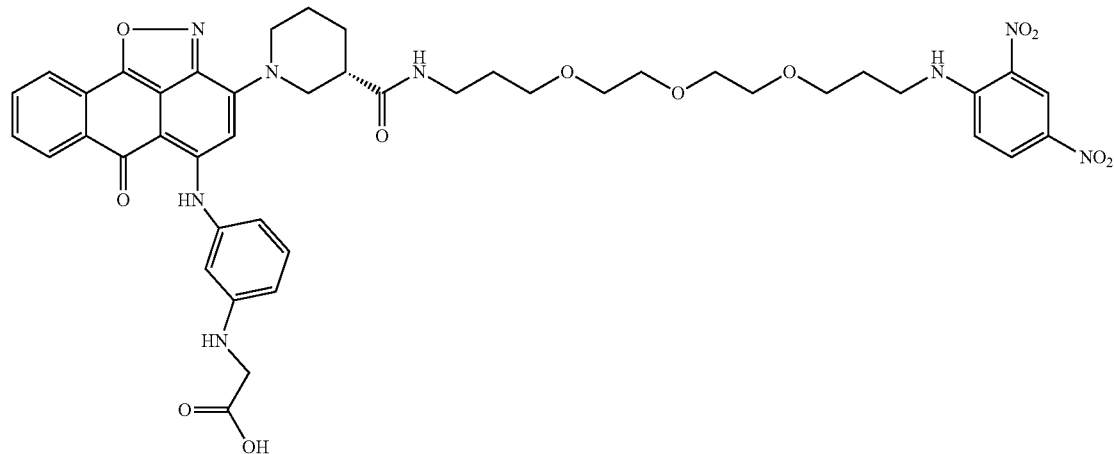 [SMILES: O=C(O)CNc1cccc(Nc2cc(N3CCC[C@H](C(=O)NCCCOCCOCCOCCCNc4ccc([N+](=O)[O-])cc4[N+](=O)[O-])C3)c3noc4c3c2C(=O)c2ccccc2-4)c1]

Synthesis of ARM-U2 Derivative 4-ABT-1

To a flame dried flask was added CuI (10 mg, 0.05 mmol), $K_3PO_4$ (636 mg, 3 mmol), N,N-diethylsalicylamide (39 mg, 0.2 mmol), and GlyOMe. HCl (188 mg, 1.5 mmol). The flask was backflushed with argon followed by the addition of anhydrous DMF (1 ml), and 3-bromoaniline (108 ul, 1 mmol) (Scheme S4-B). The mixture was stirred at 90° C. for 12 hr under argon, diluted with EtOAc and washed with brine 3× and saturated sodium bicarbonate. The EtOAc layers were collected dried with sodium sulfate and concentrated. The remaining oil was purified by ISCO flash chromatography with a 12 g column using a 0-50% gradient of DCM/EtOAc over 35 min. Pure glycine ester coupled aryl product intermediate VI was obtained in 10% yield (20 mg, 0.1 mmol). $^1$H NMR (400 MHz, Chloroform-d) 6.98 (t, J=7.9 Hz, 1H), 6.12 (d, J=9.1 Hz, 1H), 6.06 (d, J=8.8 Hz, 1H), 5.96 (s, 1H), 3.89 (s, 2H), 3.78 (s, 3H), 2.92 (m, 2H), 1.22 (m, 1H). $^{13}$C NMR (151 MHz, cdcl$_3$) 171.68, 148.12, 147.48, 130.20, 105.76, 103.94, 99.76, 52.23, 45.66.

HRMS (ES+) calc'd for $C_9H_{13}N_2O_2$ (M+H) 181.0899 m/z Found. 181.0876. Intermediate vi (20 mg, 0.1 mmol) was dissolved in 1 ml of dry nitrobenzene to which the di-bromo intermediate ii (40 mg, 0.11 mmol) and anhydrous DIPEA (46 ul, 0.26 mmol) was added. The solution was stirred at room temperature for five minutes and anhydrous $AlCl_3$ (35.6 mg, 0.26 mmol) was added accompanied by a fast colour change to deep red). The reaction mixture was diluted with DCM and added directly to an ISCO flash column and purified with a gradient of 0-40% DCM/EtOAc over 35 min with each solvent containing 0.1% acetic acid. The red solid mono-brominated product intermediate VII was obtained in 27.5% yield (13 mg, 0.0275 mmol). $^1$H NMR (500 MHz, Chloroform-d) 11.36 (s, 1H), 8.57 (d, J=8.0 Hz, 1H), 8.16 (d, J=7.8 Hz, 1H), 7.80 (d, J=2.5 Hz, 2H), 7.68 (t, J=8.1 Hz, 1H), 7.31 (t, J=8.0 Hz, 1H), 6.75 (d, J=6.6 Hz, 1H), 6.61 (d, J=10.3 Hz, 1H), 6.53 (s, 1H), 4.51 (t, J=5.3 Hz, 1H), 3.96 (d, J=5.4 Hz, 2H), 3.82 (s, 3H). $^{13}$C NMR (151 MHz, DMSO) 179.58, 171.98, 156.75, 151.18, 150.04, 149.26, 137.92, 133.39, 132.49, 130.69, 129.89, 128.49, 128.35, 124.93, 122.79, 118.82, 117.25, 112.37, 111.72, 107.67, 100.77, 52.16, 44.66. HRMS (ES+) calc'd for $C_{23}H_{17}BrN_3O_4$(M+H) 478.0324 m/z. Found. 478.0311 The mono-brominated intermediate VII (13 mg, 0.0275 mmol) was coupled to ABT-1, deprotected, and purified by C18 reverse phase chromatography as described above for derivative 1-ABT-1 resulting in the isolation of 4-ABT-1 as a red solid in 46% yield (11 mg, 0.0126 mmol). $^1$H NMR (500 MHz, DMSO-d$_6$) 11.71 (s, 1H), 8.91 (t, J=5.4 Hz, 1H), 8.76 (d, J=2.7 Hz, 1H), 8.45 (m, 2H), 8.21 (br m, 1H), 8.16 (m, 2H), 7.82 (t, J=7.6 Hz, 1H), 7.70 (t, J=7.5 Hz, 1H), 7.14-7.12 (m, 2H), 6.59 (m, 2H), 6.49 (br m, 1H), 6.46 (s, 1H), 4.5 (m, 4H), 3.58-3.38 (m, 14H), 3.07 (m, 2H), 2.58 (m, 1H), 1.86 (m, 4H), 1.60 (m, 4H). $^{13}$C NMR (151 MHz, DMSO) 175.00, 172.56, 171.44, 165.32, 153.78, 150.42, 148.60, 148.51, 146.20, 138.86, 134.92, 133.32, 131.60, 130.27, 129.83, 128.73, 127.89, 123.92, 123.82, 122.21, 119.00, 115.41, 110.83, 110.05, 106.16, 95.45, 95.17, 70.19, 70.14, 69.93, 68.71, 68.46, 41.42, 40.85, 40.47, 36.12, 29.65, 28.66, 27.75. HRMS (ES+) calc'd for $C_{44}H_{49}N_8O_{12}$ (M+H) 881.3470 m/z. Found 881.3536 m/z.

Two equivalents of predried DIPEA (452 ul, 2.6 mmol) was added directly to solid metanilic acid (0.227 g, 1.3 mmol) and the slurry dissolved in 3 angstrom pre-dried nitrobenzene (2 ml). To this solution was added di-bromo intermediate II (0.1 g, 0.26 mmol) and the solution sonicated for 15 min. To this slurry was added anhydrous $AlCl_3$ (0.182 g, 1.37 mmol) and the thick red solution was stirred for 3 hr at room temperature (Scheme S5). The reaction mixture was

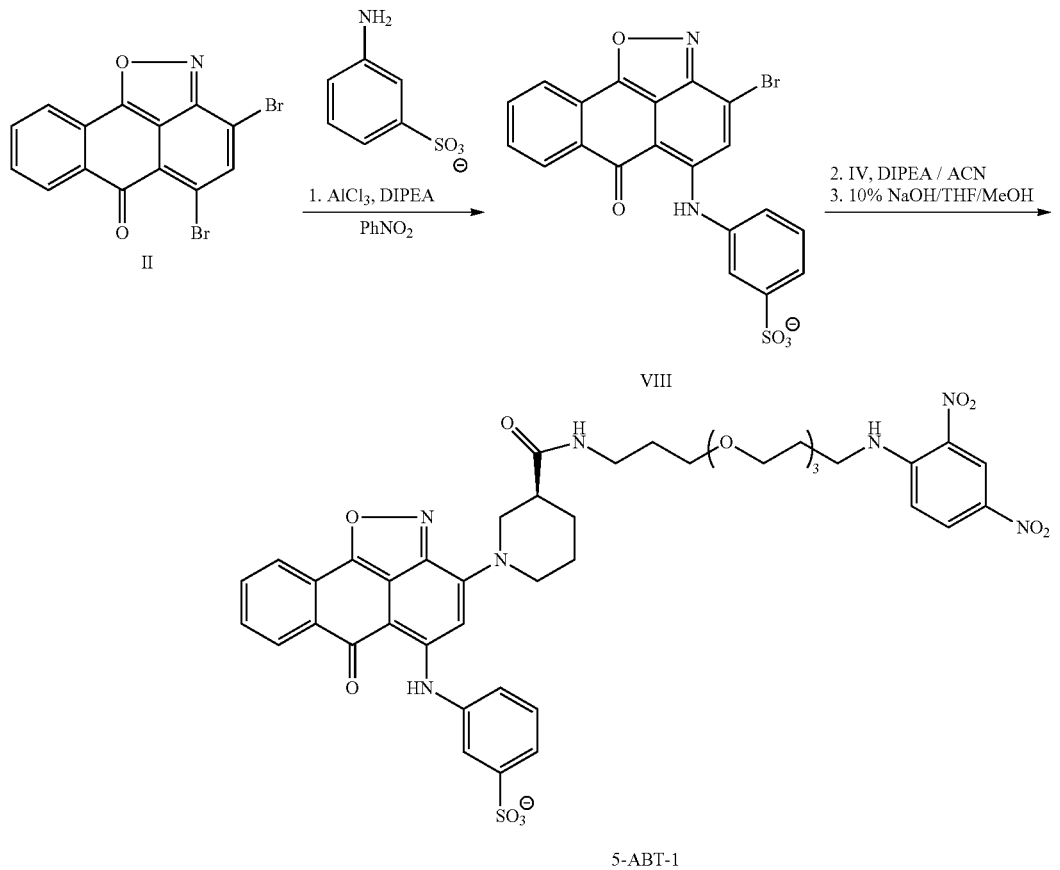

Synthesis of ARM-U2 Derivative 5-ABT-1

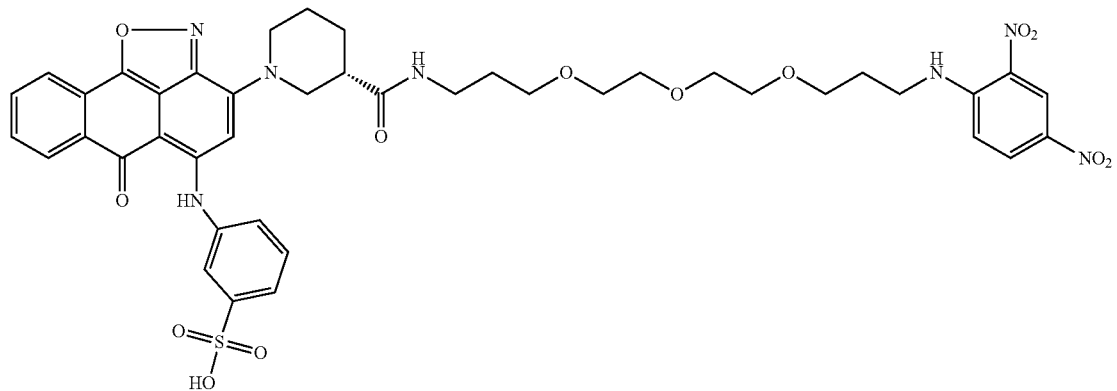 [SMILES: O=C1c2ccccc2-c2onc3c(N4CCC[C@H](C(=O)NCCCOCCOCCOCCCNc5ccc([N+](=O)[O-])cc5[N+](=O)[O-])C4)cc(Nc4cccc(S(=O)(=O)O)c4)c1c23]

diluted with DCM/MeOH (95:5) and loaded directly onto an ISCO silica column and purified using a gradient of DCM/MeOH (0-20%) with 1% acetic acid in each solvent. The crude mono-sulfonated intermediate VIII (approx. 89 mg, 0.189 mmol, 73% yield) was used directly in the next step. Intermediate VIII (10 mg, 0.021 mmol) was coupled to linker ABT-1 as described above for the synthesis of 1-ABT-1. Crude 5-ABT-1 was purified as described above for 1-ABT-1 only with slight modifications to the HPLC conditions now employing a 20%-100% gradient over 35 min with 10 mM ammonium formate pH 4 buffer/methanol as aqueous/organic phases respectively. ARM-U2 derivative 5-ABT-1 was isolated in 35% yield (6.5 mg, 0.00735 mmol) as a red solid. $^1$H NMR (500 MHz, DMSO-$d_6$) 11.74 (s, 1H), 8.90 (t, J=5.5 Hz, 1H), 8.76 (d, J=2.7 Hz, 1H), 8.46 (d, J=8.0 Hz, 1H), 8.21-8.12 (m, 2H), 8.00 (t, J=4.9 Hz, 1H), 7.83 (t, J=7.5 Hz, 1H), 7.74 (m 1H), 7.76-7.69 (m, 1H) 7.51 (d, J=6.4 Hz, 1H), 7.48 (t, J=7.5 Hz, 1H), 7.44 (d, J=7.8 Hz, 1H), 7.13 (d, J=9.7 Hz, 1H), 6.40 (s, 1H), 4.48 (br s, 4H), 3.62-3.33 (m, 14H), 3.09 (q, J=6.7, 6.3 Hz, 2H), 2.54 (m, 1H), 1.85 (m, 4H), 1.61 (m, 4H). $^{13}$C NMR (151 MHz, DMSO) 175.42, 172.37, 154.20, 153.35, 150.04, 148.57, 148.51, 146.01, 137.87, 134.89, 133.27, 131.82, 130.27, 129.92, 129.79, 128.94, 127.98, 123.94, 123.67, 122.91, 122.32, 120.61, 118.99, 115.42, 95.83, 94.82, 70.14, 69.92, 68.69, 68.48, 55.38, 49.04, 41.41, 36.12, 29.57, 28.66, 27.87. HRMS (ES+) calc'd for $C_{42}H_{46}N_7O_{13}S$ (M+H) 888.2874 m/z. Found 888.2927.

Synthesis of ARM-U2 Derivative 6-ABT-1

To a flame-dried flask under argon was added the dibromo intermediate II (0.020 g, 0.052 mmol) $Li_2CO_3$ (0.029 g, 0.4 mmol), aniline-2,4-disulfonic acid (0.100 g, 0.4 mmol) and $Cu(OAc)_2$ (0.0005 g, 0.0027 mmol). The flask was sealed and flushed with argon followed by the addition of 4 ml anhydrous DMF via syringe. The solution was stirred for 5 min under argon at room temperature and then heated to 70° C. for 24-36 hr shielded from room light. After reaction completion monitored by LCMS and reverse-phase TLC, the reaction mixture was precipitated out of a 12:1 (w,v) solution of diethylether/DMF at −20° C. and the isolated red precipitate dissolved in water and loaded onto a reverse phase C18 column. Crude intermediate VIIII was purified by reverse phase C18-ISCO chromatography in a dark room (0-80% $H_2O$/MeOH 0.1% formic acid/30 min). The isolated pinkish fractions were pooled and lyophilized giving rise to pure intermediate VIIII isolated in 55% yield (15.7 mg, 0.028 mmol). $^1$H NMR (500 MHz, DMSO-$d_6$) 11.72 (s, 1H), 8.46 (d, J=7.8 Hz, 1H), 8.20 (d, J=7.8 Hz, 1H), 8.14 (s, 1H), 7.92 (t, J=7.6 Hz, 1H), 7.79 (t, J=7.7 Hz, 1H), 7.73 (s, 1H), 7.67 (d, J=8.0 Hz, 1H), 7.51 (d, J=8.1 Hz, 1H). $^{13}$C NMR (151 MHz, DMSO) 179.21, 157.13, 151.39, 147.50, 145.95, 140.55, 134.54, 133.32, 132.78, 130.04, 129.02, 128.76, 127.35, 125.95, 125.00, 124.21, 122.72, 117.87, 117.62, 102.27. HRMS (ES+) calc'd for $C_{20}H_{12}BrN_2O_8S_2$ (M+H) 549.9140 m/z. Found 549.9127. Intermediate VIIII (8 mg, 0.014 mmol) was dissolved in anhydrous DMF (2 ml) to which anhydrous DIPEA (12.2 ul, 0.07 mmol) and linker ABT-1 (0.014 g, 0.028 mmol) were added and the solution allowed to stir for 5 hr at 70° C. The reaction mixture was concentrated under a stream of nitrogen, filtered and purified directly by C18 HPLC chromatography (20-100% $H_2O$/MeOH, ammonium formate buffer pH4/30 min). The obtained fractions were pooled and lyophilized resulting in pure 6-ABT-1 isolated in 42% yield as the ammonium formate salt (5.7 mg, 0.0058 mmol) as an orange-reddish solid (accurate yield determination confirmed by UV using an extinction coefficient of 17,000 for the DNP unit). $^1$H NMR (500 MHz, DMSO-$d_6$) 11.71 (s, 1H), 8.93 (t, J=5.4 Hz, 1H), 8.79 (d, J=2.6 Hz, 1H), 8.45 (d, J=8.0 Hz, 1H), 8.24 (brs, 1H), 8.21 (dd, J=9.6, 2.6 Hz, 1H), 8.13 (m, 2H), 7.86 (t, J=5.4 Hz, 1H), 7.81 (t, J=7.5 Hz, 1H), 7.69 (t, J=7.6 Hz, 1H), 7.62 (d, J=8.1 Hz, 1H), 7.55 (d, J=8.2 Hz, 1H), 7.19 (d, J=9.7 Hz, 1H), 6.38 (s, 1H), 4.64 (brs, 2H), 4.18 (brs, 2H), 3.58-3.37 (m, 14H), 3.10 (m, 2H), 2.53 (m, 1H), 1.92-1.80 (m, 4H), 1.65-1.54 (m, 4H). $^{13}$C NMR (126 MHz, DMSO) 175.29, 172.59, 154.22, 152.01, 148.64, 145.44, 144.72, 140.10, 135.64, 135.00, 133.70, 131.70, 130.39, 129.93, 128.88, 128.30, 126.89, 126.27, 124.10, 123.99, 123.68, 122.10, 119.46, 115.58, 97.18, 96.81, 70.15, 69.95, 68.74, 68.45, 52.24, 42.73, 41.46, 36.19, 29.66, 28.67, 27.97, 24.17. HRMS (ES+) calc'd for $C_{42}H_{46}N_7O_{16}S_2$(M+H) 968.2442 m/z. Found 968.2420.

Scheme S6. Synthesis of derivatives 6-ABT-1, 6-ABT-2, 6-ABT-3

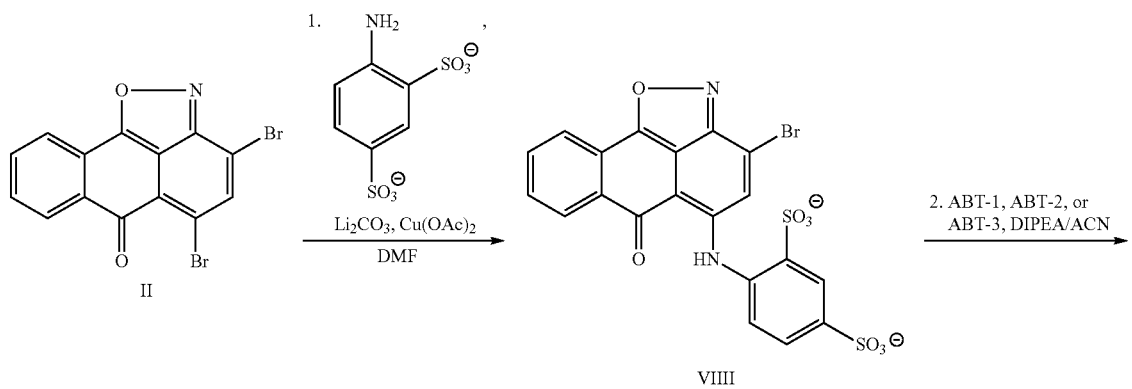

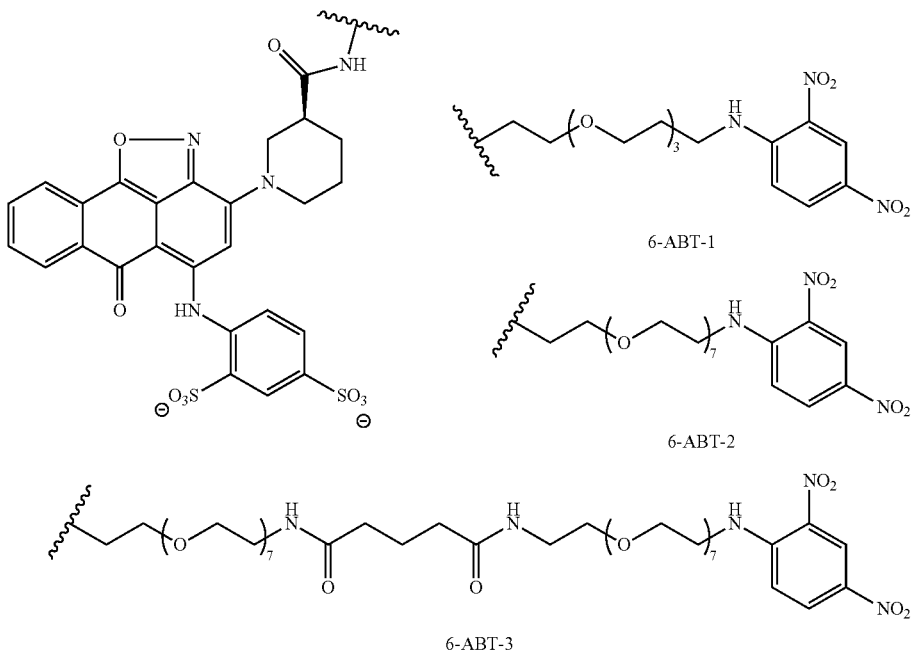

Synthesis of ARM-U2 Derivative 6-ABT-2

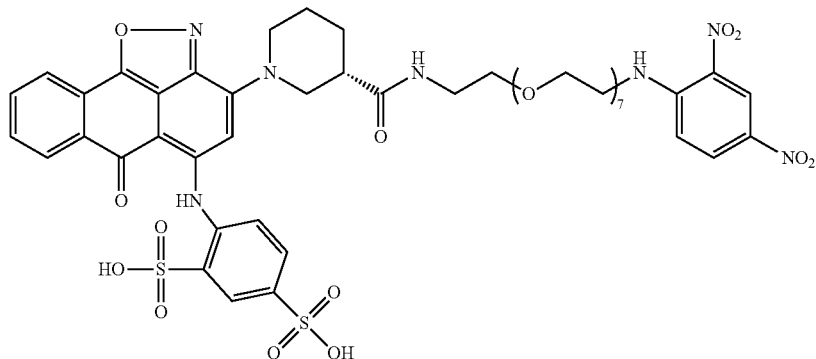

ARM-U2 derivate 6-ABT-2 was synthesized and purified as described above for 6-ABT-1 only intermediate VIIII (8 mg, 0.014 mmol) was coupled to linker ABT-2 (9 mg, 0.014 mmol) as opposed to ABT-1 resulting in the isolation of 6-ABT-2 in 35% yield as the ammonium formate salt (0.0049 mmol, 5.5 mg). $^1$H NMR (600 MHz, DMSO-$d_6$) 11.71 (s, 1H), 8.81 (m, 2H), 8.45 (d, J=8.0 Hz, 1H), 8.21 (dd, J=9.6, 2.6 Hz, 1H) 8.13 (m, 2H), 8.00 (t, J=5.5 Hz, 1H), 7.81 (t, J=7.5 Hz, 1H), 7.70 (t, J=7.6 Hz, 1H), 7.62 (d, J=9.6 Hz, 1H), 7.55 (d, J=8.2 Hz, 1H), 7.26 (d, J=9.6 Hz, 1H), 6.38 (s, 1H), 4.63 (brs, 2H), 4.17 (brs, 2H), 3.73-3.08 (m, 32H), 2.58 (m, 1H), 1.87 (dd, J=30.1, 11.0 Hz, 2H), 1.74-1.66 (m, 1H), 1.59 (m, 1H). $^{13}$C NMR (151 MHz, DMSO) 175.29, 172.90, 164.96, 154.22, 151.91, 148.75, 148.59, 145.39, 144.55, 139.96, 135.65, 135.19, 133.65, 131.75, 130.28, 129.92, 128.94, 128.28, 126.93, 126.20, 124.07, 123.92, 123.72, 122.14, 119.43, 116.14, 97.18, 96.78, 70.17, 69.38, 68.62, 55.39, 43.05, 40.79, 38.87, 28.10, 24.18. HRMS (ES+) calc'd for $C_{48}H_{58}N_7O_{20}S_2$(M+H) 1116.3178 m/z. Found 1116.3281.

Synthesis of ARM-U2 Derivative 6-ABT-3

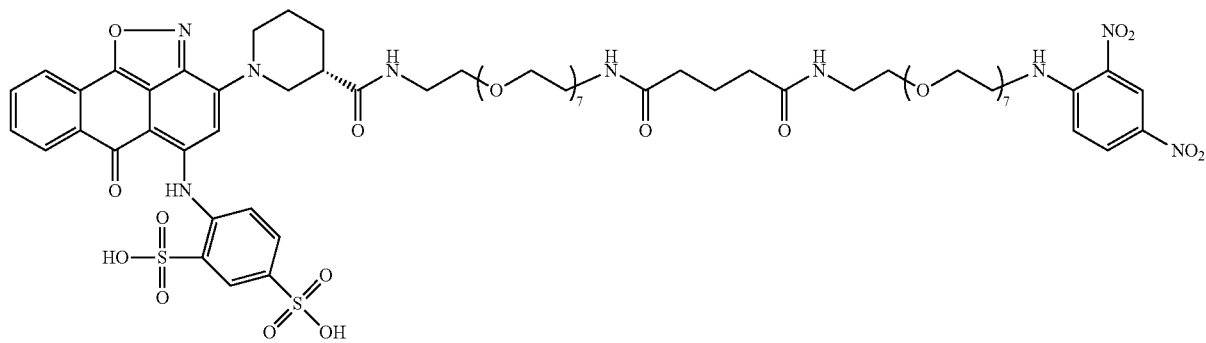

ARM-U2 derivative 6-ABT-3 was synthesized and purified exactly as described above for ARM-U2 6-ABT-1 only intermediate VIIII (8 mg, 0.014 mmol) was coupled to linker ABT-3 (28 mg, 0.025 mmol) as opposed to ABT-1 resulting in the isolation of 6-ABT-3 in 27% yield as the ammonium formate salt (6 mg, 0.0038 mmol). $^1$H NMR (600 MHz, DMSO-$d_6$) 11.71 (s, 1H), 8.84 (d, J=2.7 Hz, 1H), 8.46 (d, J=7.9 Hz, 1H), 8.31 (br s, 2H), 8.24 (dd, J=9.6, 2.7 Hz, 1H), 8.14 (d, J=7.8 Hz, 1H), 8.13 (d, J=2.1 Hz, 1H), 8.01 (t, J=5.6 Hz, 1H), 7.82 (m, 2H), 7.71 (t, J=7.6 Hz, 1H), 7.62 (d, J=8.2 Hz, 1H), 7.56 (d, J=8.2 Hz, 1H), 7.28 (d, J=9.7 Hz, 1H), 6.39 (s, 1H), 4.63 (br s, 2H), 4.19 (br s, 2H), 3.69-3.17 (m, 64H), 2.56 (s, 1H), 2.03 (t, J=7.5 Hz, 4H), 1.91-1.83 (m, 2H), 1.73-1.64 (m, 3H), 1.63-1.59 (m, 1H). $^{13}$C NMR (151 MHz, DMSO) 175.32, 172.89, 172.22, 165.01, 154.23, 151.97, 148.79, 148.63, 145.42, 144.64, 140.05, 135.65, 135.27, 133.70, 131.73, 130.30, 130.04, 128.91, 128.30, 126.90, 126.23, 124.12, 123.95, 123.71, 122.13, 119.47, 116.14, 97.24, 96.81, 70.23, 69.55, 68.68, 52.14, 49.17, 43.09, 42.53, 38.86, 35.10, 28.07, 24.18, 21.93. HRMS (ES+) calc'd for $C_{69}H_{98}N_9O_{29}S_2$(M+H) 1580.5912 m/z. Found 1580.6155.

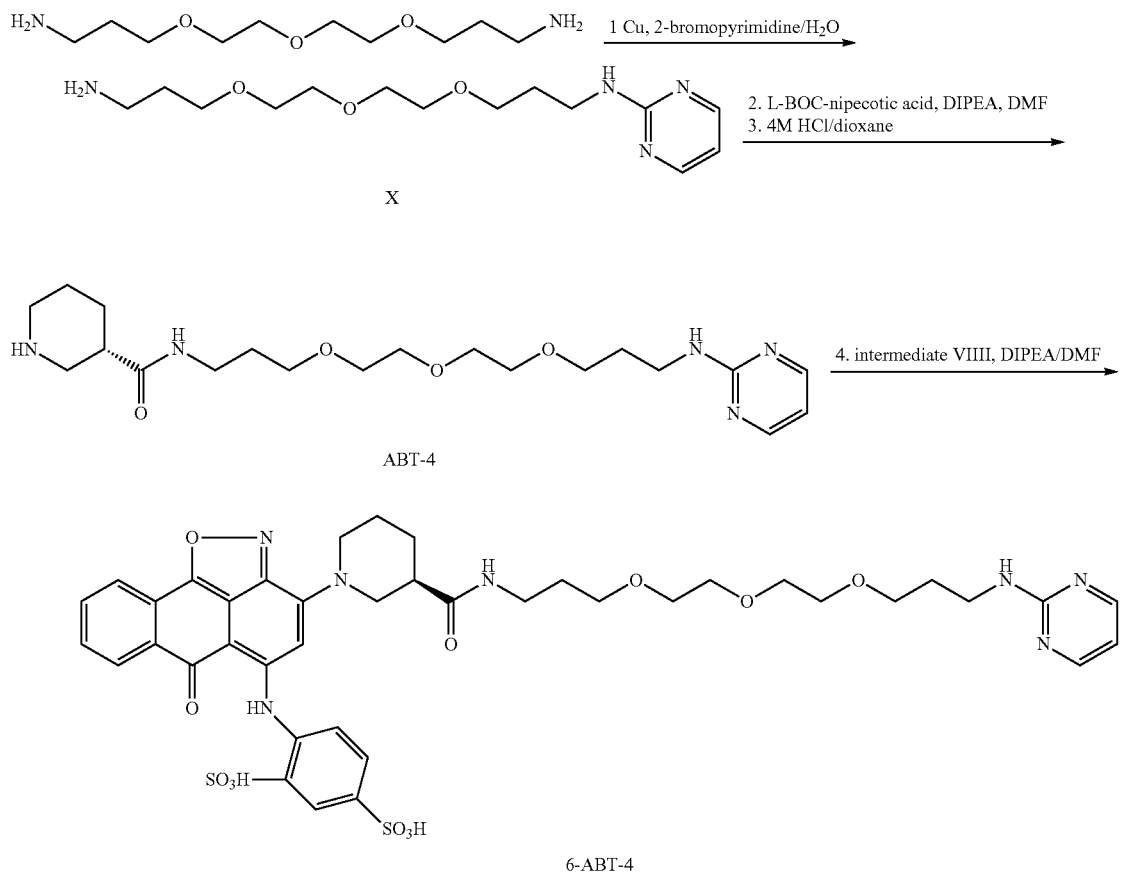

Synthesis DNP Substituted Analog 6-ABT-4
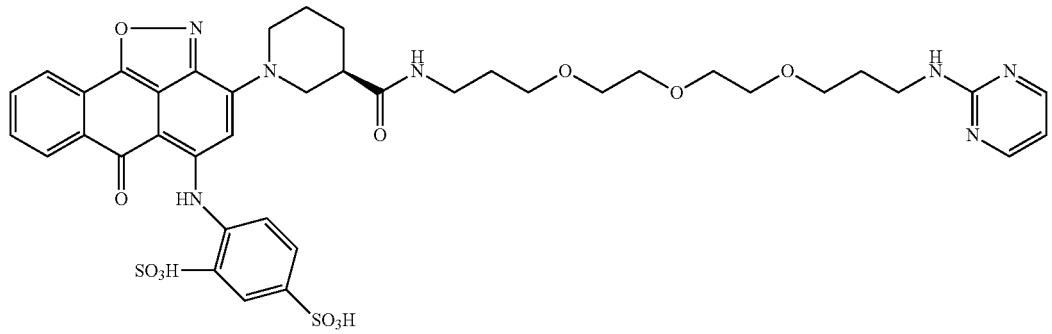 [SMILES: O=C1c2ccccc2-c2onc3c(N4CCC[C@@H](C(=O)NCCCOCCOCCOCCCNc5ncccn5)C4)cc(Nc4ccc(S(=O)(=O)O)cc4S(=O)(=O)O)c1c23]

Synthesis an analog of derivative 6-ABT-1 where the DNP moiety is substituted by pyrimidine expected and later shown experimentally to have no affinity for anti-DNP antibodies was initiated by coupling of 2-bromopyrimidine to the diamine 3,3'-((oxybis(ethane-2,1-diyl))bis(oxy))bis(propan-1-amine) using Hartwig-Buchwald Pd(0) coupling conditions however this was unsuccessful likely due to deactivating chelation of the amine ligand to palladium. Alternative Ullman-type conditions were employed by dissolving the diamine (100 mg, 0.45 mmol) and 2-bromopyrimidine (57 mg, 0.36 mmol) in 2 ml deI water open to atmosphere followed by the addition of copper metal (1.4 mg, 0.023 mmol). Upon heating for 1 hr at 100° C. the solution turned a bluish-green and the reaction was quenched using 1M HCL. The solution was concentrated and purified by ISCO C18 chromatography to yield the pyrimidine-monoamine linker intermediate X in 80% yield as a slightly yellowish oil (86 mg, 0.29 mmol) $^1$H NMR (500 MHz, DMSO-$d_6$) 8.42 (s, 2H), 8.24 (d, J=4.7 Hz, 2H), 7.08 (t, J=5.4 Hz, 1H), 6.53 (t, J=4.7 Hz, 1H), 3.54-3.42 (m, 10H), 3.29 (q, J=6.6 Hz, 4H), 2.77 (t, J=7.2 Hz, 2H), 1.73 (dp, J=13.7, 6.5 Hz, 4H). HRMS (ES+) calc'd for $C_{14}H_{27}N_4O_3$ (M+H) 299.2005. Found 299.2011. Intermediate X (86 mg, 0.29 mmol) was coupled to Boc-L-nipecotic acid and deprotected as described above for linker ABT-1 to yield ABT-4 in quantitative yield (118 mg, 0.29 mmol) and used directly in the next step. The di-bromo intermediate VIIII (8 mg, 0.014 mmol) was coupled to linker ABT-4 (11.4 mg, 0.028 mmol) and purified exactly as described above for 6-ABT-1 resulting in the isolation of 6-ABT-4 in 43% yield (5.2 mg, 0.006 mmol) $^1$H NMR (500 MHz, DMSO-$d_6$) 11.70 (s, 1H), 8.43 (d, J=8.1 Hz, 1H), 8.26 (d, J=4.6 Hz, 2H), 8.14 (d, J=12.6 Hz, 2H), 7.86 (t, J=5.4 Hz, 1H), 7.81 (t, J=7.5 Hz, 1H), 7.69 (t, J=7.6 Hz, 1H), 7.62 (d, J=9.9 Hz, 1H), 7.55 (d, J=8.2 Hz, 1H), 7.07 (brs, 1H) 6.55 (t, J=4.8 Hz, 1H), 6.37 (s, 1H), 4.62 (brs, 2H), 4.18 (brs, 2H), 3.51-3.35 (m, 10H), 3.26 (m, 4H), 3.16-3.04 (m, 2H), 1.92-1.78 (m, 1H), 1.71 (t, J=10.0 Hz, 4H), 1.65 (m, 4H). $^{13}$C NMR (151 MHz, DMSO) 175.30, 172.60, 163.47, 158.09, 154.26, 152.01, 148.65, 145.47, 144.63, 139.97, 135.67, 133.67, 131.75, 128.92, 128.28, 126.95, 126.26, 124.12, 123.77, 122.16, 119.46, 110.11, 97.17, 96.80, 70.17, 69.94, 68.64, 68.42, 52.22, 49.16, 42.70, 38.49, 36.16, 29.66, 29.42, 28.00, 24.17. HRMS (ES+) calc'd for $C_{40}H_{46}N_7O_{12}S_2$(M+H) 880.2568 m/z. Found 880.2538.

Results and Discussion

Computation.

Inspiration for the development of the target binding terminus (TBT) of ARM-U2 came from studies of literature reported anthroquinone derived compound IPR-803 (T. Mani, S. Meroueh et al) with triple digit nM affinity for uPAR. Computational modeling studies were conducted to assess the optimal location for installing the antibody recruiting motif onto the anthroquinone when complexed to uPAR (FIG. 2). Computational uPAR docking studies suggested that functionalization of the IPR-803 core with a dinitrophenyl-trioxa-1,13-tridecanediamine antibody binding terminus (ABT) at position 2 of ring C (ARM-U2 1-ABT-1, FIG. 4, Scheme 1) would allow for the antibody recruiting motif to remain solvent exposed available to bind endogenous anti-DNP antibodies in vivo and not interfere with uPAR binding affinity. Computational docking studies were also conducted to guide the development of higher affinity binding ARM-U2 derivatives by docking compounds into the uPA binding site of uPAR where IPR-803 interactions with "hot spot" residues are proposed to occur (T. Mani, S. Meroueh et al).

The above process was repeated for derivatives differing in the display, density, and type of negative charge about the aniline moiety substituted at ring C of IPR-803 (FIG. 4, Scheme 1, FIG. 8, Table 1). Computational docking of designed ARM-U2 derivatives with an additional carboxyl moiety substituted at the aniline ring ARM-U2 2-ABT-1 or a single meta carboxyl to meta-sulfonate substitution ARM-U2 5-ABT-1 predicted no increase in uPAR binding affinity (See FIG. 4, Scheme 1, FIG. 8, Table 1). However derivatives with the carboxyl moiety extended further from the aniline ring (3-ABT-1 and 4-ABT-1) and substitution of a single meta-sulfonate for two sulfonates at the ortho and para position 6-ABT-1 were predicted to experience significant gains in binding energy (See FIG. 4, Scheme 1, FIG. 8, Table 1). These increases are predicted by computation to be due to a gain in H-bonding capability with Arg-53 and Lys-50.

The results of the computational studies supported the chemical synthesis of ARM-U2 derivatives with the ABT appended to the core of IPR-803 at position 2 of ring C for further in vitro uPAR binding studies. The results of the docking experiments also suggested that uPAR-binding affinity may be tunable by optimizing compound interactions with hot-spot basic residues in the uPA-binding pocket (1-ABT-1 vs 4-ABT-1 and 6-ABT-1, FIG. 8, Table 1). The bi-functional TBT and ABT containing ARM-U2 derivatives that were docked to uPAR were then chemically synthesized to evaluate in subsequent in-vitro uPAR binding assays Longer ABTs consisting of longer PEG-derived building blocks were synthesized chemically and incorporated into additional ARM-U2 derivatives in attempts to optimize antibody binding affinity.

Competitive ELISA uPAR Binding Assays.

The affinity of ARM-U2 derivatives differing in both the length of the DNP-linker substituted at position 2 of ring C and the display of negative charge density (FIG. 8, Table 1) for uPAR were assayed using a competitive ELISA binding assay. The assay involves the immobilization of urokinase, a natural high affinity ligand for uPAR followed by the addition of a fixed concentration of recombinant uPAR protein and increasing concentrations of ARM-U2 which competes with urokinase for binding to the uPA binding site of uPAR. Following several washing steps, the amount of uPAR bound is quantified by a biotinylated anti-uPAR antibody and avidin-HRP and can be fit to a competitive binding model allowing for the extraction of the uPAR/ARM-U2 $K_d$.

All ARM-U2 derivatives were observed to bind to uPAR selectively at the uPA binding site with single to triple digit nM affinity. These results confirmed the previous computational predictions that installing the ABT at position 2 of ring C of the anthroquinone core enabled for ARM-U2 parent derivative 1-ABT-1 to retain the expected triple digit nanomolar binding affinity for uPAR (as reported in the literature for parent compound IP-803 (Table 1, FIG. 8). Longer linker-containing derivatives (ABT-2 and ABT-3) showed an increased binding affinity compared to their shorter trioxa-1,13-tridecanediamine linker-containing counterpart (ABT-1) however this is likely attributed to additional interactions at a distal arene binding site on uPAR.

The uPAR-binding affinities calculated for compounds 3-ABT-1 and 4-ABT-1 which have the carboxylic acid extended further from the aniline moiety and predicted to bind uPAR with higher affinity by computation were shown to have a modest increase in affinity relative to parent ARM-U2 derivative 1-ABT-1. The di-acid derivative 2-ABT-1 and mono-sulfonate 5-ABT-1 also showed no increase in uPAR-binding affinity relative to parent ARM-U2 1-ABT-1. This observation suggests that the interactions with uPAR are not only electrostatic in nature but could be highly directional. Derivative 6-ABT-1 however, containing an ortho and para sulfonate showed a significant increase in affinity relative to 1-ABT-1. The increase in binding affinity observed for 6-ABT-1 is likely the result of its ability to make specific H-bonds with Arg-53 and Lys 50 as predicted by docking studies in contrast to 1-ABT-1. This is further supported by the fact that 6-ABT-1 binds uPAR with significantly higher affinity than double carboxylate derivative 2-ABT-1 which cannot be explained by long range acting electrostatic interactions alone but can be explained considering the known stronger H-bonding and higher enthalpy of interaction that occurs between guanidinium functionalities and sulfonate groups compared to carboxylate groups.

From these in vitro binding studies, we can conclude that computational docking studies accurately predicted compounds with increasing uPAR binding affinity in addition to the correct location to substitute with the ABT to avoid disruption of uPAR binding. We can also conclude that an anthroquinone derived small molecule is an effective substitute for the large uPA target binding motif on ARM-U and that ARM-U2 can potentially recruit antibodies to the surface of uPAR-expressing cancer cells inducing cellular phagocytosis and cytotoxicity at single to triple digit nanomolar concentrations.

uPAR/6-ABT-1 Crystallization Studies

Figure 2:
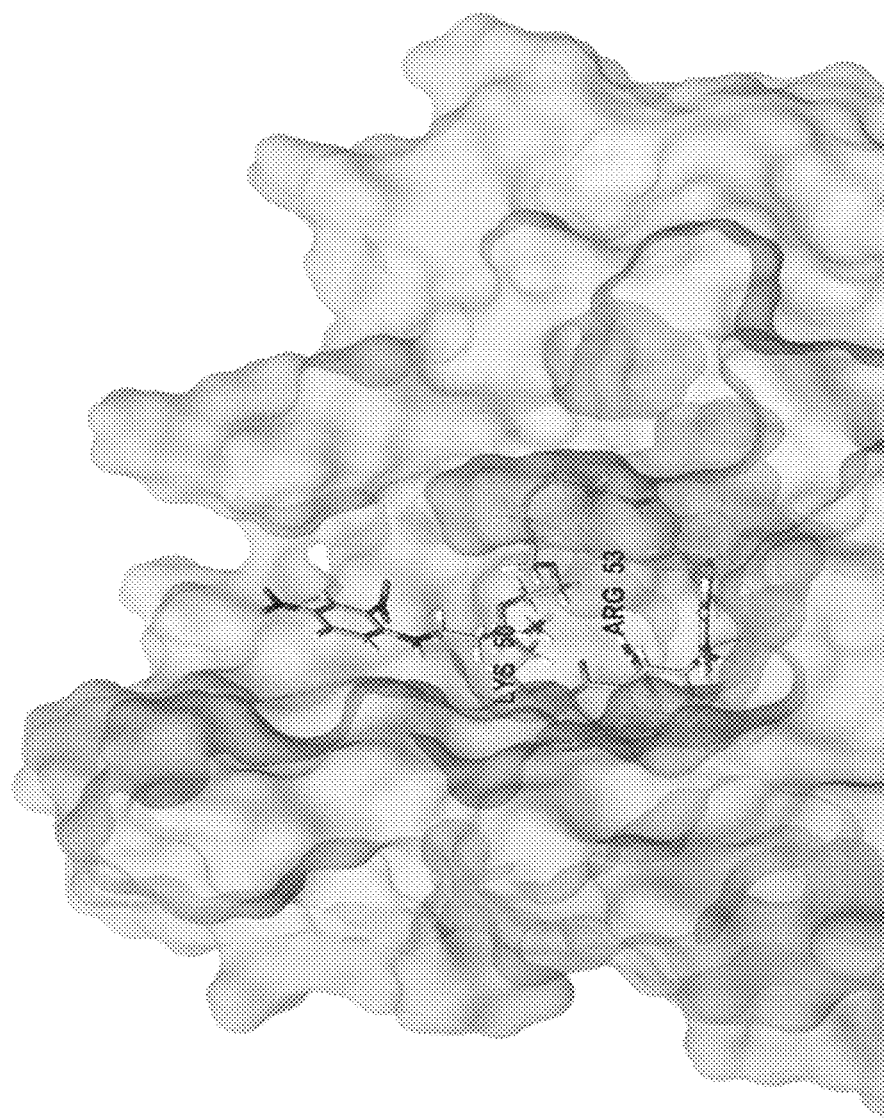
FIG. 2 shows computational docking studies of parent compound ARM-U2 1-ABT-1 in the uPA binding site of uPAR illustrating both the interaction between 1-ABT-1 and uPAR hotspot residues as well as the solvent exposed positioning of the ▰ group.
Figure 3:
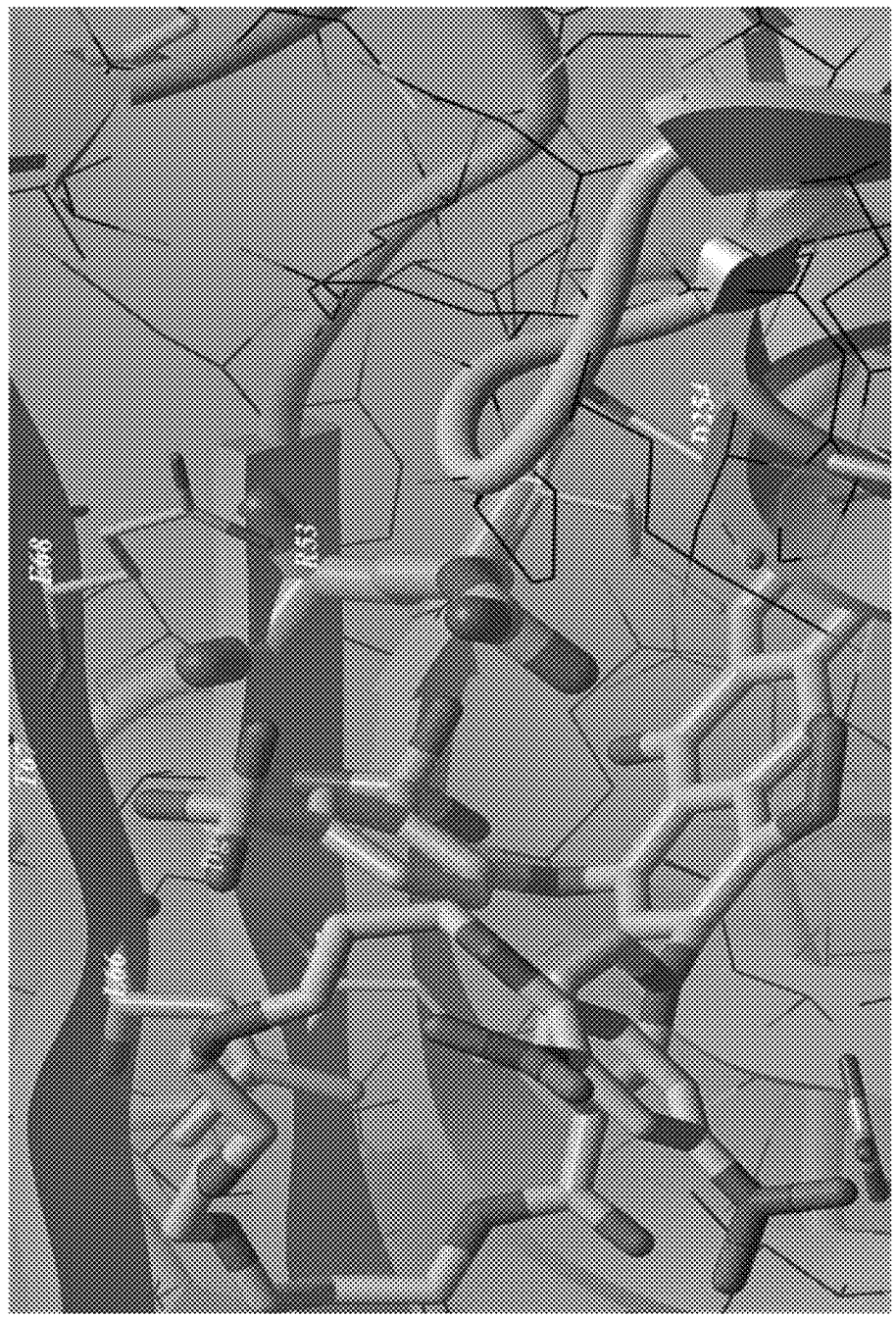
FIG. 3 shows the crystal structure of ARM-U2 6-ABT-1 complexed to UPAR at the UPA binding site making a key contract with Arg-53 through its sulfonate groups.

To reinforce the results of our competitive binding assays in that 6-ABT-1 binds to the uPA binding site of uPAR via the uPA binding site and support our hypothesis that the increase in affinity is due to specific interactions with cationic hotspot residues within the binding pocket of uPAR, we investigated the binding of 6-ABT-1 to crystallized uPAR protein in collaboration with Dr M. Huang who soaked the compound into pre-crystallized uPAR. We observed that 6-ABT-1 binds to uPAR at the uPA binding interface with the antibody recruiting motif solvent exposed while making a specific contact with Arg-53 previously reported to be a hotspot residue engaged by urokinase (FIG. 2). This result also suggests a potential dual mode of action as an anti-cancer therapeutic acting as an antagonist of the oncogenic uPA-uPAR interaction in addition to acting as an antibody-recruiting molecule against uPAR.

Antibody Recruiting Cellular Assays

Next, we tested the ability of ARM-U2 derivatives to recruit anti-DNP antibodies to the surface of A-172 and B-16 cancer cells over-expressing uPAR. These assays involved the incubation of ARM-U2 derivatives with target cancer cells followed by the addition of biotinylated anti-DNP antibodies and streptavidin-AlexaFluor conjugates. After several washing steps, the amount of bifunctional ARM-U2 compound bound simultaneously to both the cell surface and anti-DNP antibodies was detected using flow cytometry by observing shifts in FL-2 and FL-3 fluorescence. These experiments were also conducted on both B16+uPAR cell lines and B16–uPAR cell lines in addition to studies on A172 cells in the presence and absence of exogenously added competitor uPAR to assess selective binding to the cell surface via cell surface uPAR.

Derivatives 1 to 6-ABT-1, and longer ABT containing variants 1-ABT-2/3 and 6-ABT-2/3 all demonstrated the ability to survive multiple washing steps and simultaneously bind to both anti-DNP antibodies and cell surface uPAR on A172 cells with antibody recruiting capability declining with increased linker length. High affinity uPAR binding derivative 6-ABT-1 recruited antibodies significantly better than the other ABT-1 derivatives on A172 cells and antibody recruitment could be disrupted by adding exogenous competitor uPAR. ARM-U2 6-ABT-1 also recruited anti-DNP antibodies to the surface of B-16+uPAR cells but failed to do so with B-16–uPAR cells (FIG. 9A, B).

From these results we can conclude the following:
1. The location on the anthroquinone chosen for linker substitution and length of ABT-1 appears to be effective for engaging in interactions with both cell surface uPAR and anti-DNP antibodies confirming its solvent exposed environment accordance with predictions made from computation;
2. The observed trend of decreasing antibody-recruiting capability with increasing linker length further supports the argument for an interaction between the antibody recruiting motif and a distal arene binding site on uPAR becoming less available for anti-DNP antibody interactions while engaged in binding uPAR contributing to the higher uPAR binding affinity observed. (FIG. 8, Table 1)
3. The ability of exogenously added uPAR to disrupt the antibody recruiting capability of 6-ABT-1 supports the selective binding of 6-ABT-1 to cell surface uPAR in the presence of the complex cellular meilleur;
4. This fact is further supported by the selective antibody recruiting mediated by 6-ABT-1 to B16+uPAR cell lines and not B16–uPAR (FIG. 9A,B);
5. The ability of all the derivatives to survive the multiple washing steps required in the antibody-recruiting flow cytometry assay combined with the knowledge that 6-ABT-1 recruits anti-DNP antibodies much more effectively than the other derivatives despite identical antibody-recruiting motifs, supports its significantly higher uPAR binding affinity with an expected dissociation half life on the order of 1-2 min enabling for more compound to remain bound to the cells, recruit antibodies and survive washing steps.

ARM-U2 Mediated Antibody Dependent Cellular Phagocytosis (ADCP)

ADCP experiments carried out via a dual channel flow cytometry assay and were performed by measuring the % phagocytosis of A172 human glioblastoma cells by IFN-gamma primed U937 macrophage effector cells each stained with FL-1 and FL-4 dyes respectively giving rise to double positive FL-1 and FL-4 fluorescence shifts accompanying phagocytosis. These assays were performed in the presence and absence of exogenously added anti-DNP antibodies and various concentrations of each ARM-U2 derivative. Control experiments were also performed to confirm that cellular phagocytosis is occurring and is dependent on ARM-U2 binding cell surface uPAR by 1. Performing out competitions with exogenous uPAR,
2. Performing out-competitions with 6-ABT-4 which should bind uPAR but not anti-DNP antibodies
3. Performing ADCP at 4 degrees celcius where phagocytosis cannot occur and
4. Amnis microscopic analysis of double positives identified in the ADCP assay to undergo 6-ABT-1 dependent phagocytosis.

ADCP experiments were also performed on B16+uPAR and −uPAR cell lines as an isogenic control to assess selectivity for cell surface uPAR. All of the ARM-U2 derivatives tested were observed to induce U937 monocyte-mediated phagocytosis of A172 glioblastoma cells overexpressing uPAR at ARM-U2 concentrations spanning single to triple digit nanomolar concentrations. Increasing linker length was observed to result in a decrease in ADCP efficacy when comparing 1-ABT-1 vs 1-ABT-2/3 as well as 6-ABT-1 vs 6-ABT-2/3. The longer linker ABT-2 and ABT-3 functionalized ARM-U2 derivatives with lower antibody recruiting capability than their respective ABT-1 functionalized counterparts, showed lower ADCP efficacy in accordance with our hypothesis that longer antibody recruiting motifs are capable of binding to a distal site on uPAR resulting in an increased binding affinity however less available for interactions with anti-DNP antibodies. Increasing the negative charge density (2-ABT-1) and further extending the carboxylic acid moiety (3-ABT-1, 4-ABT-1) showed no increase in efficacy or potency in ADCP compared to compounds 1-ABT-1 in accordance with the similar binding affinities calculated for uPAR binding and similar antibody recruiting capability observed by flow cytometry.

The lack of effect of increasing the negative charge density at the aniline substituted at ring C (2-ABT-1 vs 1-ABT-1) reinforces the hypothesis that ARM-U2 interactions with the basic residues in the uPA binding pocket are not purely electrostatic in nature and are likely mediated through specific H-bonding. Compound 5-ABT-1 containing one meta-substituted sulfonate showed no increase in % phagocytosis compared to the mono carboxylic acid derivative 1-ABT-1 in accordance with its relatively similar uPAR binding affinity and antibody recruiting capability. The fact that the % phagocytosis does not change significantly with the di-acid or mono-sulfonate derivatives (2-ABT-1 and 5-ABT-1) further argues against phagocytosis occurring as a result of non-specific hydrophobic or electrostatic interactions with the cell surface, since the additional negative charge density on these compounds would be expected to cause an increase in efficacy if these compounds bound to basic cell surface proteins and a decrease in efficacy if they interacted hydrophobically with the cell surface. Double sulfonate-substituted compound 6-ABT-1 with sulfonates at the ortho and para positions however showed a significant increase in potency and efficacy compared to the mono-acid derivative 1-ABT-1 as predicted by computation.

As ARM-U2 derivative 6-ABT-1 bound to uPAR with the highest affinity (FIG. 8, Table 1), and was shown to recruit anti-DNP antibodies most effectively (FIG. 9A,B), it follows that this derivative shows the highest efficacy and potency of all the ARM-U2 derivatives tested in ADCP (FIG. 9C). The sharp increase in % phagocytosis observed for 6-ABT-1 between 10 and 50 nM corresponds well with the calculated dissociation constant of 12 nM and supports a specific uPAR-dependent phagocytic response (FIG. 9C). The high selectivity of 6-ABT-1 and the dependence of its efficacy in ADCP on cell surface uPAR is demonstrated by the ability to disrupt phagocytosis by the addition of exogenous uPAR which competes with cell surface uPAR for binding 6-ABT-1 (FIG. 9C). This is further demonstrated by the ability to disrupt phagocytosis by the addition of 6-ABT-4 which can bind uPAR but not anti-DNP antibodies confirming that the efficacy of 6-ABT-1 is dependent on a specific uPAR binding interaction and not a non-specific interaction with the cell surface which would be unsaturatable and unable to be competed off by the addition of 6-ABT-4 (FIG. 9C). The bell shaped appearance of the phagocytosis efficacy dependence on 6-ABT-1 concentration is typical of the well documented prozone effect and is a further indication of 6-ABT-1 selectivity for cell surface uPAR (FIG. 9C). The downward slope on the right hand side of the bell shaped curve arises at high concentrations of 6-ABT-1 (>100 nM) due to a competition for limited anti-DNP antibody between cell surface bound and unbound 6-ABT-1 and would not occur of 6-ABT-1 bound to the cell surface non-specifically and therefore in a non-saturatable manner.

The inventors hypothesize that the increased efficacy and selectivity of 6-ABT-1 relative to the other ARM-U2 derivatives studies is primarily due to its significantly enhanced affinity for uPAR and is also in part due to its high negative charge density which increases the monodispersion of the compound in aqueous media while decreasing the amount of non-specific binding that can potentially occur in the negatively charged environment of the cell surface. The efficacy of 6-ABT-1 is confirmed to be cellular phagocytosis by the demonstration that relatively few double positives are observed in the ADCP assay at 4 degrees celcius and by Amnis analysis of ADCP samples of 6-ABT-1 at 37 degrees celcius which illuminates the microscopic engulfment of stained A172 target cells by stained u937 monocytes (FIG. 9D). The significant increase in ADCP efficacy and potency observed for the disulfonate-containing ARM-U2 derivative 6-ABT-1 is again supportive of stronger interactions with basic residues in the uPA-binding site of uPAR, including Arg-53 supported by crystallography in addition to lysine 50 and glutamic acid 68 implicated by computational docking experiments.

Taken together, the inventors have shown that computationally guided ARM-U2 design enabled for significant gains in uPAR binding affinity to be achieved through the facile synthetic tuning of negative charge display and density about the functionalized aniline substituted at position 4 of ring C of the anthroquinone scaffold, (FIG. 4, Scheme 1, FIG. 8, Table 1).

ARM-U2 Mediated Antibody Dependent Monocytic u937 Cell Release of Inflammatory Cytokines Derivative 6-ABT-1 was shown through a multi-cytokine immobilized ELISA to stimulate a higher release of IL-8 by u937 cells through the recruitment of anti-DNP antibodies to the surface of A-172 cells which subsequently stimulate u937 monocytes presumably through Fc gamma receptor clustering. IL-8 is primarily released by monocytes and macrophages early in the innate immune response upon recognition of a foreign antigen which initiates the immune cascade.

Figure 10:
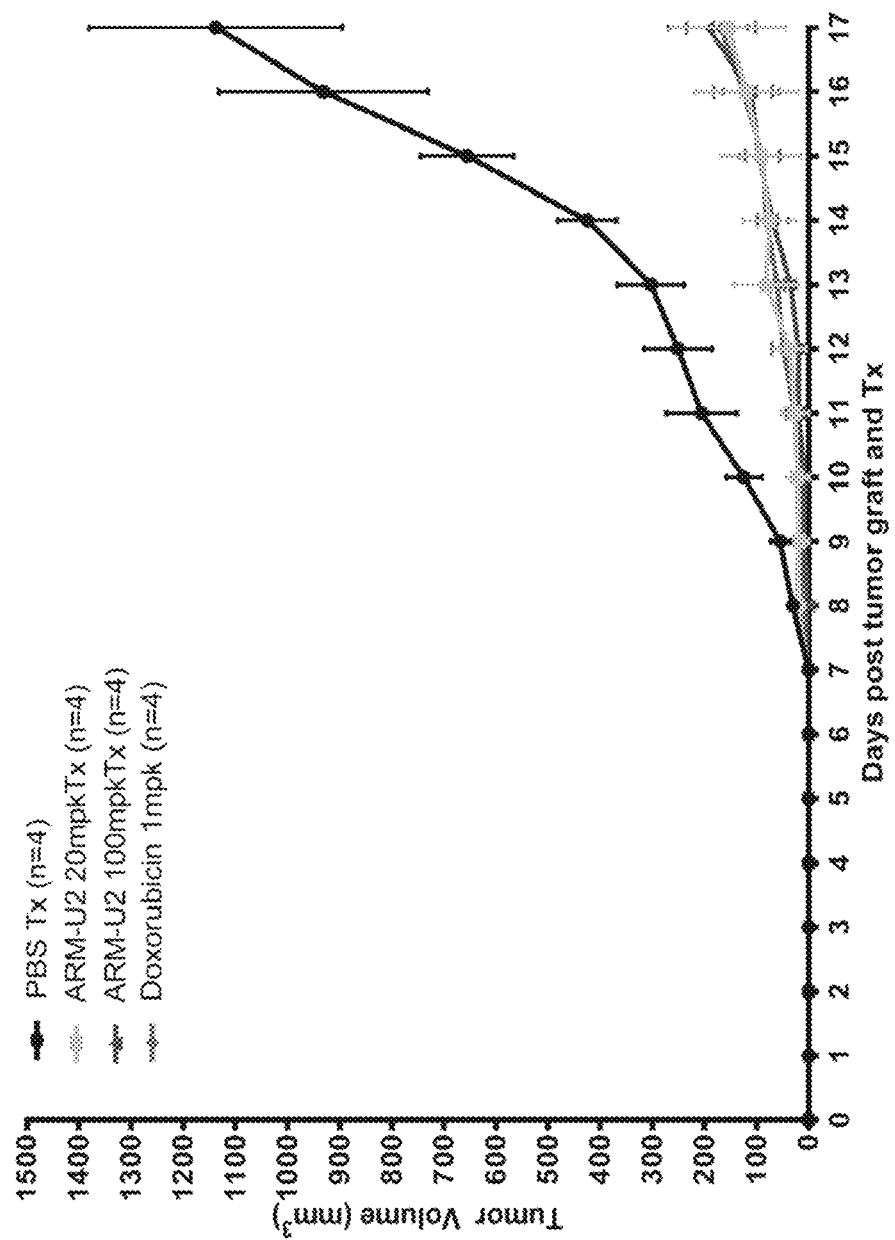
FIG. 10 shows in vivo efficacy studies of ARM-US 6-ABT-1 in an allograft mouse B16 tumor model. Black-line PBS administered control cohort, other lines indicate ARM-U2 (at two different concentrations) or doxorubicin administered (ip, 1 mpk) cohort.

ARM-U2 Mediated Inhibition of Tumor Progression in an Allograft Mouse B16 Tumor Model IP injections of 6-ABT-1 over the course of 17 days was shown to significantly halt tumor progression relative to the PBS control in laboratory test animals (mice). After 17 days of treatment with 6-ABT-1 or PBS, un-treated mice were observed to possess significant tumor burden reaching mean tumor volumes of 1000 mm$^3$ at which point they were sacrificed as dictated by standard ethics protocols where 6-ABT-1 treated mice in two separate cohorts given two different dosing concentrations possessed tumors with an average volume of approximately 200 mm$^3$ overlapping with that observed for the doxorubicin treated cohort (FIG. 10).

Figure 11:
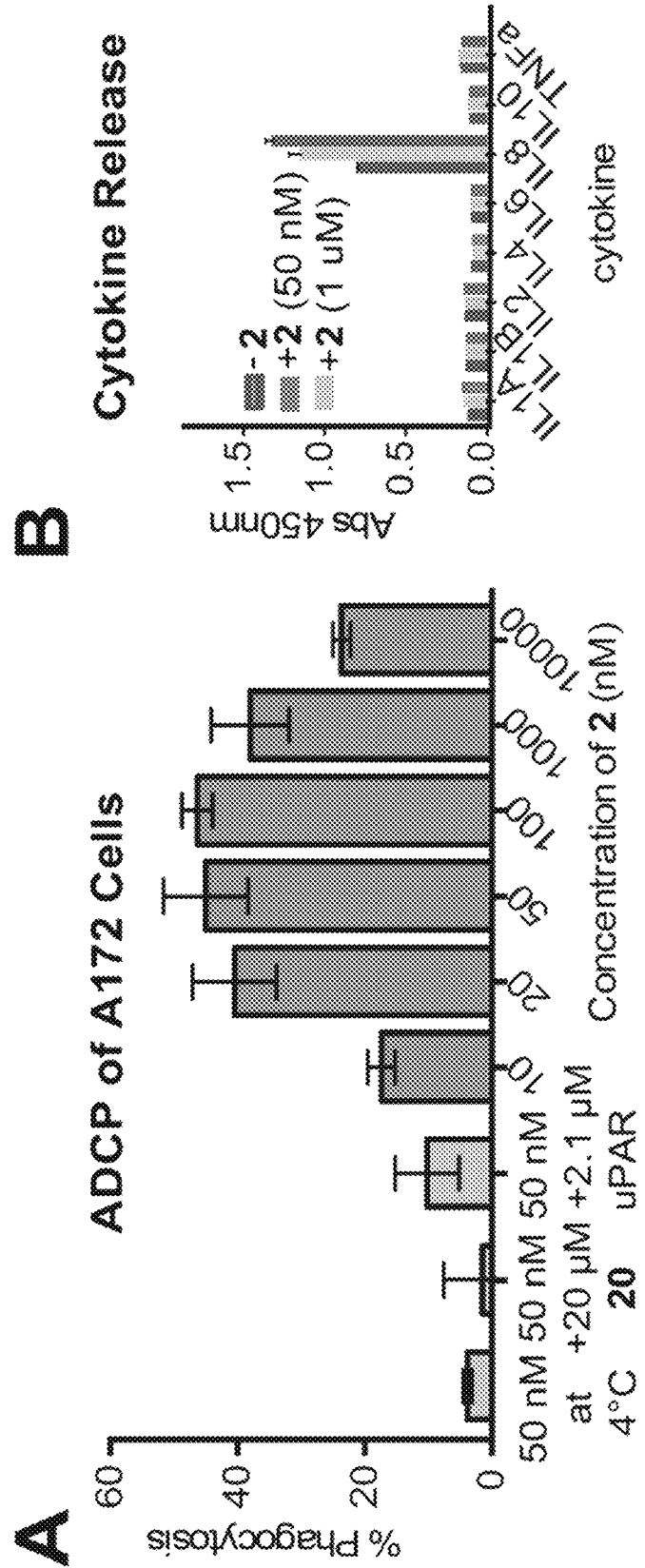
FIG. 11 demonstrates the in vitro efficacy and potency of 6-ABT-1 in immune effector cell assays using A172 glioblastoma cells. (A) 6-ABT-1 concentration-dependent phagocytosis of A172 glioblastoma cells in the presence of anti-DNP antibodies (133 nM). Studies were conducted at both 37° C. or 4° C. and in the presence or absence of either exogenous uPAR or derivative 20. (B) 6-ABT-1 induces enhanced release of inflammatory cytokine IL-8 from U937 cells accompanying ADCP assays at both 50 nM and 1 µM compound concentrations.
Figure 13:
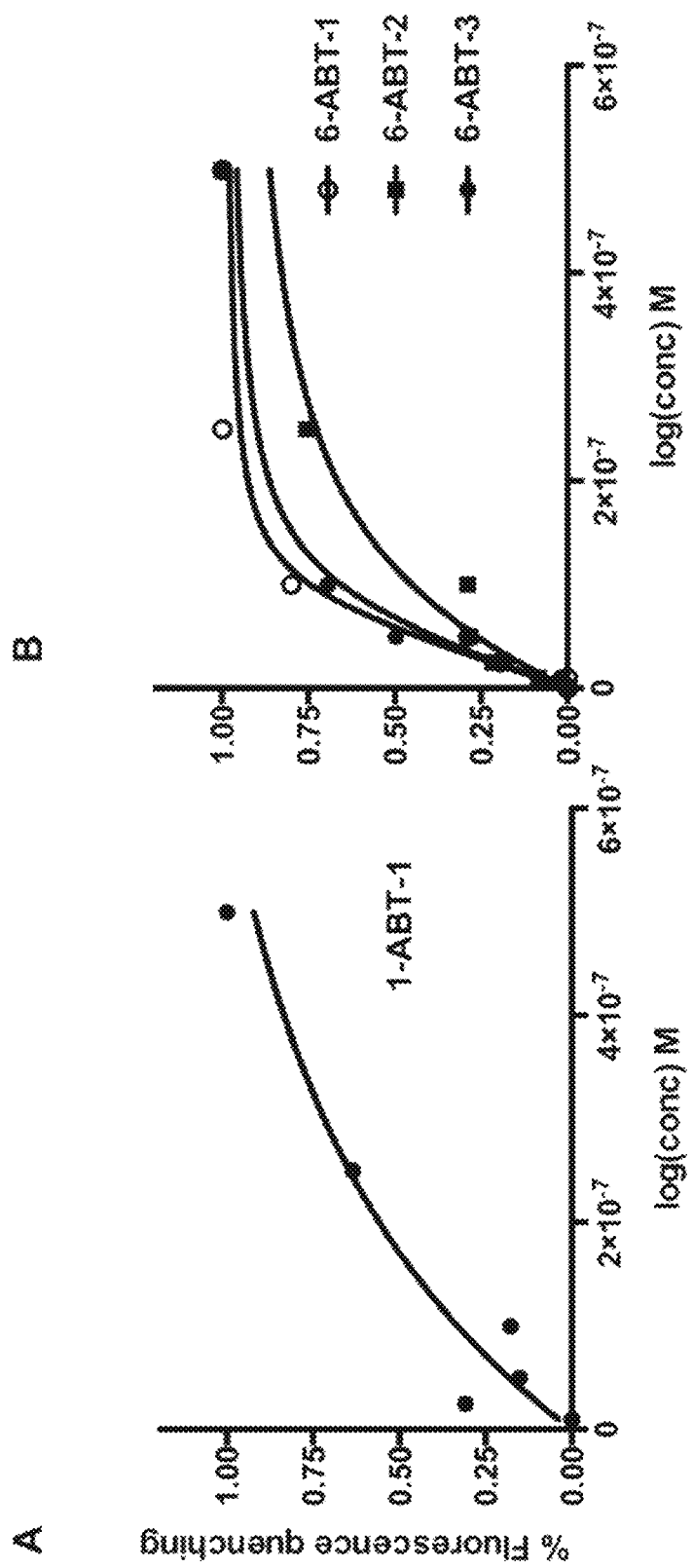
FIG. 13 shows (A-B) Fluorescence titration of 100 nM candidate ARM-U derivatives with increasing concentrations of uPAR accompanied by a saturatable quenching of ARM-U2 intrinsic fluorescence. (A). 1-ABT-1, 275 nM+/−43 nM (B). 6-ABT-1, $K_d$=8.7 nM+/−3.3 nM, 6-ABT-2, $K_d$=66 nM+/−9.5 nM, 6-ABT-3, 18 nM+/−5 nM. The generation of binding isotherms enabled for the calculation of solution equilibrium dissociation constants for the binding interaction between select ARM-U2 derivatives with uPAR. Extraction of $K_D$ for each derivative was carried out using the quadratic equation S1 described in the examples section confirming the significantly increased affinity of 6-ABT-1 for uPAR compared to 1-ABT-1. (C) Direct ELISA binding assay demonstrating the ability 2 to bind immobilized uPAR with much higher affinity than parent derivative 1 1-ABT-1. uPAR binding is also specific for the uPA binding site as demonstrated by the displacement of 6-ABT-1 from uPAR following the addition of exogenous 100 nM uPA-amino terminal fragment (ATF). (D) Competitive ELISA binding assay demonstrating the ability of the PEG-3 linker 9 substituted ARM-U2 derivatives to compete with immobilized uPA for uPAR. $IC_{50}$ abstracted from this data was used to calculate the inhibitory constant of each ARM-U2 derivative for uPAR employing equations 2 and 3. Highest affinity derivative was for 6-ABT-1.
Figure 13:
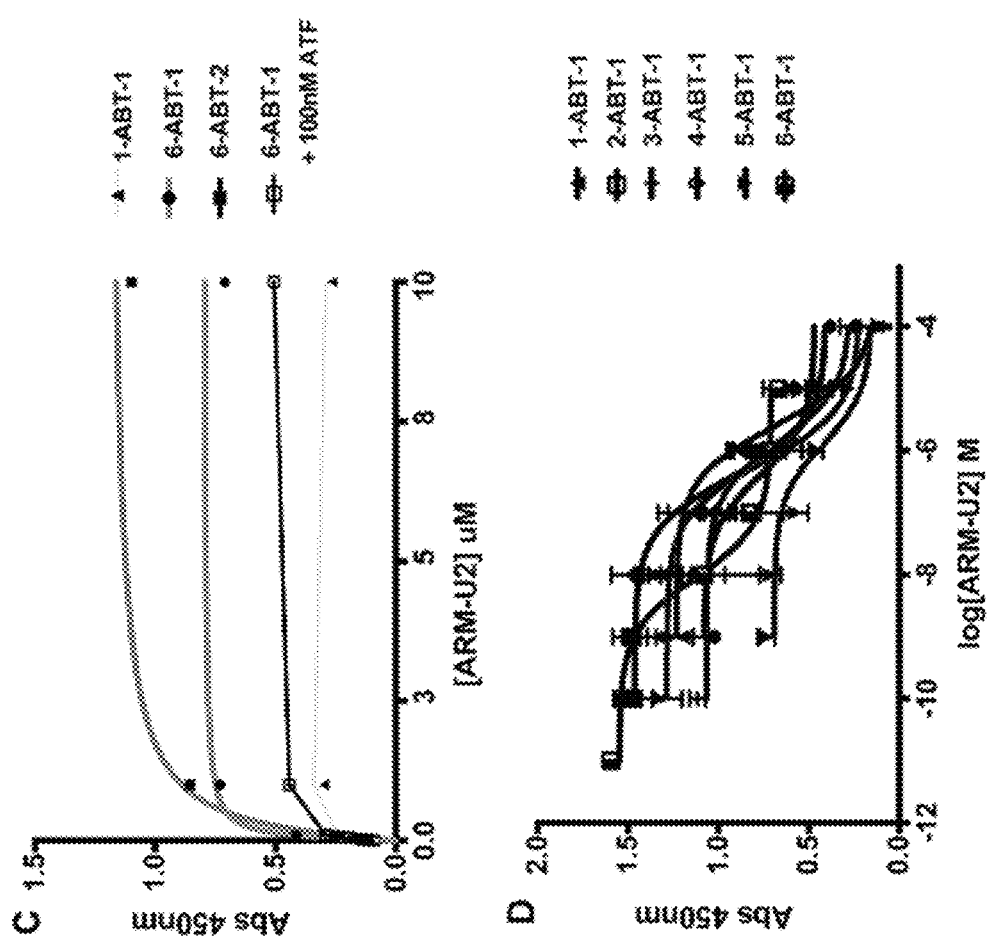
Figure 14:
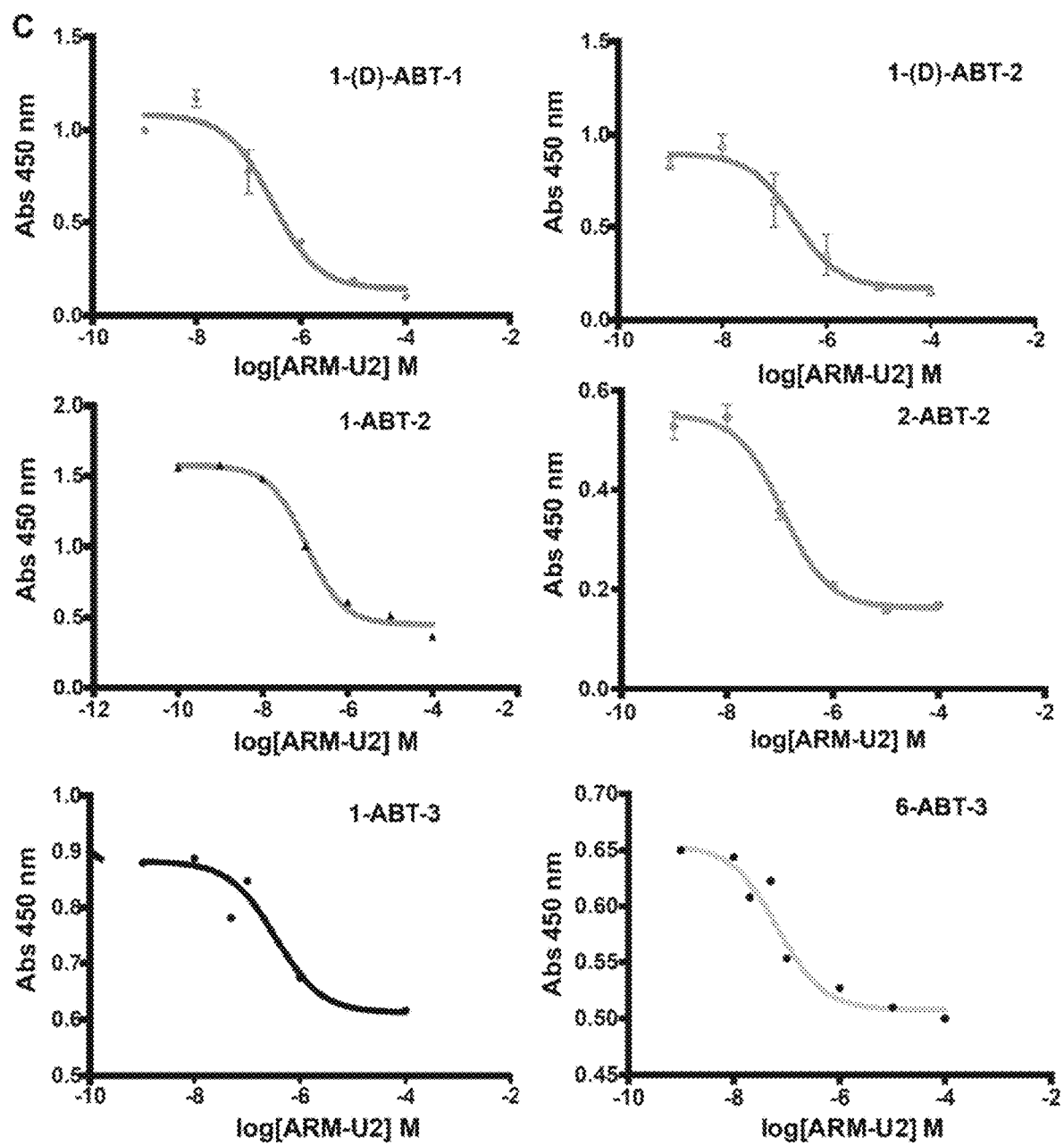
FIG. 14 shows A. direct ELISA binding assay demonstrating the ability of ARM-U2 6-ABT-1 and 6-ABT-2 to bind immobilized uPAR with much higher affinity than parent derivative 1-ABT-1. uPAR binding is also specific for the uPA binding site as demonstrated by the displacement of 6-ABT-1 from uPAR following the addition of exogenous 100 nM uPA-ATF. B. Competitive ELISA binding assay demonstrating the ability of the ABT-1 ARM-U2 derivatives to compete with immobilized uPA for uPAR. IC50 abstracted from this data was used to calculate the dissociation constant of each ARM-U2 derivative for uPAR employing equations 1 and 2. Highest affinity derivative 6-ABT-1 shown in red trace. C. Competitive ELISA binding isotherms for the longer linker (ABT-2/3) ARM-U2 derivatives in addition to the (D)-stereoisomer of derivative 1-ABT-1.

To further assay effector cell activation by ARM-U2, we investigated the release of pro-inflammatory cytokines by U937 monocytes in the context of ADCP assays. Thus, cellular supernatants were isolated from ADCP assay conditions and evaluated using a multi-inflammatory cytokine ELISA format. The results are shown in FIG. 11. Higher levels of IL-8 secretion were observed in assays containing 50 nM or 1 µM ARM-U2 compared to control samples lacking ARM-U2 (FIG. 11B).

The inventors also examined the efficacy of ARM-U2 in a B16–uPAR mouse allograft model developed in our laboratory. Mice immunized to produce anti-DNP IgG antibodies containing tumors expressing human uPAR, received daily treatment via intraperitoneal (IP) injection and were monitored over the course of 42 days. Mice treated with ARM-U2 (20 mpk or 100 mpk) showed a significant decrease in the rate of tumor growth relative to those injected with PBS only, corresponding to a calculated tumor growth inhibition (TGI) of approximately 90% (See FIG. 12A). This TGI level was comparable to mice treated with doxorubicin (Dox, 1 mpk), an anti-mitotic chemotherapeutic agent often used as standard-of-care in treating metastatic malignancies. For animals treated with either doxorubicin or ARM-U2, tumor regression persisted almost 14 days following treatment cessation at which point animals with excessive tumor burden were sacked. Interestingly, mice treated with the 100 mpk dose of ARM-U2 showed a moderate decrease in efficacy especially within the first 22 days of treatment compared to the mice dosed with 20 mpk of ARM-U2 (FIG. 12A). This reduction in efficacy observed in vivo in the 100 mpk dosing regimen is consistent with a "prozone" mechanism of action as observed in cellular ADCP and ADCC assays, although other mechanisms might also be involved. Mean survivals of 27 and 30 days were observed for mice treated with doxorubicin and ARM-U2 respectively relative to a mean survival of 17.5 days for the PBS control (FIG. 12B). Tumor regression was even more pronounced in the combination treated arm of the study with a mean survival of 37 days. Remarkably, mice treated with ARM-U2 at both 20 mpk and even 100 mpk did not lose weight in contrast to that observed accompanying treatment with doxorubicin. Although lack of weight loss is not a definitive indicator of compound safety, these results represent a positive indication that ARM-U2 might possess an improved side-effect profile compared to doxorubicin (FIG. 12C).

Further Studies

ARM-U2 Fluorescence and ELISA Binding Studies

Selected ARM-U2 derivatives were assayed for their ability to bind recombinant uPAR using a fluorescence quenching assay. The compounds stored at −20° C. as DMSO stocks were diluted into PBS aliquots at a fixed 50 nM concentration. Increasing concentrations of recombinant uPAR were mixed with each compound containing aliquot and the fluorescence of the solution measured following 1 h equilibration times. Increasing concentrations of uPAR resulted in saturable quenching of intrinsic ARM-U2 fluorescence generating a binding isotherm that could be fit by Equation S1 to extract the equilibrium dissociation constant for ARM-U2 binding to uPAR. To confirm that the observation of uPAR dependent fluorescence quenching was indeed due to specific binding to uPAR and to validate ARM-U2 binding to uPAR specifically via the uPA binding site, a direct binding ELISA assay was developed. In this assay, clear 96-well high-binding plates from CoStar, were loaded with 100 µl/well of 50 nM recombinant uPAR 807-UK-100-CF from R&D systems prepared from a 100 µg/ml (approx. 2.1 µM) stock of uPAR in PBS and left overnight at room temperature to equilibrate. Following equilibration, the plate was washed with wash buffer 1× (400 µl/well of 0.05% Tween/PBS), blotted dry and blocked for 1 hr with 300 ul/well of 2% BSA/PBS. Following blocking, the plate was washed with 400 ul of the wash buffer and blotted dry. Dilutions of each ARM-U2 derivative from 100× stocks in DMSO were made into 100 µl/well of 1% BSA/PBS and left to equilibrate with immobilized uPAR for 2 h at RT. Following the binding step, the plate was washed 1×200 µl and 1×400 µl of wash buffer and blotted dry. A solution of anti-DNP rabbit IgG KLH biotinylated antibody was prepared in 1% BSA/PBS from a 10,000× commercially available stock of 2 mg/ml in 500 µl (Life Technologies) and added in a volume of 100 µl/well, left to equilibrate for 1 h at RT. To assess selectivity of binding of ARM-U2 to the uPA binding site of uPAR, 100 nM competitor uPA-ATF (Innovative Research), the amino terminal fragment of uPA which retains the complete binding capability of urokinase for uPAR, was added during the biotinylated anti-DNP antibody incubation step. Following incubation with the antibody, the plate was washed 1×200 µl 1×400 µl of wash buffer and blotted dry. A solution of avidin-HRP was prepared by diluting 20 µl of stock solution (e-bioscience) into 10 ml of 1% BSA/PBS solution and 100 µl added to each well and incubated for 20 min at RT. Following 3×400 ul washes and blotting, 100 ul of HRP substrate solution (TMB-substrate, Thermo) was added and the wells allowed to develop until a clear difference between negative control (no uPAR loaded) and wells containing ARM-U2 could be observed by differences in the emergence of blue color at which time the development was halted by the addition of 50 µl 4N sulfuric acid. The absorbance at 450 nm was measured using an in-house Perkin-Elmer fluorescence plate reader.

All ARM-U2 derivatives were assessed for their ability to bind selectively to recombinant uPAR in vitro using a competitive ELISA binding assay. DMSO stock solutions of each ARM-U2 derivative stored at −20° C. were titrated into wells pre-coated with human urokinase (isolated from human urine, ProSpec 1 mg/ml deI water 18.5 µM) in the presence of uPAR. Selective binding to uPAR by ARM-U2 at the uPA binding site competes with uPAR-uPA binding which is required for a positive UV 450 nm absorbance signal. Increasing concentrations of ARM-U2 displace increasing amounts of uPAR from uPA which is detected by anti-uPAR/biotin labeled antibodies followed by avidin-HRP. The sigmoidal binding isotherm of absorbance at 450 nm vs log ARM-U2 concentration can then by fit by non-linear regression analysis to obtain the $IC_{50}$ for ARM-U2/uPAR binding (Equation S2) which can then be translated into a $K_I$ for ARM-U2/uPAR binding using a competitive binding model adapted from the Cheng-Prusoff equation relating $K_I$ to $IC_{50}$ (Equation S3). The ELISA experiments were performed as followed: To Corning high binding 96 well flat bottom plates was added 100 µl/well of 100 nM urokinase in sterile PBS. The plates were sealed and left to incubate at 4° C. overnight. The plates were then washed 1× with 200 µl wash buffer (PBS+0.05% Tween-20) and 1× with 400 µl wash buffer. The plates were blotted on paper towel and blocked for 1 h shaking at room temp with 300 µl of a solution of thermo superblock in PBS per well. Molecule dilutions into solutions of a fixed concentration (10 nM) of uPAR were prepared in 0.025% triton-X/PBS on a separate low binding plate during the blocking hour. The plates were again washed followed by the addition of 100 µl of the ARM-U2/uPAR solution with 0.1% final DMSO concentration. The solutions were mixed by multichannel pipette, sealed, and incubated for 2 h with shaking at room temperature. The plates were then washed 1× with 200 µl wash buffer (PBS+0.05% Tween-20) and 2× with 400 µl wash buffer. The plates were blotted on a paper towel followed by the addition of 100 µl/well of a solution of biotinylated anti-uPAR antibody in 1% BSA/PBS. (R&D Systems, 3.3 µl taken from 50 µg/250 µl-1000× stock) and incubation with shaking for 1 h at room temp. The plates were washed 1× with 200 µl wash buffer and 2× with 400 µl wash buffer and blotted on a paper towel. 100 µl of avidin-HRP (stock ~500× from e-bioscience) were added per well, incubated 20 min with shaking at room temp followed by washing 1× with 200 µl wash buffer and 3× with 400 µl wash buffer. The plates were blotted dry with paper towel and 100 µl of TMB substrate was added to each well. The emergence of blue color was monitored and the reaction quenched with the addition of 50 µl of 2M sulfuric acid to each well followed by measuring the absorbance at 450 nm using a fluorescence plate reader.

$$Y=((((P1+x+K1)-((-P1-x-K1)^2-(4*x*P1))^0.5)/2*(P3-P4)/P1)+P4) \quad \text{Equation S1:}$$

Y=% fluorescence quench proportional to [ARMU2–uPAR] complex
x=[uPAR] added
P1=total conc. of ARM-U2
P3=maximum fluorescence quenching signal
P4=minimum fluorescence quenching signal
K1=dissociation constant for ARMU2/uPAR binding $$Y=A_{min}+(A_{Max}-A_{Min})/(1+10^{\wedge}((X-\text{Log } IC_{50}))) \text{ where } X=\text{conc of ARM-U2 }[M], Y=\text{fraction of } uPAR \text{ bound to } ARM\text{-}U2 \quad \text{Equation S2:}$$

$$K_I=K_D1*[\text{complex1}]/2*(1/(-[uPA_T]+[\text{complex1}]/2)-IC_{50}/([uPA_T]*([\text{complex1}]/2-[uPAR_T])+[\text{complex1}]/2*(K_D1-[\text{complex1}]/2+[uPAR_T]))) \quad \text{Equation S3:}$$

Figure 15:
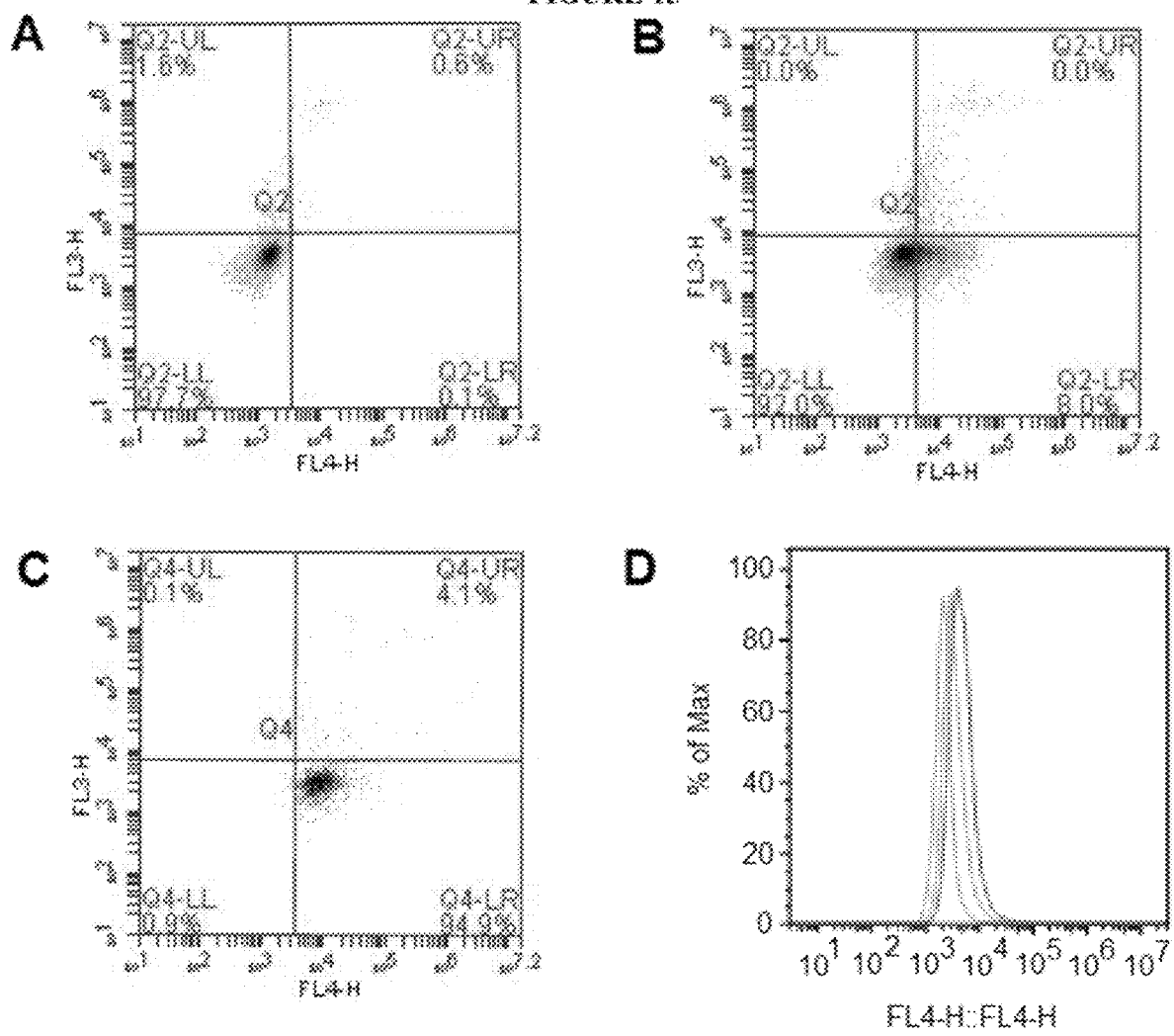
FIG. 15 shows flow cytometric-antibody recruiting analysis of the ability of ARM-U2 derivatives to bind simultaneously to both cell surface uPAR and exogenously added anti-DNP antibodies. Top left panel shows the background antibody recruiting taking place in the presence of A172 cells and anti-DNP antibody without the addition of ARM-U2. Middle panel shows the antibody recruiting capability of 10 uM ARM-U2 1-ABT-1 represented as a dot plot with the lower left gate representing background antibody recruiting in the absence of compound and the lower right gate representing compound dependant antibody recruiting. Right panel shows the antibody recruiting capability of 10 uM ARM-U2 6-ABT-1 represented again as a dot plot with the gates assigned as described for 1-ABT-1. Note the significantly higher percentage of antibody binding to the cell surface of 6-ABT-1 vs 1-ABT-1 (left panel) depicted as a shift in FL-4 fluorescence with almost all the cells present in the lower right gate. Below. histogram compares the antibody recruiting capability of derivatives 1-ABT-1 with its longer linker counterparts 1-ABT-2 and 1-ABT-3 all at 10 uM concentrations highlighting lower shift in FL-4 fluorescence corresponding to the decreased potency of antibody recruitment accompanying increasing linker length.
Figure 16:
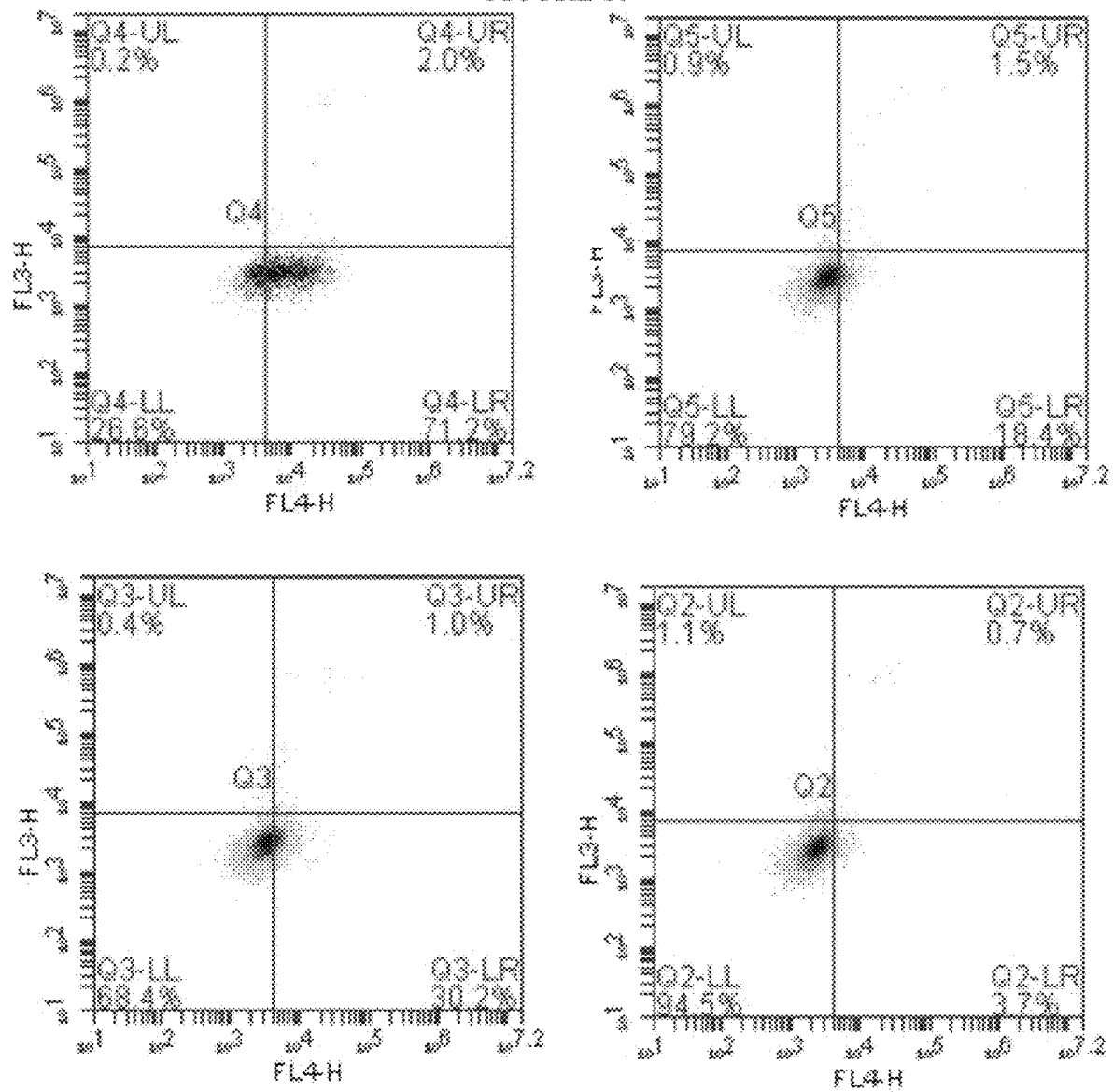
FIG. 16 shows the uPAR-dependant simultaneous binding of 6-ABT-1 to both the surface of uPAR+ glioblastoma A172 cells and anti-DNP antibodies evaluated using a flow cytometry-based antibody-recruiting in vitro assay. Binding was detected by the addition of anti-DNP antibody plus streptavidin-AlexaFluor647 following the addition of 10 uM or 1 uM 6-ABT-1 (upper left and lower left panels respectively), and could be outcompeted upon the addition of 2.1 uM soluble recombinant human uPAR displacing 6-ABT-1 off the cell surface (upper right panel-10 uM 6-ABT-1 displaced, lower right panel-1 uM 6-ABT-1 displaced).
Figure 17:
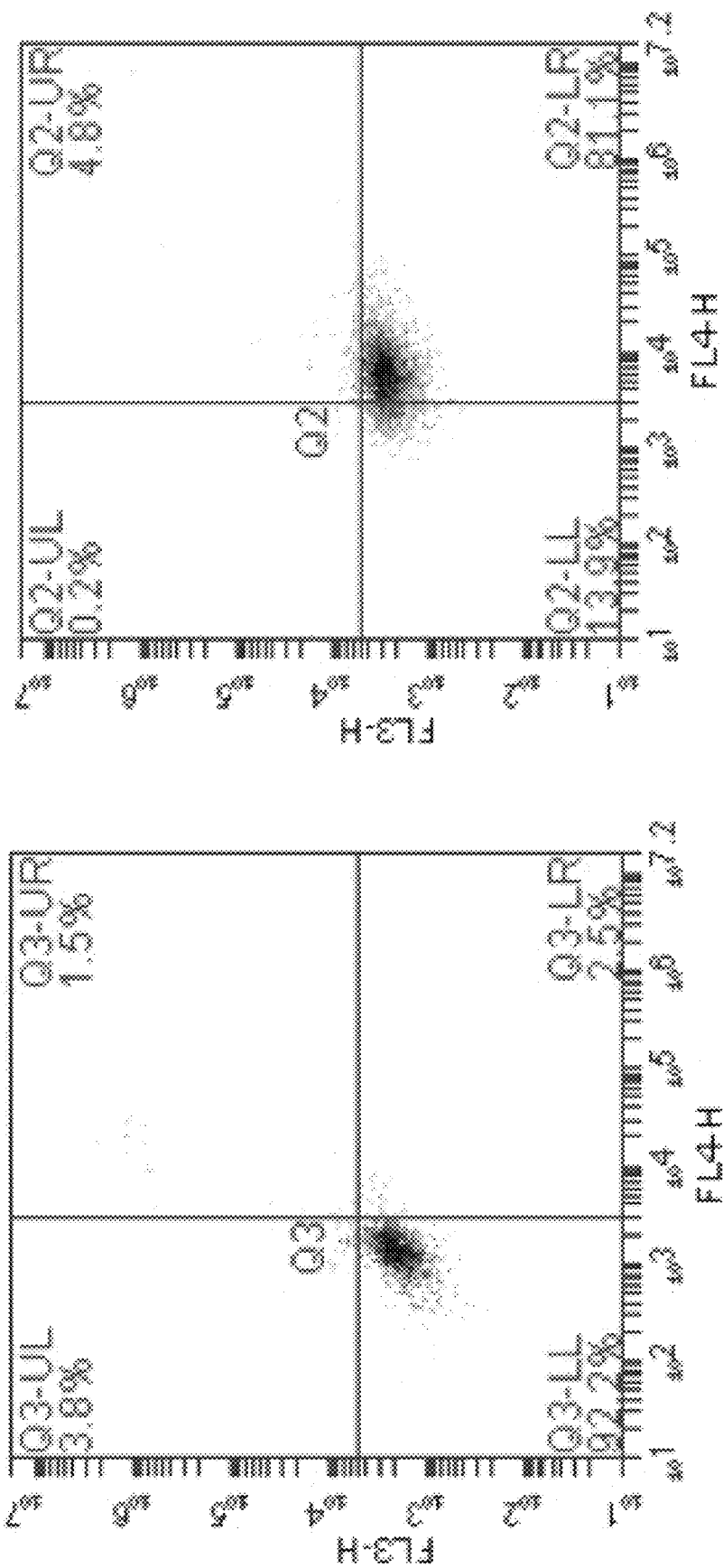
FIG. 17 shows that compound 6-ABT-1 selectively binds to uPAR and stimulates immune responses against uPAR+ cancer targets. Left. 10M of 6-ABT-1 minimally bound to uPAR− negative B16 vector-transfected melanoma cells. Right. 10 µM of 6-ABT-1 bound strongly to B16 melanoma cells transfected with human uPAR Compound binding was detected by biotinylated anti-DNP antibody plus streptavidin-AlexaFluor647.
Figure 18:
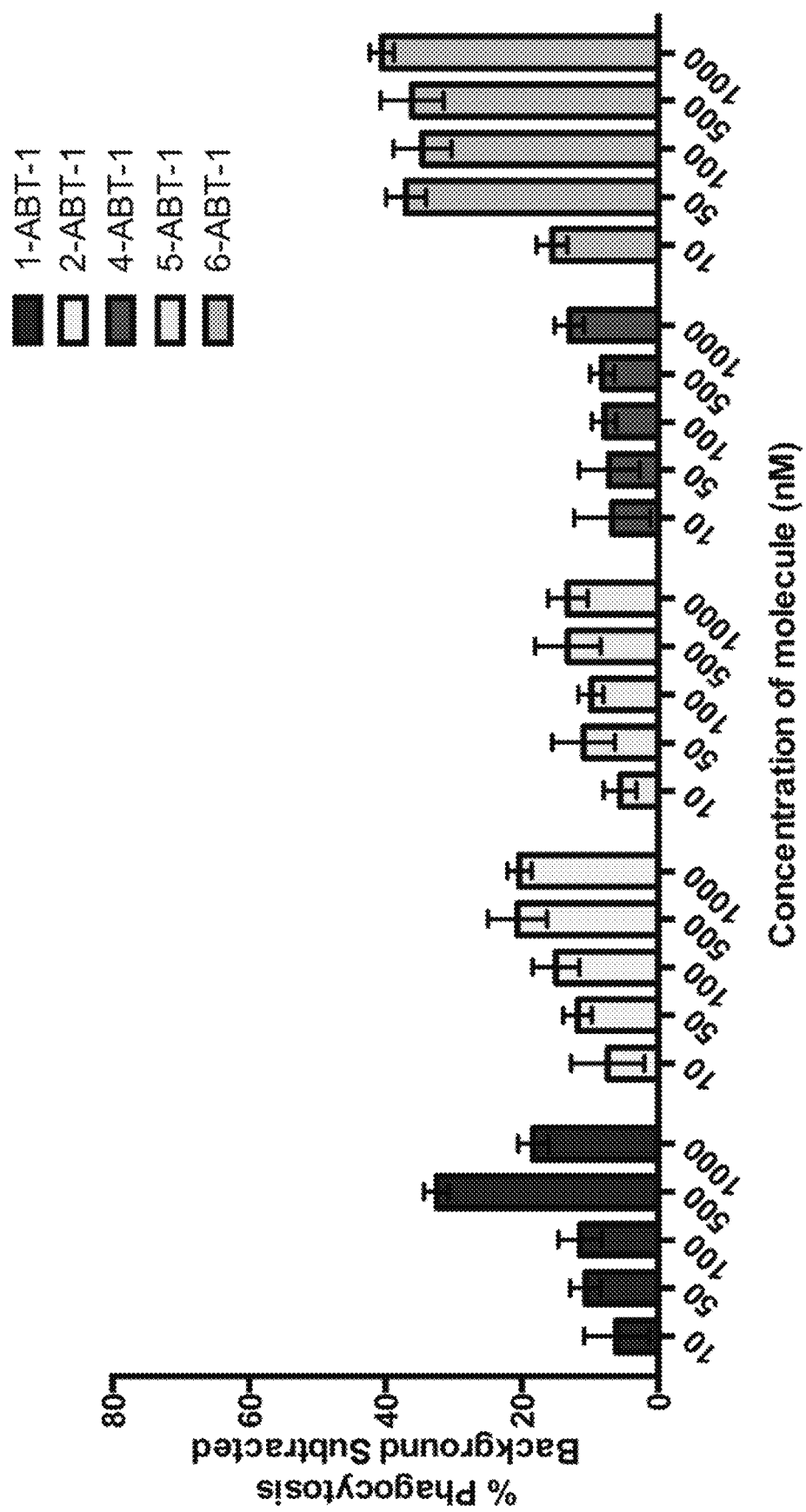
FIG. 18 shows phagocytosis of A172 target cells by U937 monocytic cells induced by shortest linker ABT-1 series ARM-U2 derivatives in the presence of anti-DNP antibodies illustrating the increased efficacy and potency of double sulfonate derivative 6-ABT-1.
Figure 20:
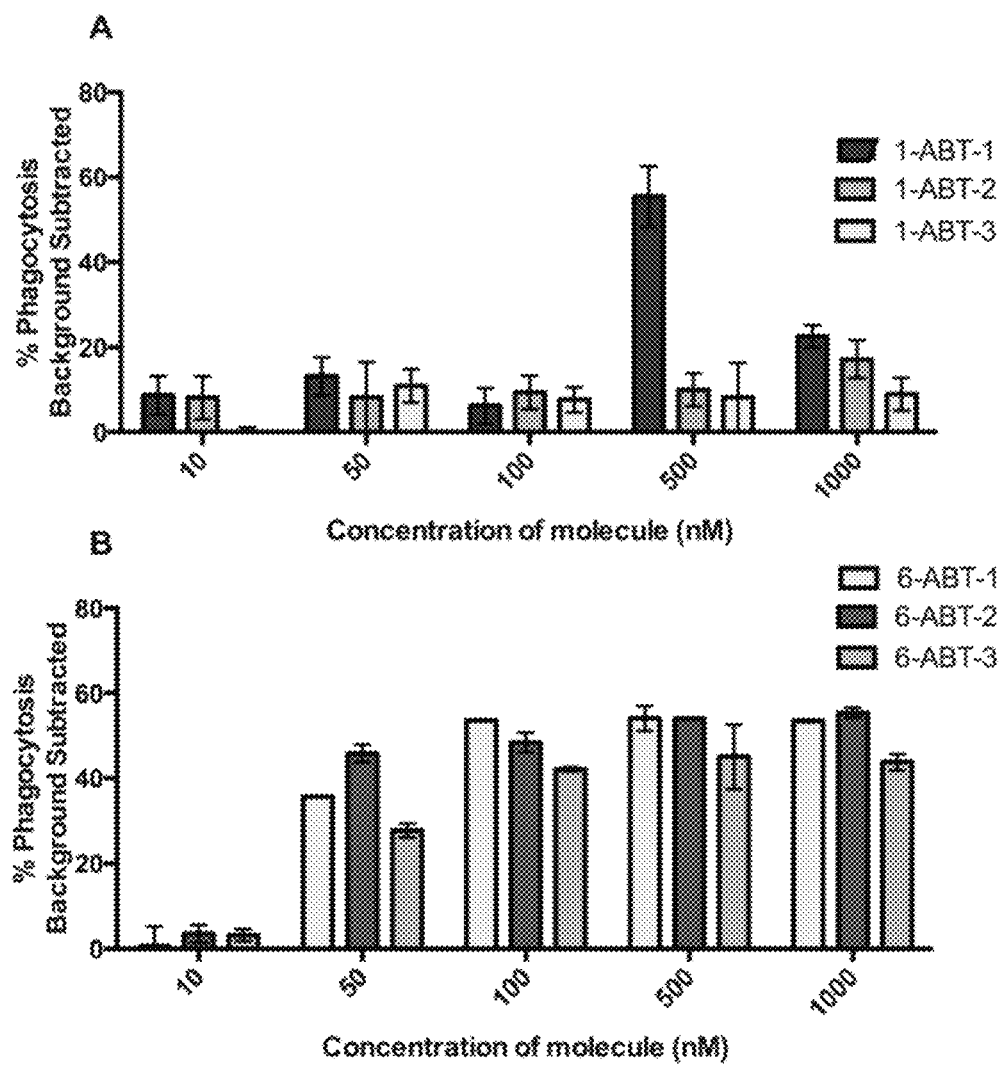
FIG. 20 shows A. Phagocytosis of A172 target cells by U937 monocytic cells induced by parent mono acid derivatives 1-ABT-1/2/3 illustrating the decreased potency associated with increasing antibody binding terminus liker length. B. Identical assay as in A. above only with disulfonate derivatives 6-ABT-1/2/3 illustrating a significant increase in efficacy and potency relative to parent derivatives 1-ABT-1/2/3 in panel A in addition to a modest decrease in potency with increasing linker length beyond a PEG-8 spacer.
Figure 21:
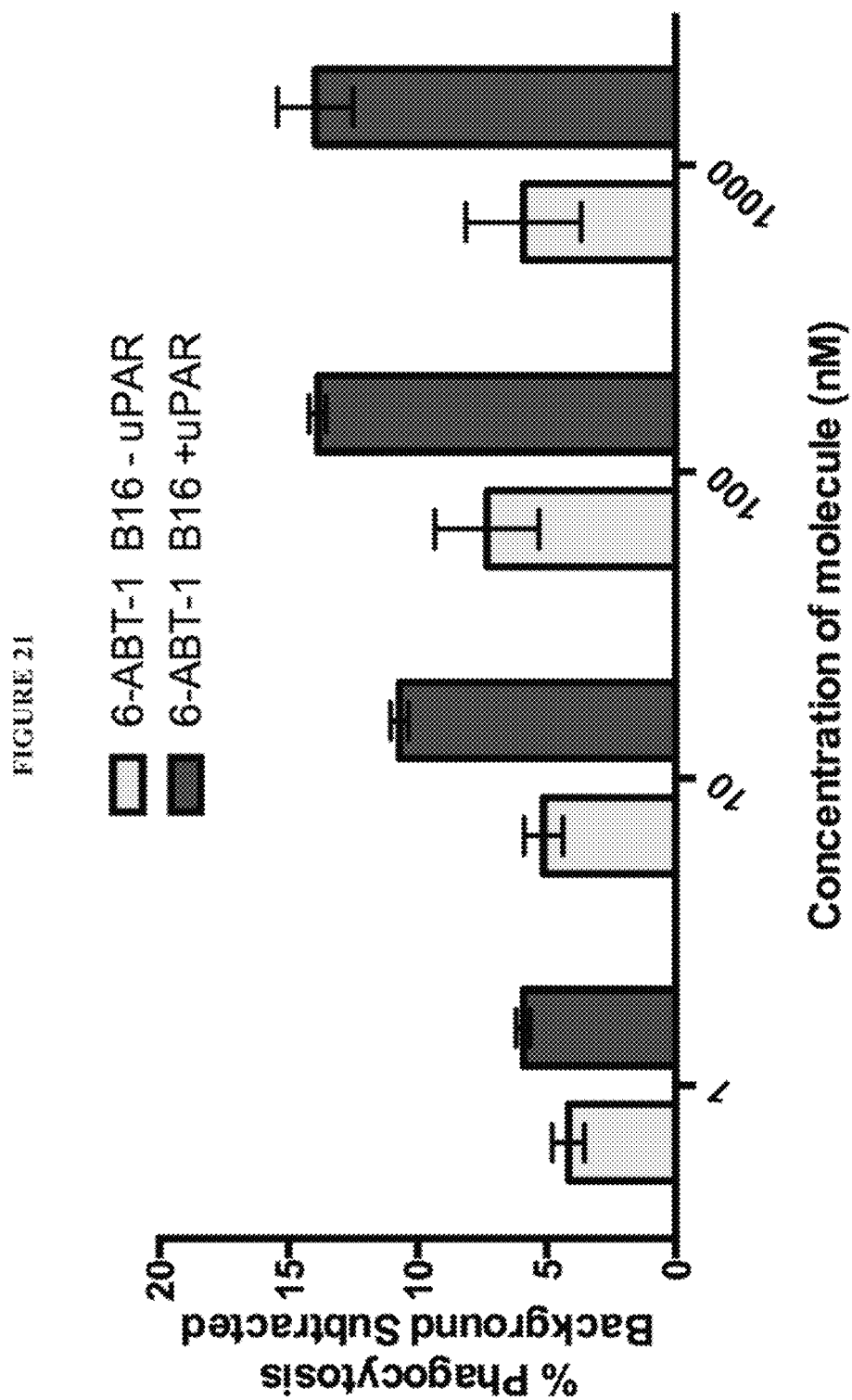
FIG. 21 shows Flow cytometry ADCP assay analysis of B16 target cells transfected with a human uPAR cloned plasmid vs transfected with an empty vector, by U937 monocytic cells induced by derivative 6-ABT-1, demonstrating the specificity of 6-ABT-1 for cell surface uPAR.

$K_D1=K_D$ (uPA–uPAR)=0.2 nM
$K_1=K_1$ (ARMU2–uPAR)
[complex1]=conc of uPAR–uPA complex
$[uPA_T]$=total conc of uPA=100 nM
$[uPAR_T]$=total conc of uPAR=10 nM
$IC_{50}$ for ARMU2 binding uPAR Antibody Recruiting Assays A172 glioblastoma cells (ATCC, CRL-1620) were suspended in Assay Media (phenol-free RPMI 1640 medium plus 10% ultra-low IgG FBS). $10^5$ cells taken up in 50 µl media or media containing exogenous uPAR were mixed with a fixed concentration of the indicated ARM-U2 compound from 100×DMSO stocks. After a 1 hour incubation on ice, cells were washed with 1.5 mL of cold Assay Media, pelleted for 2 min at 200 rcf, aspirated, and resuspended in 100 L of fresh assay media with 133 nM of anti-DNP-biotin-xx conjugate antibody☐ (Invitrogen). Cells were allowed to incubate for an additional 30 min on ice, L of a 2 mg/mL stock of streptavidin-AlexaFluor647 conjugate☐ and then 1 (Invitrogen) was added. Negative control tubes contained streptavidin+/−antibody in the absence of ARM-U2. After 15 min more on ice, cells were washed 2× with 1.5 mL of cold Assay Media before flow cytometric analysis. Propidium iodide was added from a 1000× stock as a cell viability stain (FL-3 positive) and antibody recruiting to the cell surface was evaluated by measuring increasing cell counts in the FL-4 channel negative for FL-3 (lower right quadrant of representative dot plots). The evaluation of selective binding of ARM-U2 to uPAR was carried out by performing the antibody recruiting assay described above identically, save that B16-F10 melanoma cells, either stably transfected with human uPAR or the empty vector pcDNA3.1 (isogenic negative control), were used in place of A172 cells. The results of these assays is presented in FIGS. 15-17.

Antibody-Dependent Cellular Phagocytosis (ADCP) Assays

IFNγ-primed U937 cells were stained with DiD dye (final concentration 1.9 µM) for 30 min at 37° C. A172 target cells were prepared by staining adherent cells with DiO dye (Invitrogen; final concentration 1.9 µM), and then nonenzymatically detaching the cells with 0.5 mM EDTA and EGTA. Cells were counted with trypan blue staining to verify cell viability. To measure phagocytosis, $2.5 \times 10^4$ target cells were suspended in 25 ul phenol-free low-IgG RPMI media to which 25 ul of 100 nM anti-DNP antibody (rabbit polyclonal KLH IgG, Invitrogen-100× stock) containing media was added followed by the addition of 1 ul of ARM-U2 from 100×DMSO stocks or 6-ABT-4 from 100×DMSO stocks for compound out-competition experiments, followed by the addition of 50 ul of $10^5$ U937 cells in the same RPMI Assay Media resulting in a final volume of 100 uL. This experimental setup yielded an effector-to-target ratio (E:T ratios) of 4:1. For out-competition studies with exogenous uPAR, 250 ul of A-172 target cells in assay media was added directly to lyophilized 100 ug uPAR (R@D systems) to yield an 8.4 uM stock uPAR concentration, this was then combined in the manner and order described above. Eppendorfs were centrifuged at 200 rcf for 2 min then incubated at 37° C. for 1 hour or at 4° C. for 1 hr in controls establishing real phagocytosis is indeed represented by double positives in flow cytometry. Phagocytosis was halted by placing tubes on ice. Flow cytometric measurements were then made using an Accuri C6 flow cytometer with forward scatter and side scatter gating parameters initially set collecting on live intact cells. The live cell population selected was further gated into four quadrants using dual FL-1 and FL-4 fluorescence enabling for the differentiation of effector only cells (top left quadrant-high FL-4), target only cells (bottom right quadrant-high FL-1 fluorescence), and double positive overlapping target and effector cells (top right quadrant-high FL-1 and FL-4 fluorescence). The upper right quadrant indicating the number of phagocytosed target cells was used to calculate the percent phagocytosis: % targets phagocytosed=

[(double-positive cells)/(remaining target cells+double-positive cells)×100%]–background phagocytosis. Results are shown in FIGS. 18-21.

Inflammatory Cytokine Release ELISA

Figure 22:
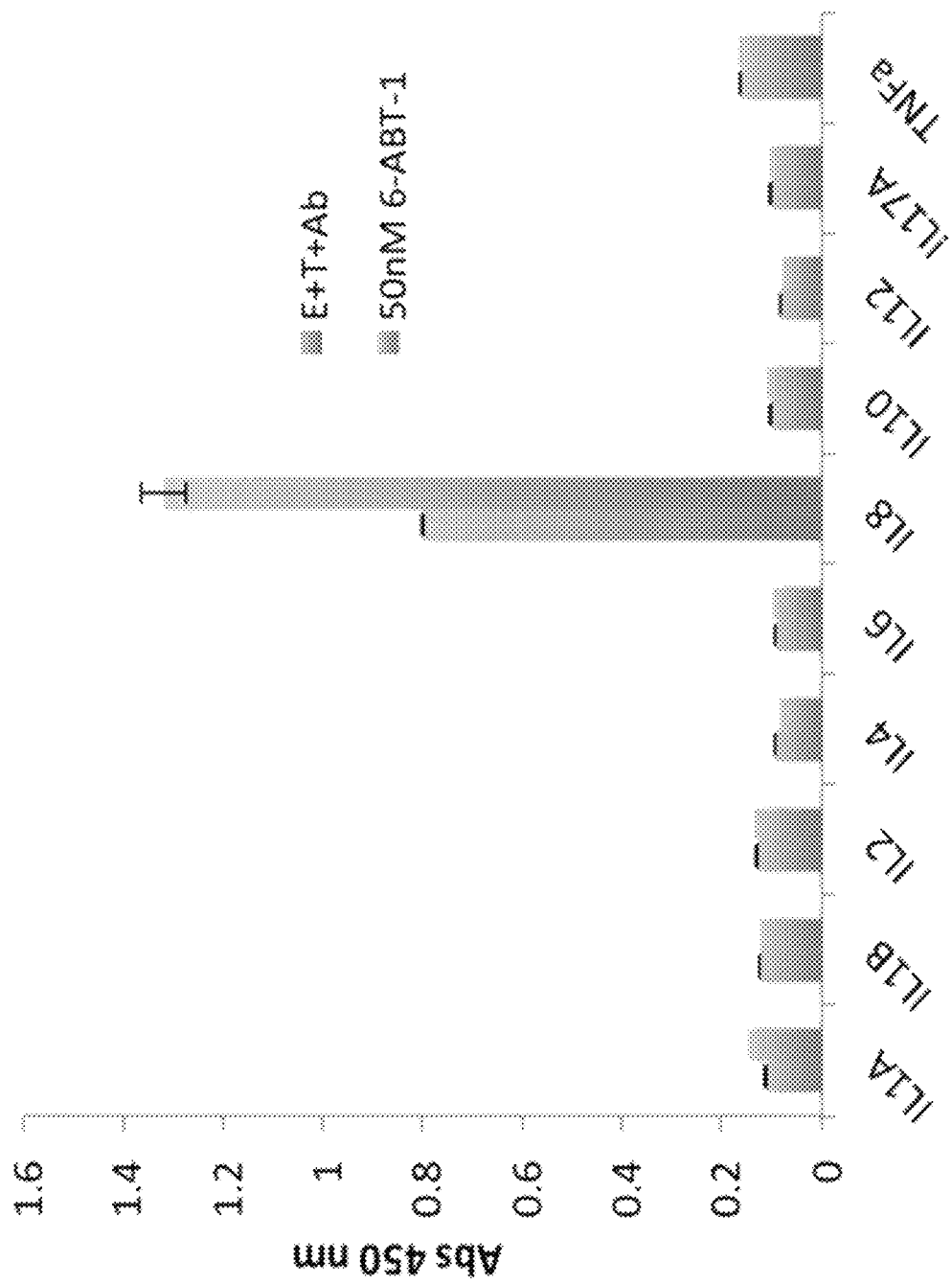
FIG. 22 shows histogram representation of a multi-inflammatory ELISA experiment used to assay the ability of ARM-U2 6-ABT-1 to induce u937 effector cytokine release in the presence of A172 target cells. Indicated is a significant enhancement in the release of IL-8 by u937 cells induced by 6-ABT in the presence of target cells plus anti-DNP antibodies

Analysis of u937 secretion of 12 human inflammatory cytokines in the presence of anti-DNP antibodies and A172 target cells induced by ARM-U2 6-ABT-1 was carried out using the Multi-Analyte ELISArray Kit (MEH-004A, Qiagen). Sample preparation involved the immobilization of A172 target cells (approx. 1,000,000/3 ml T-flask) over the course of 24 hours at 37° C. followed by the addition of 1.5 ml phenol free RPMI assay media. 30 ul of 6-ABT-1 from 100×DMSO stocks or DMSO only was added (50 nM final 6-ABT-1 conc, 1% DMSO) followed by the addition of 30 ul anti-DNP antibody from 100× aqueous stocks (133 nM final concentration). 1.5 ml of IFN-gamma primed U937 cells suspended in phenol free RPMI assay media at a concentration of 2666.6 cells/ul, was then added and the plate incubated at 37° C. for 24 hr. Following incubation, the supernatant was collected, pelleted by centrifugation, and the supernatant collected and stored on ice. The ELISA plate pre-loaded with immobilized antibodies specific for each of the 12 cytokines tested was loaded with the cell supernatant collected, washed, and the bound cytokine detected all as described in the associated instruction manual available from Qiagen. The ELISA plate was read at an absorbance of 450 nm using a Perkin-Elmer Fluorescence plate reader with increases in absorbance at 450 nm proportional to bound cytokine. Results are show in FIG. 22.

Amnis Imagestream Imaging

Phagocytosis experiments were conducted as described above for ADCP assays only cellular samples were fixed following 1 h incubation at 37° C. using 3% formaldehyde for 30 min on ice. Cells were washed once in PBS, then stained with anti-CD14-APC and anti-CD11b-APC antibodies (Biolegend) plus Hoechst dye (Invitrogen) for 30 minutes on ice. U937 monocytes were also stained with DID while A172 target cells were stained with DIO membrane dyes. The cells were washed once in PBS, then analyzed on an Amnis Imagestream X flow cytometer, where images and data for 30,000 events/sample were collected. Data was analyzed using Amnis IDEAS software.

ADCC Using the xCELLigence System

One day before the experiment, A172 cells were detached, counted, aspirated, and diluted in FBS ADCC media (to a final concentration of 25,000 cells/mL). Into each well of an E-plate was added 200 μL of the cell suspension (5,000 cells). The plate was allowed to stand at ambient temperature (30 min) and maintained in an incubator (37° C., 12 h). The xCelligence system was maintained inside the incubator (37° C.). An E-plate containing 100 μL FBS ADCC media per well was used for obtaining background measurements. The seeded E-plate was placed in the port, and cell index readings were obtained (every 2 min for 30 min) to confirm that the cells had adhered properly. The wells were aspirated and to each well was added 50 μl of FBS-free RPMI media followed by the addition of 0.15 μl of a 1000× stock of 2 in DMSO followed by the addition of 1.5 ul of Rabbit IgG anti-DNP from a 2 mg/mL stock to give final concentrations of 133 nM antibody and 10 nM, 50 nM, or 1 μM 2. The E-plate was returned to the port, and cell index readings were obtained (every 2 min for 90 min). A solution of u937 cells in FBS-free RPMI media as described above for ADCP assays, was prepared and 100 μl added to each well of the E-plate. The E-plate was returned to the port, and cell index readings were obtained (every 2 min for 24 h, 37° C.). Cell index readings were normalized (RTCA software) at the time point immediately after addition of the u937 cells. Figure S13 shows the representative plots of changes in cell index with time in the presence and absence of ARM-U2, antibody, and competitor compound 20. Values from the 24-hour time point were used to calculate specific killing. Normal growth was defined as that shown by target A172 cells treated with effector cells and anti-DNP antibody, but no compound. Specific killing was calculated as the following formula:

% specific killing=[1−(normalized cell index observed)/(normal growth)]*100

Isoxazole Cleavage to Corresponding Compounds

Synthetic Procedure:

Upon exposure of a red solution of 10 mg of an ARM-U2 compound (6-ABT-1) in 1 ml DMSO to room light for up to 48 h or longer, a color change to purple was observed. The conversion/degradation occurs much more quickly in aqueous solution ($t_{1/2} \approx 3$ h) relative to DMSO ($t_{1/2} \approx 24$ h). The HPLC purification of this mixture resulted in isolation of 23 as purple solid obtained in 50% yield (5 mg). $^1$H NMR (500 MHz, DMSO-d$_6$) 12.05 (s, 1H), 8.95 (t, J=5.4 Hz, 1H), 8.81 (d, J=2.7 Hz, 1H), 8.25-8.21 (m, 5H), 8.08 (s, 1H), 7.88 (brs, 1H) 7.87-7.78 (m, 2H), 7.50 (dd, J=8.2, 2 Hz 1H), 7.28 (d, J=8.3 Hz, 1H), 7.20 (d, J=9.7 Hz, 1H), 7.09 (s, 1H), 3.55-3.47 (m, 12H), 3.40 (t, J=6.3 Hz, 2H), 3.22-3.08 (m, 2H), 2.96-2.71 (brm, 4H), 2.60 (m, 1H), 1.67-1.62 (m, 4H), 1.28-1.22 (n, 4H). HRMS (ES+) calc'd for $C_{42}H_{48}N_7O_{16}S_2$ (M+H proposed structure MW) Exact Mass: 970.2521 m/z. Found 970.2534 Additional carbon and two dimensional NMR characterization techniques will further confirm proposed structure of 23.

Compound 23

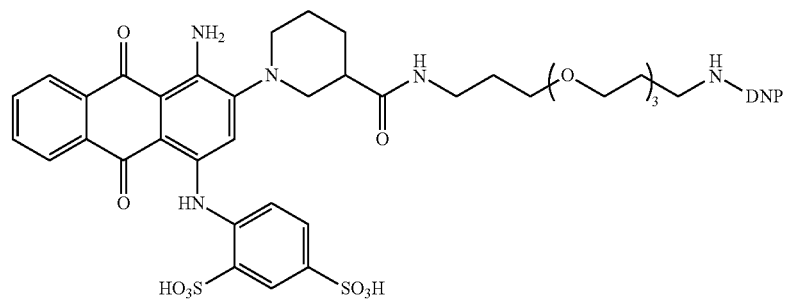

Biological Activity of Compound 23
Confirmation of Activity Against uPAR

Figure 23:
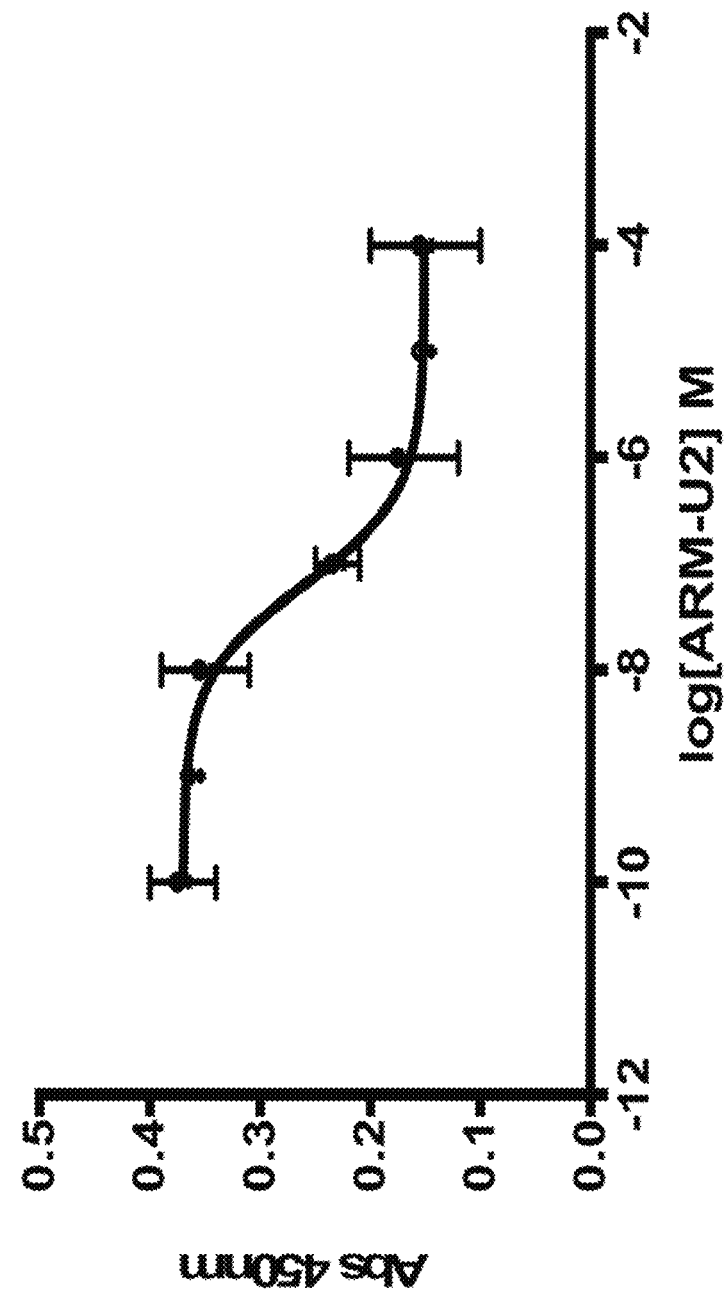
FIG. 23 shows the evaluation of binding affinity of ARM-U2 degradation product to 23 using a competitive ELISA. An $IC_{50}$ of 63 nM was observed translating to calculated $K_I$ of 10 nM demonstrating no change in uPAR binding affinity relative to ARM-U2.

Evaluation of binding affinity of ARM-U2 degradation product to 23 using a competitive ELISA. An $IC_{50}$ of 63 nM was observed translating to calculated $K_I$ of 10 nM demonstrating no change in uPAR binding affinity relative to ARM-U2. The results of this assay are presented in FIG. 23. The observation is consistent with literature reports of SAR studies on IPR-803 analogs and our computational and crystallographic data on ARM-U2 binding to uPAR.

Significance of the Present Invention

The selectivity and high affinity of ARM-U2 for uPAR which is over-expressed on many cancer cell types enables for its potential application as a therapeutic targeting a wide range of cancer cell types. ARM-U2 employs a dual mode of action as an anticancer therapeutic by disrupting the native uPA uPAR interaction as an antagonist and by targeting metastatic cancer cells for destruction by the host immune system as an antibody recruiting molecule and shows that employing small molecules to redirect the cytotoxic functions of antibodies selectively against cancer cells, might reduce the toxicity associated with other cancer fighting strategies.

The invention claimed is:

1. A compound according to the chemical structure:

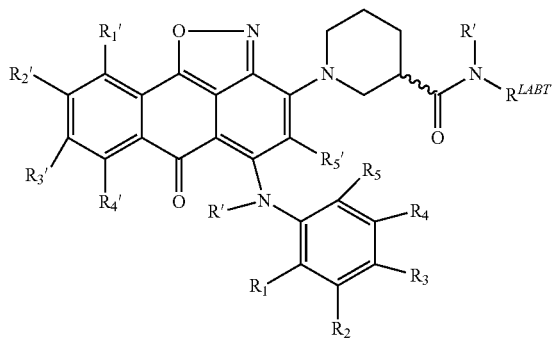

Wherein $R_1$, $R_2$, $R_3$, $R_4$ and $R_5$ are each independently H, a halogen, a $C_1$-$C_3$ alkyl group optionally substituted with one or two hydroxyl groups or up to three fluoro groups, $NO_2$, CN, a $(CH_2)_m OR^E$ (O-alkyl) group, a $(CH_2)_m C(O)R^E$ group, a $(CH_2)_m C(O)OR^E$ group, a $(CH_2)_m SO_3H$ group, a $(CH_2)_m OCOR^E$ (oxycarbonyl ester) group,

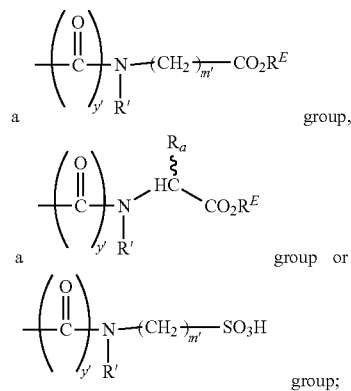

Each R' is independently H or a $C_1$-$C_3$ alkyl group;

$R_a$ is a sidechain derived from a natural or unnatural amino acid (D- or L-) wherein said amino acid is selected from the group consisting of alanine wherein said sidechain is methyl, arginine wherein said sidechain is propyleneguanidine, asparagine wherein said sidechain is methylenecarboxamide, aspartic acid wherein said sidechain is ethanoic acid, cysteine wherein said sidechain is thiol or di-thiol, glutamine wherein said sidechain is ethylcarboxyamide, glutamic acid wherein said sidechain is propanoic acid, histidine wherein said sidechain is methyleneimidazole, isoleucine wherein said sidechain is 1-methylpropane, leucine wherein said sidechain is 2-methylpropane, lysine wherein said sidechain is butyleneamine, methionine wherein said sidechain is ethylmethylthioether, phenylalanine wherein said sidechain is benzyl, proline wherein said sidechain $R_a$ forms a cyclic ring with R' and the adjacent nitrogen group to form a pyrrolidine group, hydroxyproline wherein said sidechain $R_a$ forms a cyclic ring with R' and the adjacent nitrogen group to form a hydroxypyrrolidine group, serine wherein said sidechain is methanol, threonine wherein said sidechain is 1-hydroxyethane, tryptophan wherein said sidechain is methyleneindole, tyrosine wherein said sidechain is methylene phenol or valine wherein said sidechain is isopropyl;

Each $R^E$ is independently H or a $C_1$-$C_6$ alkyl group optionally substituted with one or two hydroxyl groups or up to three chloro or fluoro groups;

$R_{1'}$, $R_{2'}$, $R_{3'}$, $R_{4'}$ and $R_{5'}$ are each independently H, a halogen, a $C_1$-$C_6$ alkyl group optionally substituted with one or two hydroxyl groups or up to three chloro or fluoro groups, $NO_2$, CN, a $(CH_2)_{m'} OR^E$ group, a $(CH_2)_{m'} C(O)OR^E$ group, a $(CH_2)_{m'} O$—$C(O)R^E$ group or a $(CH_2)_{m'} C(O)R^E$ group;

Each m' is independently 0, 1, 2, 3, 4, 5, or 6;
Each y' is independently 0, 1 or 2;
$R^{LABT}$ is an group,

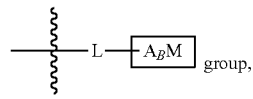

where L is a bond or at least one Linker, which chemically links the amide amine as indicated to the

 group; and the  group is at least one antibody binding moiety according to the chemical structure:

said $A_B M$ group is a group according to the chemical structure:

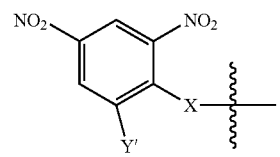

Where Y' is H;

X is O, $CH_2$, $NR^1$, S(O), $S(O)_2$, $-S(O)_2O$, $-OS(O)_2$, or $OS(O)_2O$; and $R^1$ is H, a $C_1$-$C_3$ alkyl group, or a $-C(O)(C_1$-$C_3)$ group, or a group according to the chemical structure:

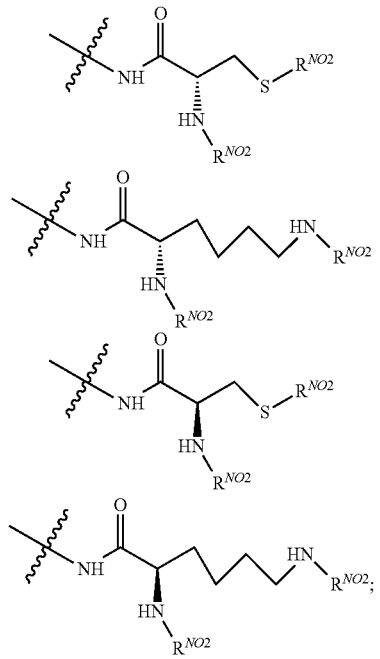

Where $R^{NO2}$ is a nitrophenyl or a dinitrophenyl group linked through an amino or thiol group as indicated; or a group according to the chemical structure:

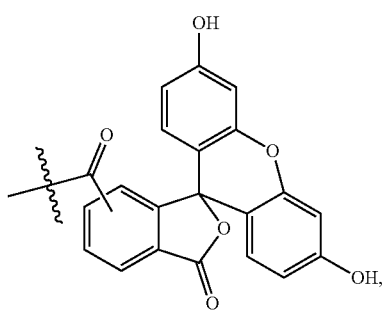

group according to the chemical formula:

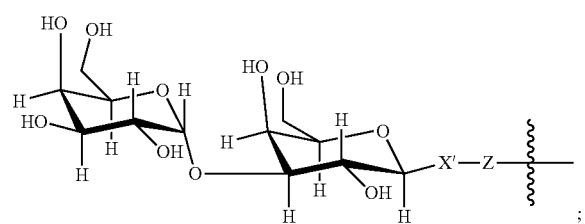

Where X' is $CH_2$, O, $N-R^{1'}$, or S;

$R^{1'}$ is H or $C_1$-$C_3$ alkyl; and

Z is a bond, a monosaccharide, disaccharide, oligosaccharide, glycoprotein or glycolipid, or a group according to the chemical structure:

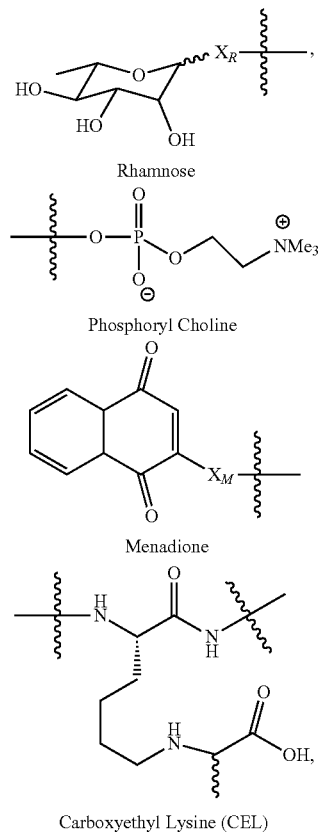

Where $X_R$ is O, S or $NR^1$; and
$X_M$ is O, $NR^1$ or S, and
$R^1$ is H or a $C_1$-$C_3$ alkyl group, or
a group according to the chemical structure:

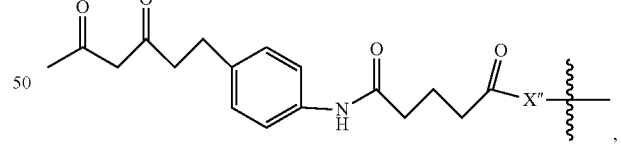

Where X'' is O, $CH_2$, $NR^1$, S; and
$R^1$ is H, a $C_1$-$C_3$ alkyl group or a $-C(O)(C_1$-$C_3)$ group;
or
a group according to the chemical structure:

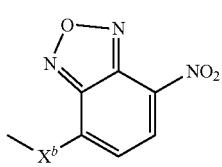

Where $X^b$ is a bond, O, $CH_2$ or $NR^1$ or S; and
$R^1$ is the same as above;
a pharmaceutically acceptable salt, stereoisomer, or enantiomer, solvate or polymorph thereof.

2. The compound according to claim 1 wherein $R_1$ is H, $CO_2H$ or $SO_3H$; $R_2$ is H, $CO_2H$, $SO_3H$, —$NHCH_2$—$CO_2H$, —$NHCH_2$—$SO_3H$, —C(O)—$NHCH_2$—$CO_2H$ or —C(O)—$NHCH_2$—$SO_3H$; $R_3$ is H, $CO_2H$, $SO_3H$, —$NHCH_2$—$CO_2H$, —$NHCH_2$—$SO_3H$, —C(O)—$NHCH_2$—$CO_2H$ or —C(O)—$NHCH_2$—$SO_3H$; $R_4$ is H, $SO_3H$ or $CO_2H$; $R_5$ is H, $SO_3H$ or $CO_2H$ and R', $R_{1'}$, $R_{2'}$, $R_{3'}$, $R_{4'}$ and $R_{5'}$ are H, or a pharmaceutically acceptable salt, stereoisomer, enantiomer thereof.

3. The compound according to claim 1 wherein $R_3$ is H, $CO_2H$ or $SO_3H$; $R_4$ is H or $CO_2H$; and $R_5$ is H.

4. The compound according to claim 2 wherein $R_3$ is H, $CO_2H$ or $SO_3H$; $R_4$ is H or $CO_2H$; and $R_5$ is H.

5. The compound according to claim 1 wherein $R_3$ is H, $CO_2H$ or $SO_3H$.

6. The compound according to claim 2 wherein $R_3$ is H, $CO_2H$ or $SO_3H$.

7. The compound according to claim 4 wherein $R_3$ is H.

8. The compound according to claim 1 wherein $R_1$ is H or $SO_3H$, $R_2$ is H, $CO_2H$, $SO_3H$, —$NHCH_2$—$CO_2H$, —$NHCH_2$—$SO_3H$, —C(O)—$NHCH_2$—$CO_2H$ or —C(O)—$NHCH_2$—$SO_3H$, $R_3$ is H or $SO_3H$ and $R_4$ is H or $CO_2H$, or a pharmaceutically acceptable salt thereof.

9. The compound according to claim 2 wherein $R_1$ is H or $SO_3H$, $R_2$ is H, $CO_2H$, $SO_3H$, —$NHCH_2$—$CO_2H$, —$NHCH_2$—$SO_3H$, —C(O)—$NHCH_2$—$CO_2H$ or —C(O)—$NHCH_2$—$SO_3H$, $R_3$ is H or $SO_3H$ and $R_4$ is H or $CO_2H$, or a pharmaceutically acceptable salt thereof.

10. The compound according to claim 1 wherein said Linker comprises a first linker group L1 which optionally includes a connector group CT, wherein said linker group L1 is a group comprising from 1 to 100 polyethyleneglycol (PEG) units, polypropylene glycol units, or polyethyleneglycol-co-polypropylene oligomer units; or
Linker is a group according to the chemical structure:

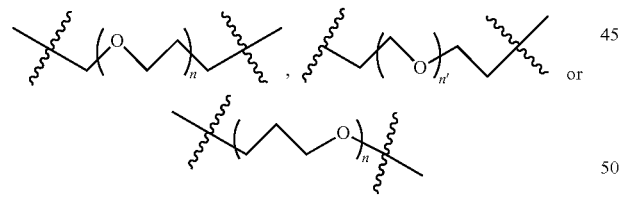

where each n and n' is independently 1 to 25; or
Linker is a group according to the chemical structure:

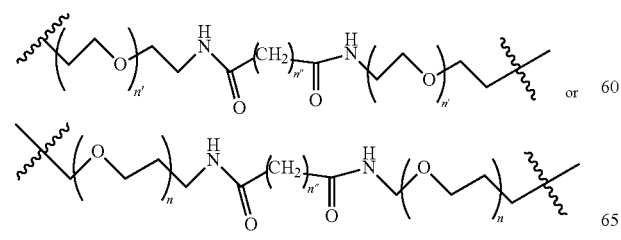

where each n and n' is independently 1 to 25; and each n" is independently 0 to 8; or
Linker is a polyamino acid group optionally comprising one or two connector groups CT comprising from 1 to 100 amino acid residues wherein said amino acid residues are selected from naturally occurring D and L amino acids; or
Linker is a group according to the chemical structure:

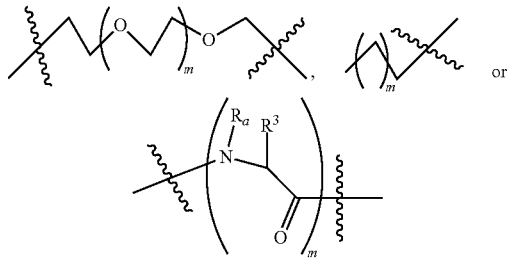

Where $R_a$ is H, C—$C_3$ alkyl or alkanol or forms a cyclic pyrrolidine or hydroxypyrrolidine ring with $R^3$ and $R^3$ is a side chain derived from an amino acid selected from the group consisting of alanine wherein said sidechain is methyl, arginine wherein said sidechain is propyleneguanidine, asparagine wherein said sidechain is methylenecarboxyamide, aspartic acid wherein said sidechain is ethanoic acid, cysteine wherein said sidechain is thiol, or di-thiol, glutamine wherein said sidechain is ethylcarboxyamide, glutamic acid wherein said sidechain is propanoic acid, histidine wherein said sidechain is methyleneimidazole, isoleucine wherein said sidechain is 1-methylpropane, leucine wherein said sidechain is 2-methylpropane, lysine wherein said sidechain is butyleneamine, methionine wherein said sidechain is ethylmethylthioether, phenylalanine wherein said sidechain is benzyl, wherein said sidechain $R_a$ forms a cyclic ring with R' and the adjacent nitrogen group to form a pyrrolidine group, hydroxyproline wherein said sidechain $R_a$ forms a cyclic ring with R' and the adjacent nitrogen group to form a hydroxypyrrolidine group, serine wherein said sidechain is methanol, threonine wherein said sidechain is 1-hydroxyethane, tryptophan wherein said sidechain is methyleneindole, tyrosine wherein said sidechain is methylene phenol or valine wherein said sidechain is isopropyl; and
m is an integer from 1 to 100; or
Linker is a group according to the chemical formula:

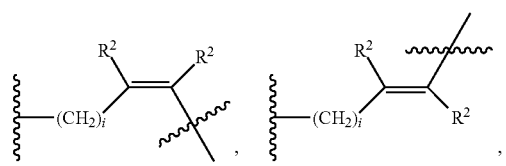

Where Z and Z' are each independently a bond, —$(CH_2)_i$—O, —$(CH_2)_i$—S, —$(CH_2)_i$—N—R,

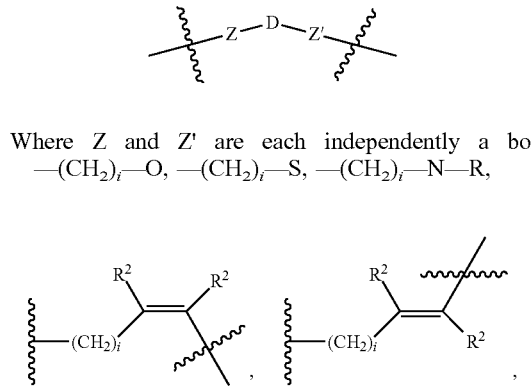

-continued

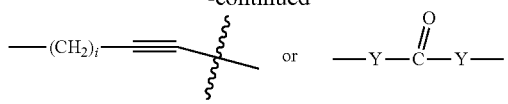

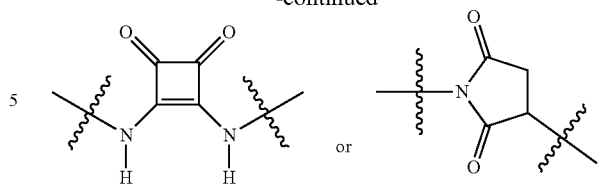

or a diamide group according to the structure:

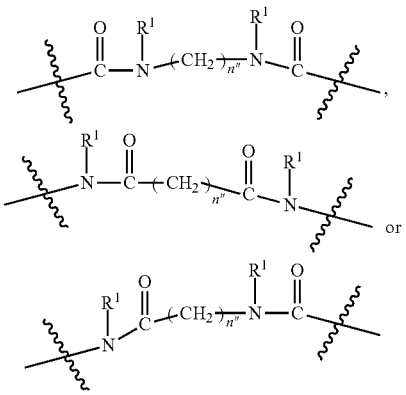

wherein said —(CH$_2$)$_i$ group, if present in Z or Z', is bonded to a connector (CT), an alternative linker, A$_B$M and/or the nitrogen to which R$^{LABT}$ is attached in said compound;

Each R is H, or a C$_1$-C$_3$ alkyl or alkanol group;
Each R$^2$ is independently H or a C$_1$-C$_3$ alkyl group;
Each Y is independently a bond, O, S or N—R;
Each i is independently 0 to 100;
D is

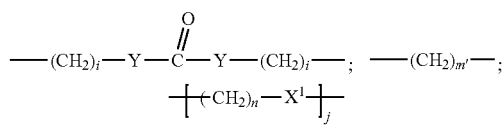

a bond, with the proviso that Z, Z' and D are not each simultaneously bonds;
j is 1 to 15;
m' is 1 to 15;
n is 1 to 45;
X$^1$ is O, S or N—R; and
R is as described above,
or a pharmaceutically acceptable salt thereof;
and said CT group is a group according to the chemical structure:

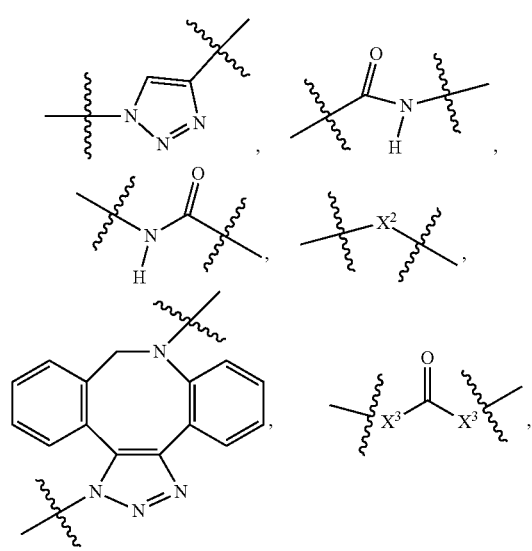

Where X$^2$ is CH$_2$, O, S, NR$^4$, C(O), S(O), S(O)$_2$, —S(O)$_2$O, —OS(O)$_2$, or OS(O)$_2$O;
X$^3$ is O, S, NR$^4$;
R$^4$ is H, a C$_1$-C$_3$ alkyl or alkanol group, or a —C(O)(C$_1$-C$_3$) group;
Each R$^1$ is independently H or a C$_1$-C$_3$ alkyl group; and n" is independently 0 to 8.

11. The compound according to claim 10 wherein said Linker comprises a first linker group L1 which optionally includes a connector group CT and an optional linker group L2, wherein said linker group L2 optionally includes a second connector group CT, and wherein said first linker group L1 is linked to said optional second linker group L2 directly or through said optional first or second CT group and wherein said linker group L1 and L2 are each independently a linker group as set forth in claim 10 and said first and second CT groups are each independently a CT group as set forth in claim 10.

12. The compound according to claim 1 wherein

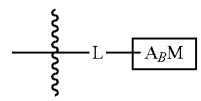

is

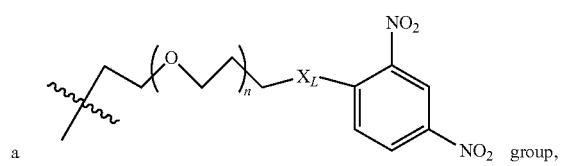

group,

-continued

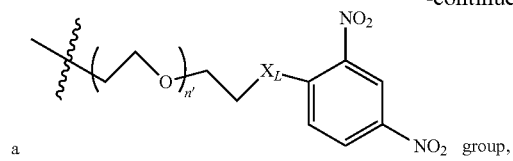

a

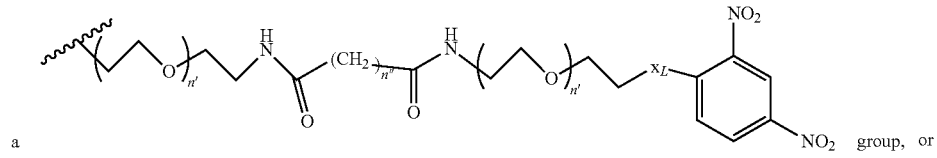

a

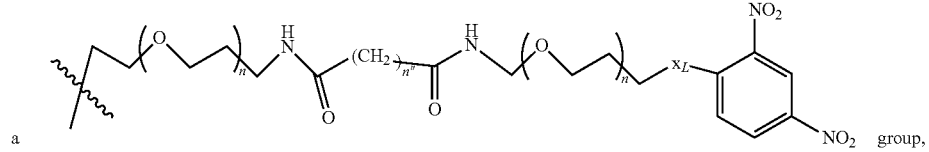

a where $X_L$ is $N(R^1)$, O, S, S(O), $SO_2$, $S(O)_2O$, $—OS(O)_2$, or $OS(O)_2O$; and
$R^1$ is H, a $C_1$-$C_3$ alkyl group or a $—C(O)(C_1$-$C_3)$ group;
each n and n' is independently 1 to 25; and
each n" is independently 0 to 8.

13. The compound to claim 1 wherein said Linker is a group comprising from 1 to 100 polyethyleneglycol (PEG) units, polypropylene glycol linkages, or polyethyleneglycol-co-polypropylene oligomers.

14. The compound according claim 1 wherein said Linker is a group according to the chemical structure:

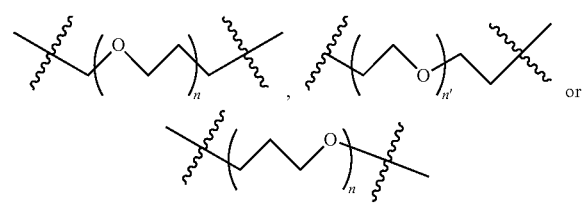

where each n and n' is independently 1 to 25.

15. The compound according to claim 1 wherein said Linker is a group according to the chemical structure:

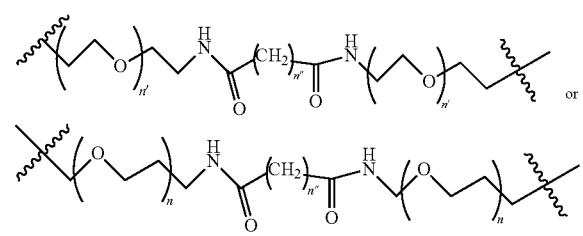

where each n and n' is independently 1 to 25; and
each n" is independently 0 to 8.

16. The compound according to claim 1 wherein said Linker is a polyamino acid optionally comprising one or two connector groups CT comprising from 1 to 100 amino acid residues wherein said amino acid residues are selected from naturally occurring D and L amino acids, or Linker is a group according to the chemical structure:

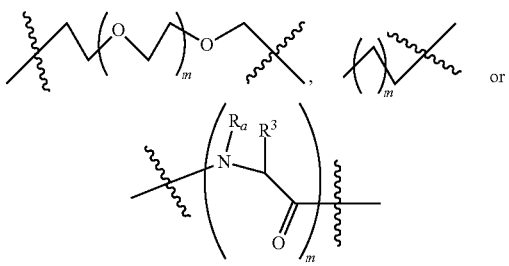

Where $R_a$ is H, $C_1$-$C_3$ alkyl or alkanol or forms a cyclic pyrrolidine or hydroxypyrrolidine ring with $R^3$ and $R^3$ is a side chain derived from an amino acid selected from the group consisting of alanine wherein said sidechain is methyl, arginine wherein said sidechain is propyleneguanidine, asparagine wherein said sidechain is methylenecarboxyamide, aspartic acid wherein said sidechain is ethanoic acid, cysteine wherein said sidechain is thiol or di-thiol, glutamine wherein said sidechain is ethylcarboxyamide, glutamic acid wherein said sidechain is propanoic acid, histidine wherein said sidechain is methyleneimidazole, isoleucine wherein said sidechain is 1-methylpropane, leucine wherein said sidechain is 2-methylpropane, lysine wherein said sidechain is butyleneamine, methionine wherein said sidechain is ethylmethylthioether, phenylalanine wherein said sidechain is benzyl, wherein said sidechain $R_a$ forms a cyclic ring with R' and the adjacent nitrogen group to form a pyrrolidine group, hydroxyproline wherein said sidechain $R_a$ forms a cyclic ring with R' and the adjacent nitrogen group to form a hydroxypyrrolidine group, serine wherein said sidechain is methanol, threonine wherein said sidechain is 1-hydroxyethane, tryptophan wherein said sidechain is methyleneindole, tyrosine wherein said sidechain is methylene phenol or valine wherein said sidechain is isopropyl; and m is an integer from 1 to 100.

17. The compound according to claim 1 wherein said Linker is a group according to the chemical formula:

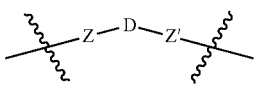

Where Z and Z' are each independently a bond, —(CH$_2$)$_i$—O, —(CH$_2$)$_i$—S, —(CH$_2$)$_i$—N—R,

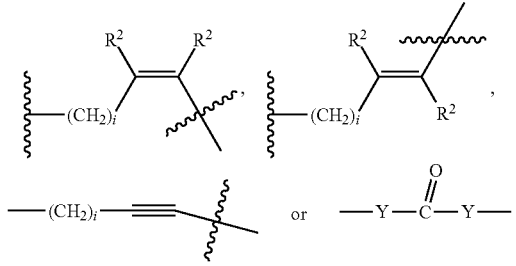

wherein said —(CH$_2$)$_i$ group, if present in Z or Z', is bonded to a connector (CT), an alternative linker, A$_B$M and/or the nitrogen to which R$^{LABT}$ is attached in said compound;

Each R is H, or a C$_1$-C$_3$ alkyl or alkanol group;
Each R$^2$ is independently H or a C$_1$-C$_3$ alkyl group;
Each Y is independently a bond, O, S or N—R;
Each i is independently 0 to 100;
D is

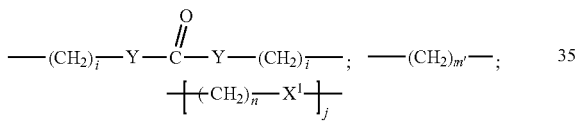

a bond, with the proviso that Z, Z' and D are not each simultaneously bonds;
j is 1 to 100; m' is 1 to 100; n is 1 to 100;
X' is O, S or N—R; and
R is as described above,
or a pharmaceutical salt thereof.

18. The compound according to claim 1 wherein said Linker is a group according to the chemical structure:

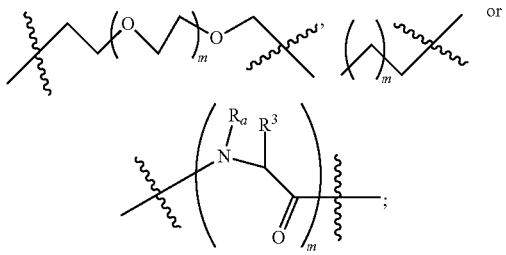

a polypropylene glycol or polypropylene-co-polyethylene glycol linker containing between 1 and 100 alkyleneglycol units;
Where R$_a$ is H, C$_1$-C$_3$ alkyl or alkanol or forms a cyclic ring with R$^3$ when R$^3$ is a sidechain of proline and R$^3$ is a side chain derived from a naturally occurring D- or L-amino acid, wherein said amino acid is selected from the group consisting of alanine wherein said sidechain is methyl, arginine wherein said sidechain is propyleneguanidine, asparagine wherein said sidechain is methylenecarboxyamide, aspartic acid wherein said sidechain is ethanoic acid, cysteine wherein said sidechain is thiol or di-thiol, glutamine wherein said sidechain is ethylcarboxyamide, glutamic acid wherein said sidechain is propanoic acid, histidine wherein said sidechain is methyleneimidazole, isoleucine wherein said sidechain is 1-methylpropane, leucine wherein said sidechain is 2-methylpropane, lysine wherein said sidechain is butyleneamine, methionine wherein said sidechain is ethylmethylthioether, phenylalanine wherein said sidechain is benzyl, proline wherein said sidechain R$_a$ forms a cyclic ring with R' and the adjacent nitrogen group to form a pyrrolidine group, hydroxyproline wherein said sidechain R$_a$ forms a cyclic ring with R' and the adjacent nitrogen group to form a hydroxypyrrolidine group, serine wherein said sidechain is methanol, threonine wherein said sidechain is 1-hydroxyethane, tryptophan wherein said sidechain is methyleneindole, tyrosine wherein said sidechain is methylene phenol or valine wherein said sidechain is isopropyl; and Each m is independently an integer from 1 to 100.

19. The compound according to claim 1 wherein said A$_B$M group is a group according to the chemical structure:

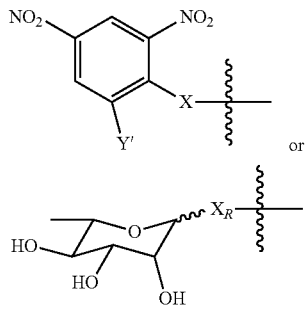

Where Y' is H or NO$_2$;
X is O, CH$_2$, NR$^1$, S(O), S(O)$_2$, —S(O)$_2$O, —OS(O)$_2$, or OS(O)$_2$O; and
R$^1$ is H, a C$_1$-C$_3$ alkyl group, or a —C(O)(C$_1$-C$_3$) group; and
X$_R$ is O, S or NR$^1$.

20. The compound according to claim 1 wherein said A$_B$M group is a group according to the chemical structure:

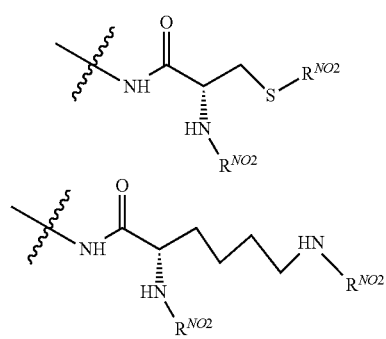

-continued

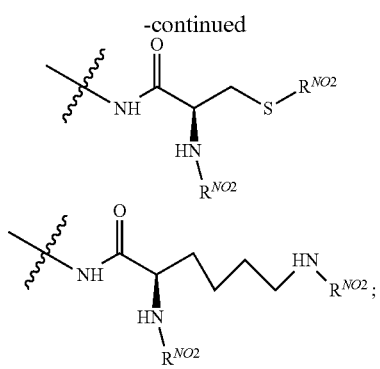

Where $R^{NO2}$ is a nitrophenyl or a dinitrophenyl group linked through an amino or thiol group as indicated;
or said $A_BM$ group is a group according to the chemical structure:

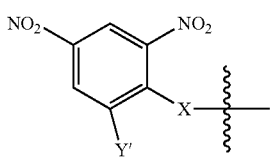

Where Y' is H;
X is O, $CH_2$, $NR^1$, S(O), $S(O)_2$, —$S(O)_2O$, —$OS(O)_2$, or $OS(O)_2O$; and
$R^1$ is H, a $C_1$-$C_3$ alkyl group, or a —$C(O)(C_1$-$C_3)$ group.

21. The compound according to claim 1 wherein said $A_BM$ group is a group according to the chemical structure:

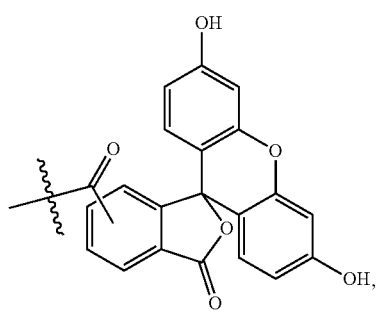

or a
a group according to the chemical formula:

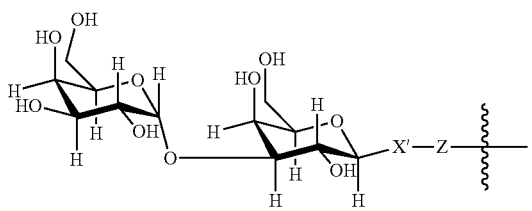

Where X' is $CH_2$, O, N—$R^{1'}$, or S;
$R^{1'}$ is H or $C_1$-$C_3$ alkyl; and
Z is a bond, a monosaccharide, disaccharide, oligosaccharide, glycoprotein or glycolipid.

22. The compound according to claim 1 wherein said $A_BM$ group is a group according to the chemical structure:

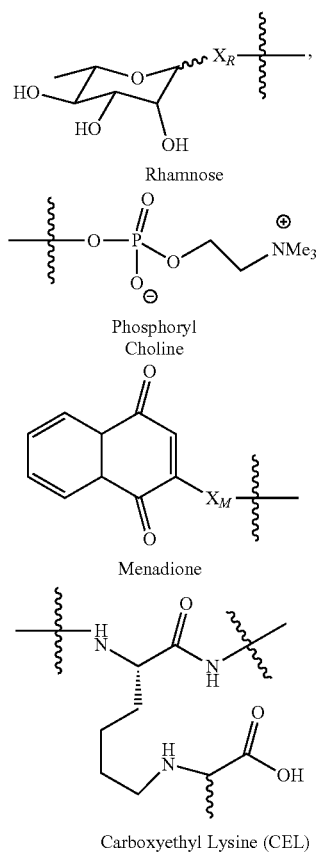

Where $X_R$ is O, S or $NR^1$; and
$X_M$ is O, $NR^1$ or S, and
$R^1$ is H or a $C_1$-$C_3$ alkyl group.

23. The compound according to claim 22 wherein said $A_BM$ group comprises a rhamnose group.

24. The compound according to claim 1 wherein said $A_BM$ group is a group according to the chemical structure:

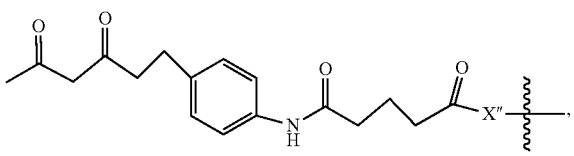

Where X" is O, $CH_2$, $NR^1$, S; and
$R^1$ is H, a $C_1$-$C_3$ alkyl group or a —$C(O)(C_1$-$C_3)$ group;
or

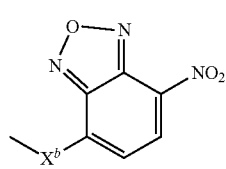

Where $X^b$ is a bond, O, $CH_2$ or $NR^1$ or S; and
$R^1$ is the same as above; or a group according to the chemical structure:

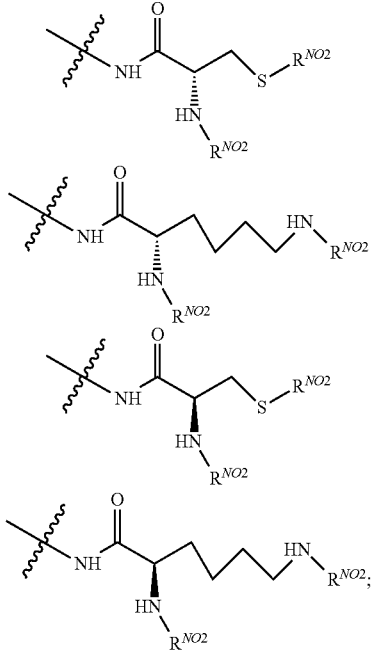

Where $R^{NO2}$ is a nitrophenyl or a dinitrophenyl group linked through an amino or thiol group as indicated; or
a dinitrophenyl group according to the chemical structure:

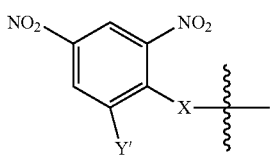

Where Y' is H;
X is O, $CH_2$, $NR^1$, S(O), $S(O)_2$, —$S(O)_2O$, —$OS(O)_2$, or $OS(O)_2O$; and
$R^1$ is H, a $C_1$-$C_3$ alkyl group, or a —$C(O)(C_1$-$C_3)$ group; or
a fluorescein group according to the chemical structure:

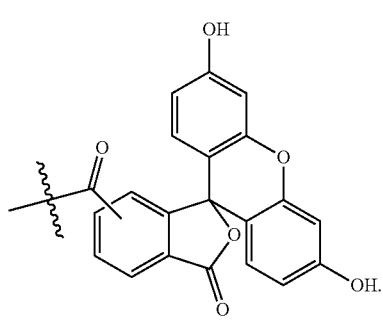

25. The compound according to claim 1 wherein said $A_BM$ group is a dinitrophenyl group or a rhamnose group.
26. The compound according to claim 10 wherein said CT group is a group according to the chemical structure:

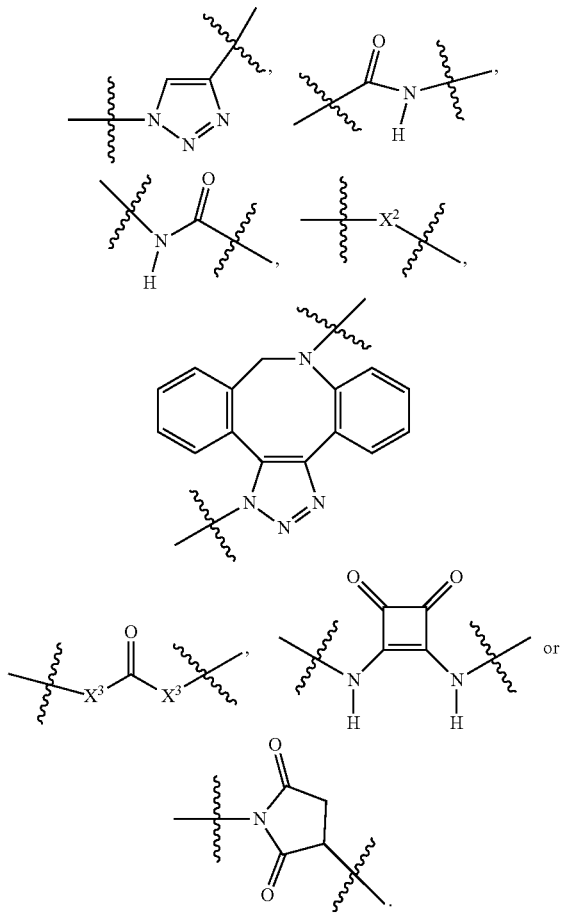

27. The compound according to claim 10 wherein said CT group is a group according to the chemical structure:

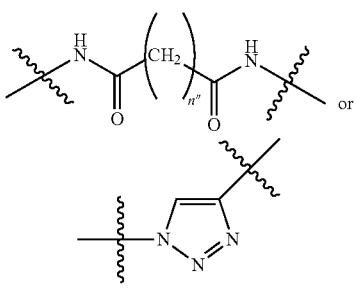

Where n" is 1-7.

28. The compound of claim 1 which is compound 1-ABT-1, 1-ABT-2, 1-ABT-3, 2-ABT-1, 2-ABT-2, 2-ABT-3, 3-ABT-1, 3-ABT-2, 3-ABT-3, 4-ABT-1, 4-ABT-2, 4-ABT-3, 5-ABT-1, 5-ABT-2, 5-ABT-3, 6-ABT-1, 6-ABT-2 or 6-ABT-3 of FIG. 4 or a pharmaceutically acceptable salt or enantiomer thereof.

29. The compound of claim 28 which is compound 6-ABT-1 or an enantiomer or pharmaceutically acceptable salt thereof.

30. A compound according to any one of the following chemical structures:

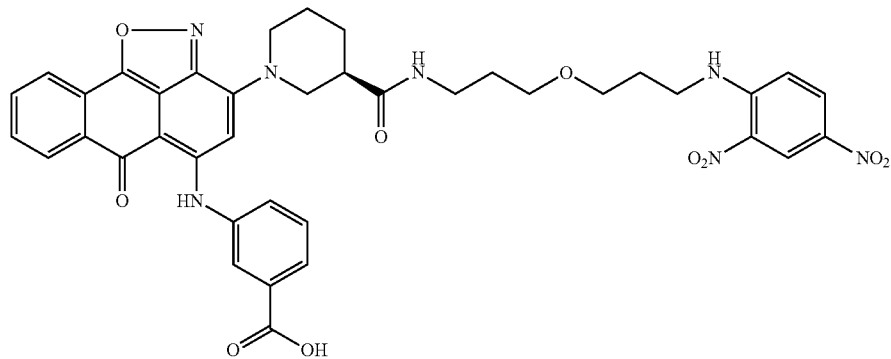
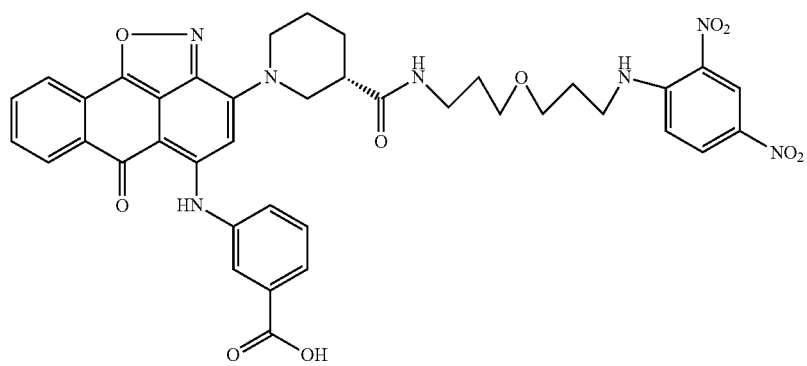
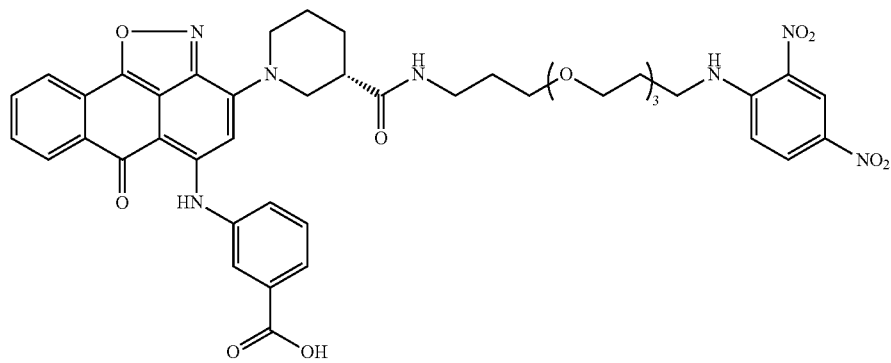
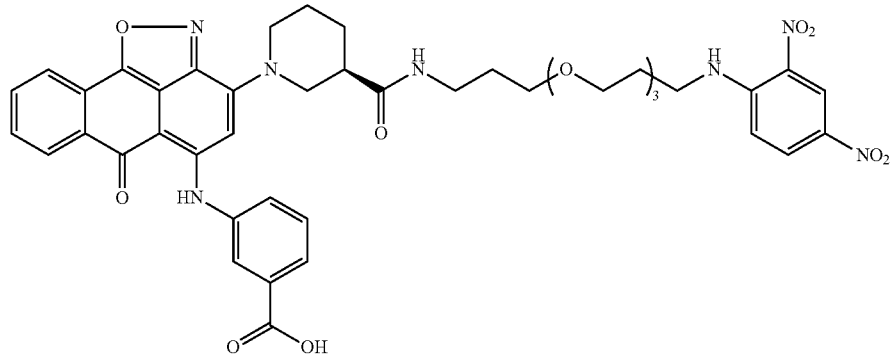

-continued
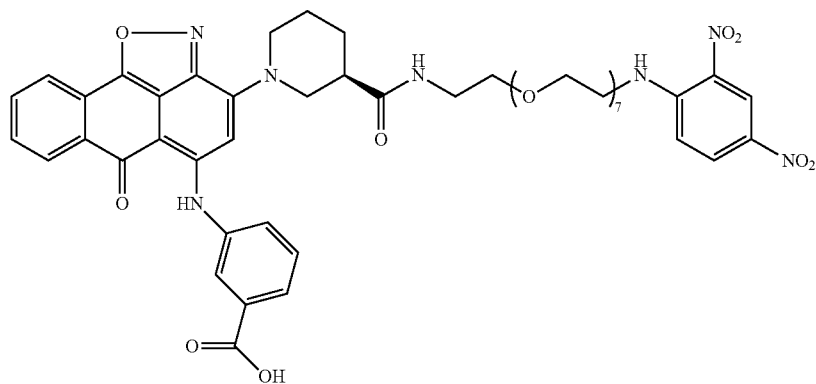
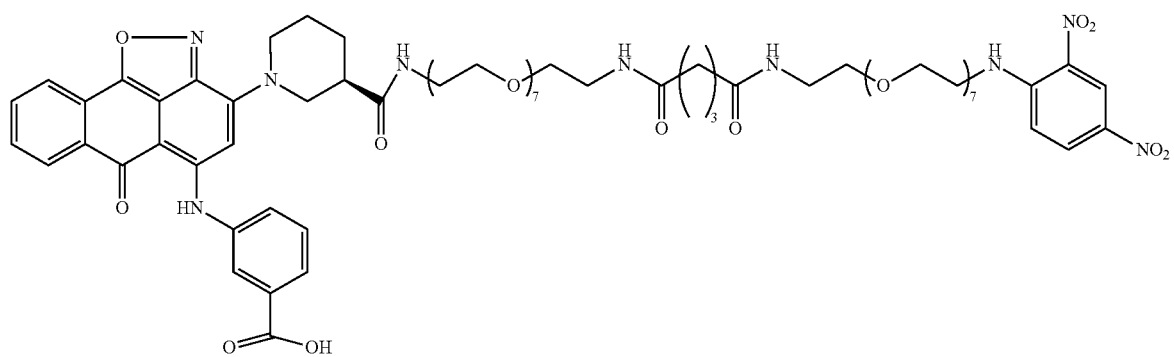
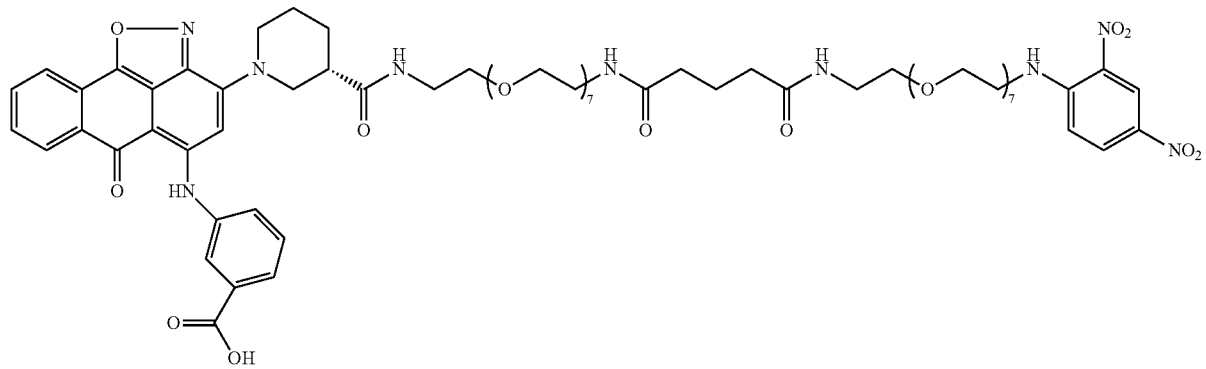
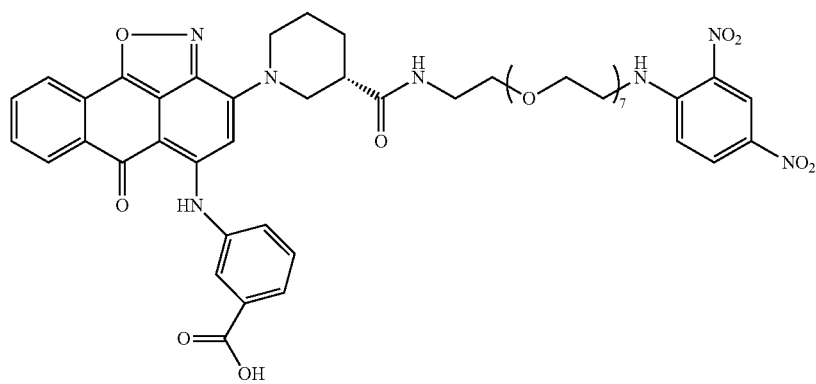

-continued
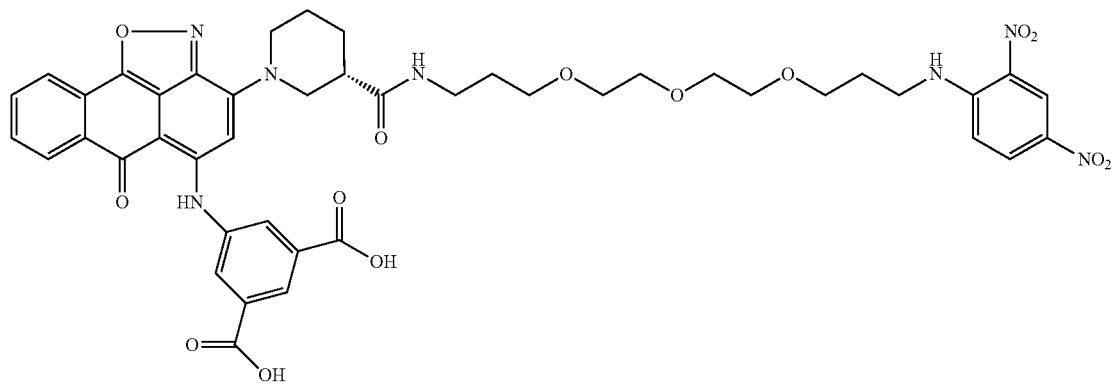
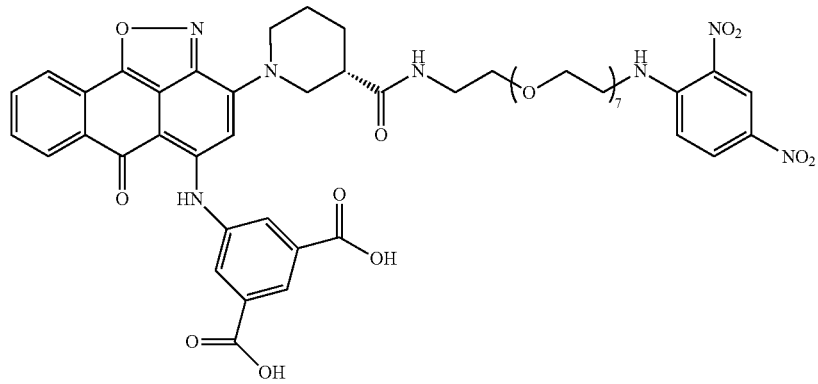
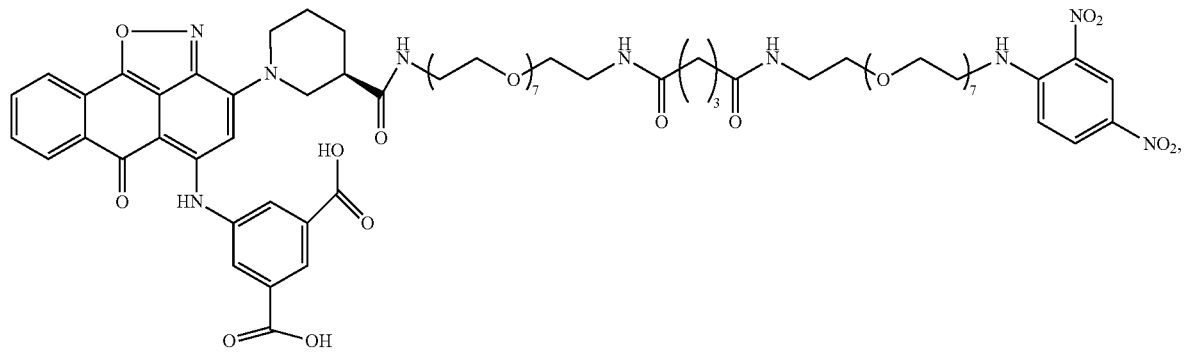
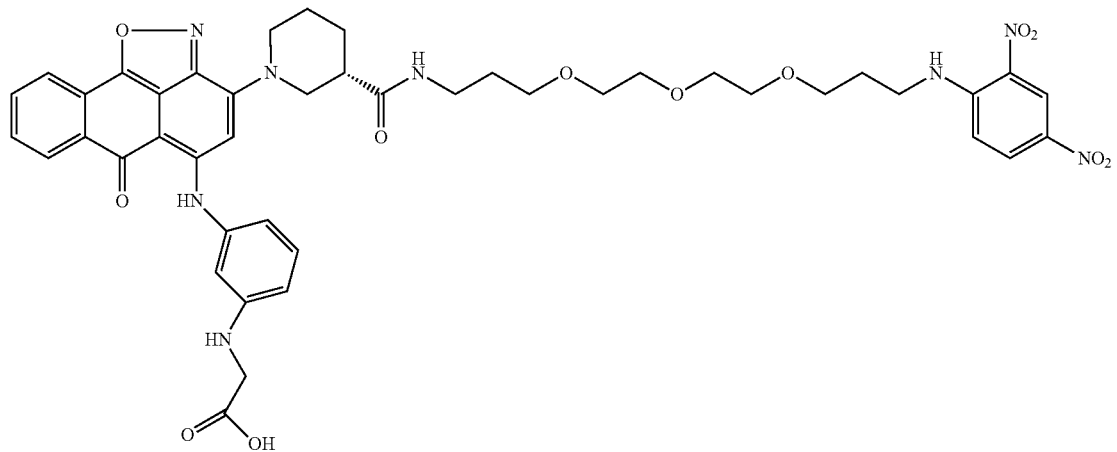

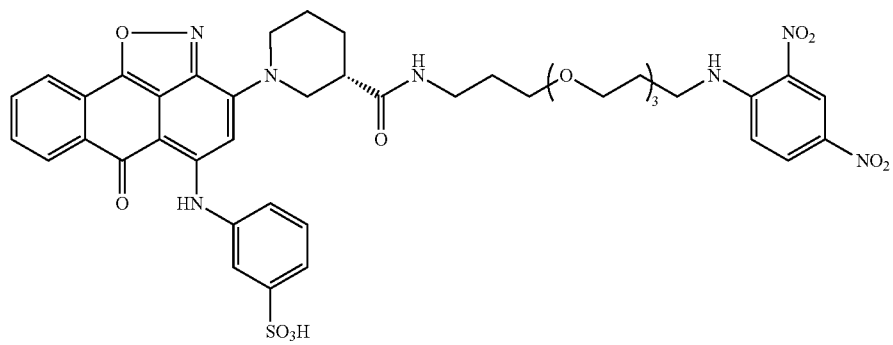
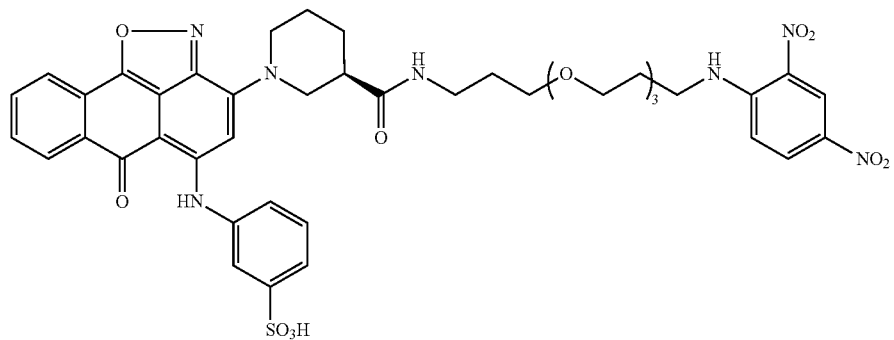
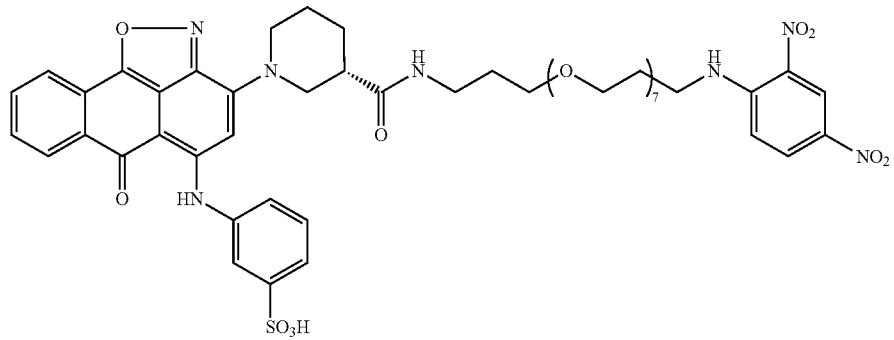
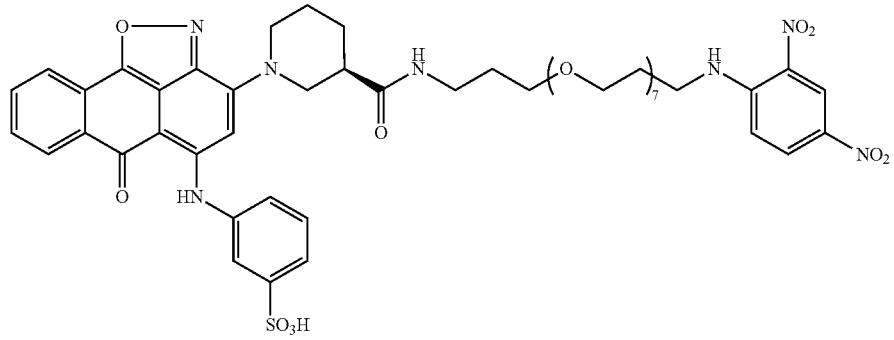
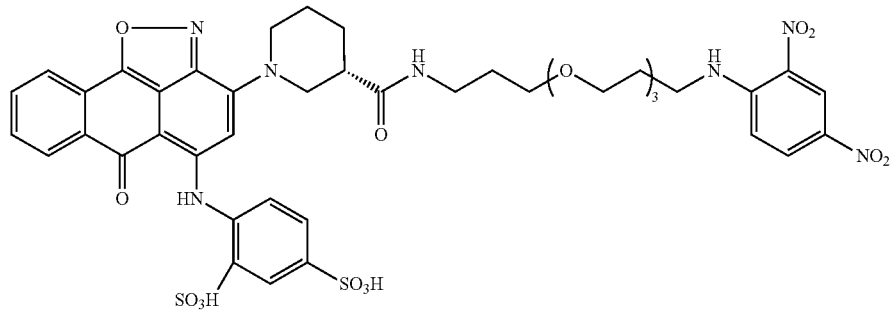

-continued
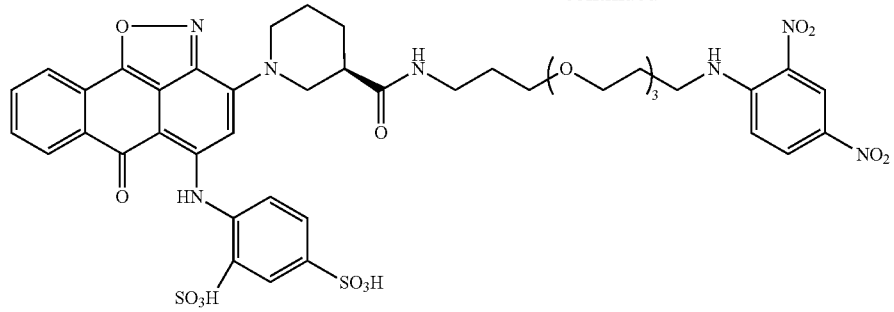
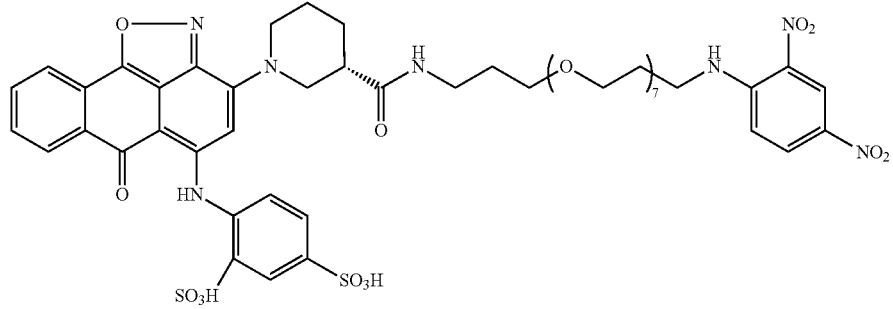
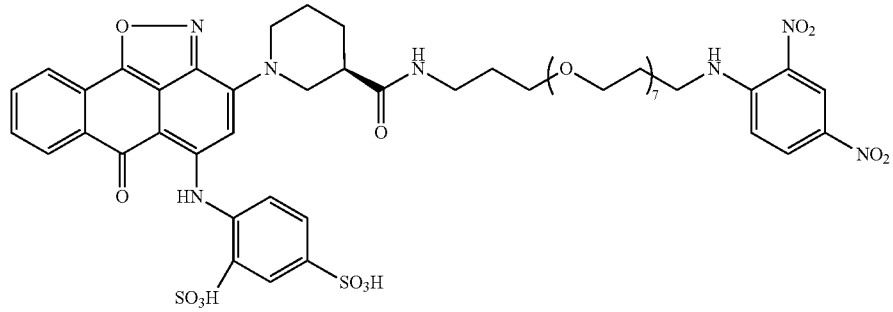
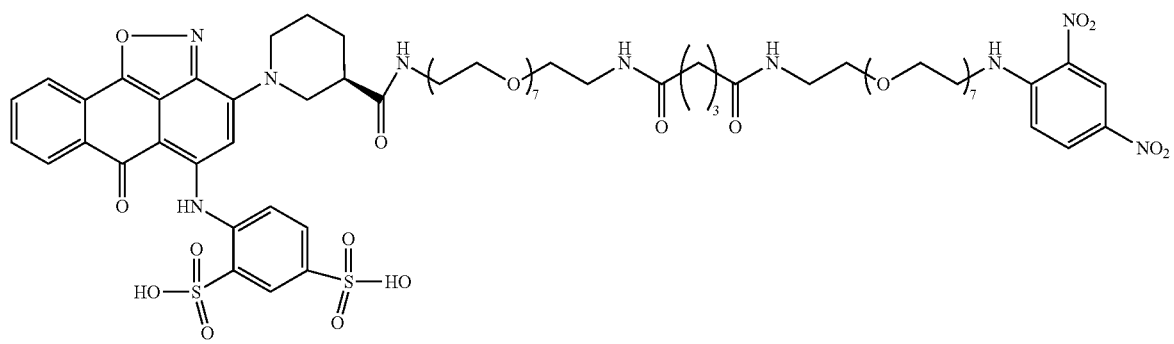
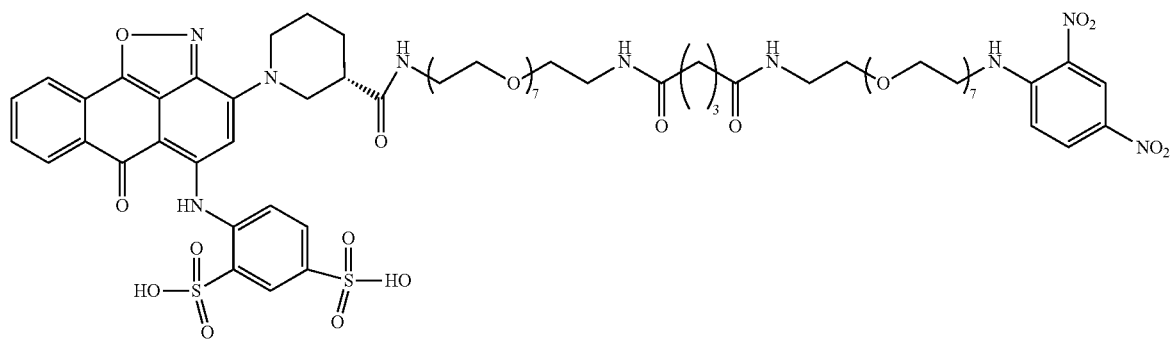

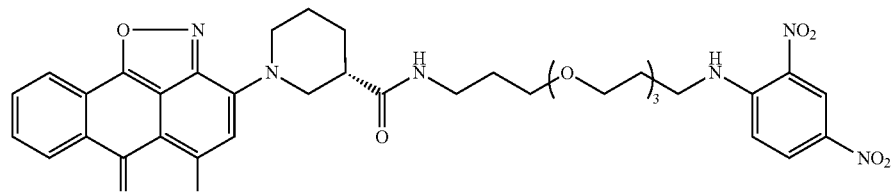
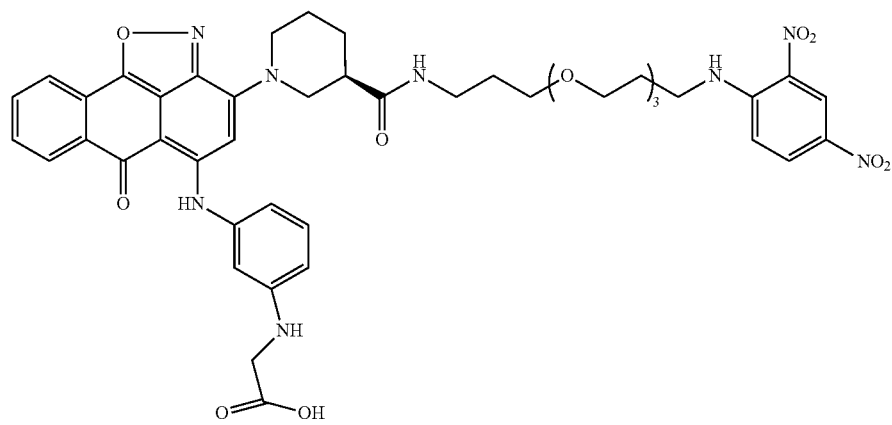
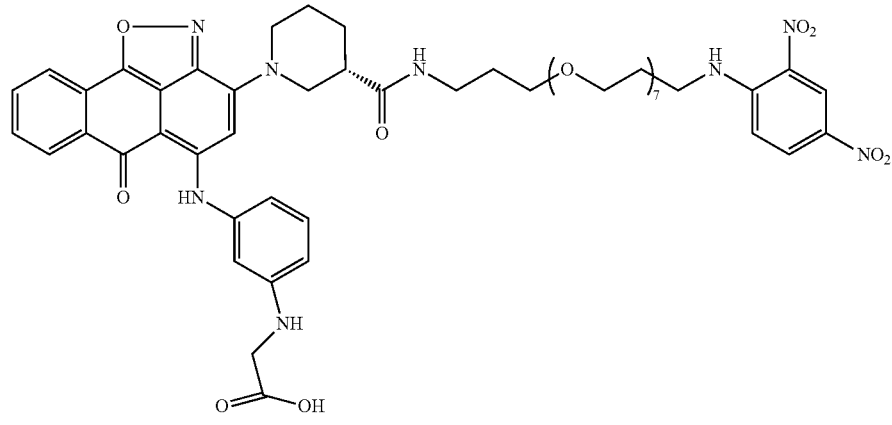
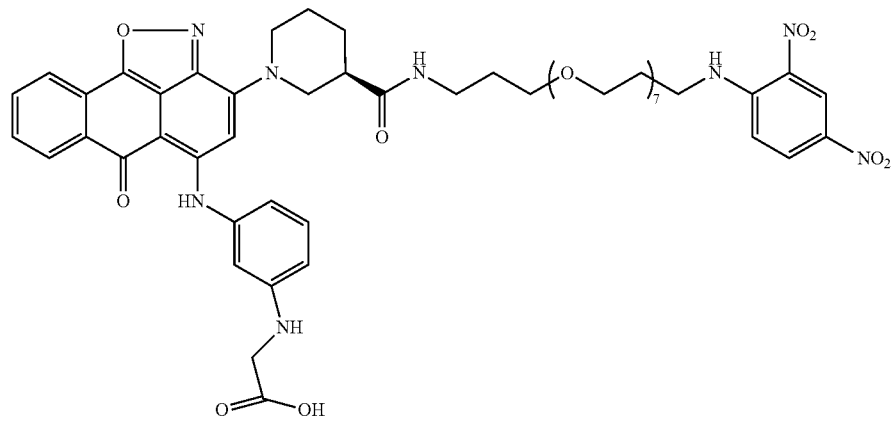

-continued
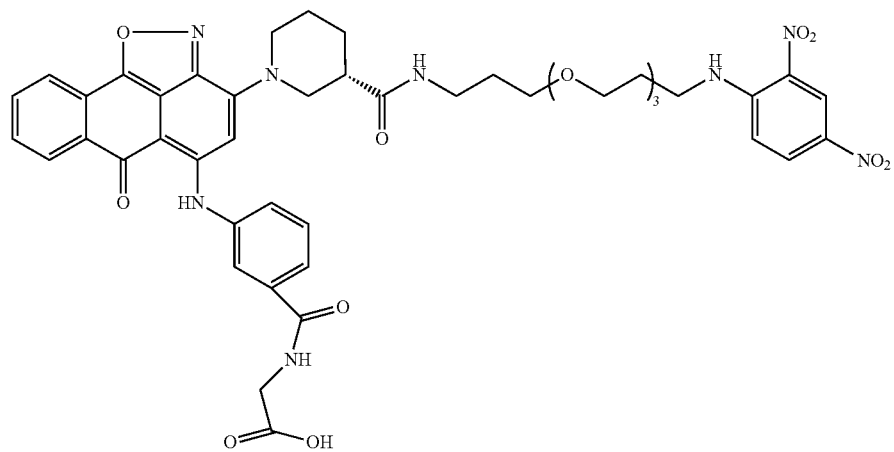
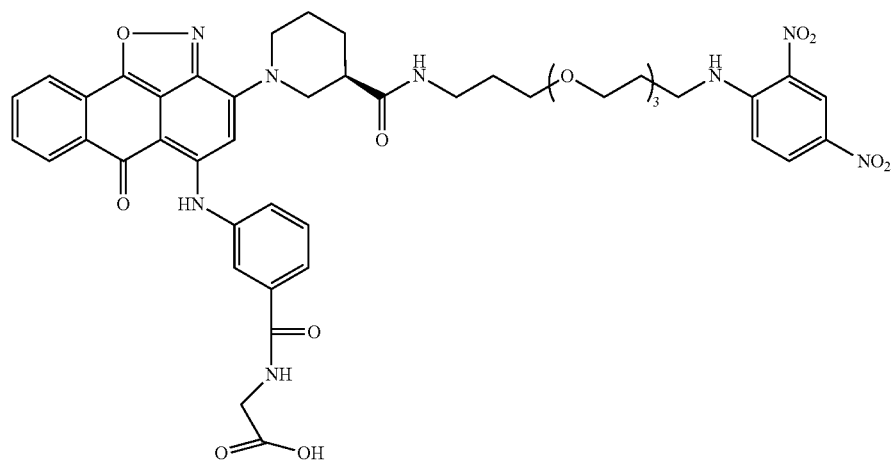
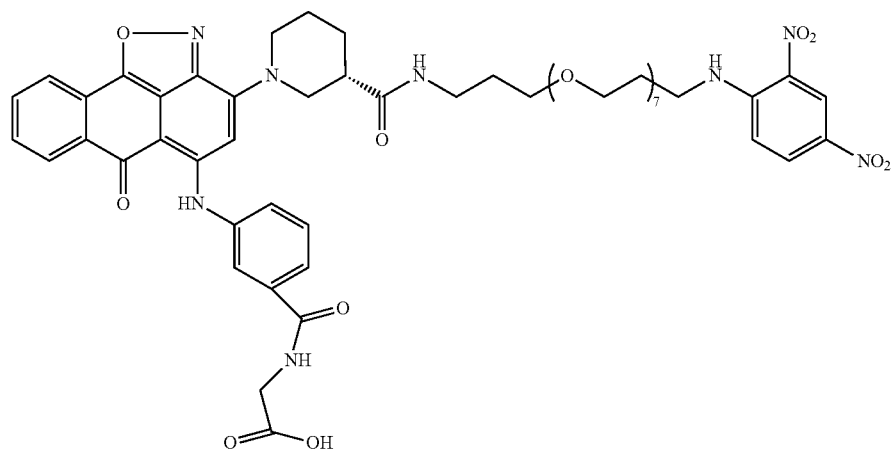

-continued

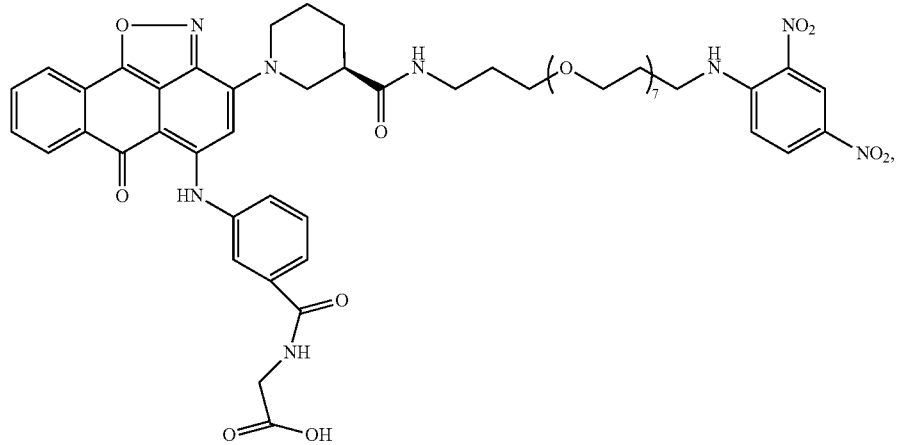

or a pharmaceutically acceptable salt or enantiomer thereof.

31. A pharmaceutical composition comprising an effective amount of a compound according to claim 1, in combination with a pharmaceutically acceptable carrier, additive or excipient.

32. A pharmaceutical composition comprising an effective amount of a compound according to claim 30, in combination with a pharmaceutically acceptable carrier, additive or excipient.

33. A pharmaceutical composition according to claim 32 further in combination with an additional anticancer agent.

34. The composition according to claim 33 wherein said additional anticancer agent is an antimetabolite, an inhibitor of topoisomerase I and II, an alkylating agent, a microtubule inhibitor or a mixture thereof.

35. The composition according to claim 34 wherein said additional anticancer agent is a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody or a mixture thereof.

36. The composition according to claim 34 wherein said additional anticancer agent is everolimus, trabectedin, abraxane, TLK 286, AV-299, DN-101, pazopanib, GSK690693, RTA 744, ON 0910.Na, AZD 6244 (ARRY-142886), AMN-107, TK1-258, GSK461364, AZD 1152, enzastaurin, vandetanib, ARQ-197, MK-0457, MLN8054, PHA-739358, R-763, AT-9263, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), B estradiol, estrogen, conjugated estrogen, bevacizumab, IMC-1C11, CHIR-258, 3-[5-(methylsulfonylpiperadinemethyl)-indolylj-quinolone, vatalanib, AG-013736, AVE-0005, the acetate salt of [D-Ser(Bu t) 6, Azgly 10] (pyro-Glu-His-Trp-Ser-Tyr-D-Ser(Bu t)-Leu-Arg-Pro-Azgly-NH$_2$ acetate [C$_{59}$H$_{84}$N$_{18}$Oi$_4$-(C$_2$H$_4$O$_2$)$_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, lonafarnib, BMS-214662, tipifarnib; amifostine, NVP-LAQ824, suberoyl analide hydroxamic acid, valproic acid, trichostatin A, FK-228, SU 11248, sorafenib, KRN951, aminoglutethimide, arnsacrine, anagrelide, L-asparaginase, *Bacillus* Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa, ipilimumab, nivolomuab, pembrolizumab, dabrafenib, trametinib, vemurafenib or a mixture thereof.

* * * * *